(12) United States Patent
Barak et al.

(10) Patent No.: US 7,541,151 B2
(45) Date of Patent: *Jun. 2, 2009

(54) SINGLE-CELL BIOSENSOR FOR THE MEASUREMENT OF GPCR LIGANDS IN A TEST SAMPLE

(75) Inventors: Lawrence S. Barak, Durham, NC (US); Michael A. Shetzline, Chapel Hill, NC (US); Robert H. Oakley, Durham, NC (US); Marc G. Caron, Hillsborough, NC (US)

(73) Assignee: Duke University, Durham, NC (US)

( * ) Notice: Subject to any disclaimer, the term of this patent is extended or adjusted under 35 U.S.C. 154(b) by 1116 days.

This patent is subject to a terminal disclaimer.

(21) Appl. No.: 10/161,916

(22) Filed: Jun. 4, 2002

(65) Prior Publication Data

US 2009/0075314 A1    Mar. 19, 2009

Related U.S. Application Data

(63) Continuation-in-part of application No. 09/631,468, filed on Aug. 3, 2000, now abandoned, which is a continuation of application No. 09/233,530, filed on Jan. 20, 1999, now Pat. No. 6,110,693, which is a continuation of application No. 08/869,568, filed on Jun. 5, 1997, now Pat. No. 5,891,646.

(60) Provisional application No. 60/295,945, filed on Jun. 5, 2001.

(51) Int. Cl.
*G01N 33/566* (2006.01)
*G01N 21/76* (2006.01)
*G01N 33/53* (2006.01)

(52) U.S. Cl. .................. 435/7.1; 435/7.2; 435/7.21; 436/172; 436/501; 530/350; 536/23.4

(58) Field of Classification Search .................. None
See application file for complete search history.

(56) References Cited

U.S. PATENT DOCUMENTS

| | | | |
|---|---|---|---|
| 3,654,090 A | 4/1972 | Schuurs et al. | |
| 3,850,752 A | 11/1974 | Schuurs et al. | |
| 4,016,043 A | 4/1977 | Schuurs et al. | |
| 4,219,335 A | 8/1980 | Ebersole | |
| 4,324,633 A | 4/1982 | Lovejoy | |
| 4,341,761 A | 7/1982 | Ganfield et al. | |
| RE31,006 E | 8/1982 | Schuurs et al. | |
| 4,342,566 A | 8/1982 | Theofilopoulos et al. | |
| 4,399,121 A | 8/1983 | Albarella et al. | |
| 4,426,330 A | 1/1984 | Sears | |
| 4,427,783 A | 1/1984 | Newman et al. | |
| 4,444,887 A | 4/1984 | Hoffmann | |
| 4,451,570 A | 5/1984 | Royston et al. | |
| 4,466,917 A | 8/1984 | Nussenzweig et al. | |
| 4,472,500 A | 9/1984 | Milstein et al. | |
| 4,491,632 A | 1/1985 | Wands et al. | |
| 4,493,795 A | 1/1985 | Nestor, Jr. et al. | |
| 4,493,890 A | 1/1985 | Morris | |
| 4,534,899 A | 8/1985 | Sears | |
| 4,816,397 A | 3/1989 | Boss et al. | |
| 4,816,567 A | 3/1989 | Cabilly et al. | |
| 4,908,773 A | 3/1990 | Pantoliano et al. | |
| 4,981,784 A | 1/1991 | Evans et al. | |
| 5,034,506 A | 7/1991 | Summerton et al. | |
| 5,264,221 A | 11/1993 | Tagawa et al. | |
| 5,284,746 A | 2/1994 | Sledziewski et al. | |
| 5,292,726 A * | 3/1994 | Ashton et al. .................. 514/85 |
| 5,324,633 A | 6/1994 | Fodor et al. | |
| 5,352,660 A | 10/1994 | Pawson | |
| 5,366,889 A | 11/1994 | MacDonald et al. | |
| 5,462,856 A | 10/1995 | Lerner et al. | |
| 5,468,854 A | 11/1995 | McCabe et al. | |
| 5,482,835 A | 1/1996 | King et al. | |
| 5,491,084 A | 2/1996 | Chalfie et al. | |
| 5,522,896 A | 6/1996 | Prescott | |
| 5,532,157 A | 7/1996 | Fink | |
| 5,539,082 A | 7/1996 | Nielsen et al. | |
| 5,541,071 A * | 7/1996 | Kopin ....................... 435/7.21 |

(Continued)

FOREIGN PATENT DOCUMENTS

WO    WO88/03168 A1    5/1988

(Continued)

OTHER PUBLICATIONS

Heim et al Proc.Natl.Acad.Sci, vol. 91, 12501-12504, 1994).*
Ferguson et al Can J. Physiol Pharmacol, vol. 74, 1095-1110, 1996.*
Ferguson et al Science, Vo. 271, 363-365, 1996.*
Goodman et al Nature, vol. 383, 447-449, 1996.*
Zastrow et al, J. Biol. Chem., vol. 267, Issue 5, 3530-3538, Feb. 1992.*
Ping Wang et al, Subcellular Localization of beta-Arrestins is Determined by Their Intact N Domain and the Nuclear Export Signal at the C Terminus, J. Biol. Chem., vol. 278, Issue 13, 11648-11653, Mar. 28, 2003.*
G. H. Scott et al , Differential Nucleocytoplasmic Shuttling of Beta-Arrestins, J. Biol. Chem., vol. 277, Issue 40, 37693-37701, Oct. 4, 2002.*
Xiufeng Song et al Visual and Both Non-visual Arrestins in Their "Inactive" Conformation Bind JNK3 and Mdm2 and Relocalize Them from the Nucleus to the Cytoplasm J. Biol. Chem., vol. 281, Issue 30, 21491-21499, Jul. 28, 2006.*

(Continued)

*Primary Examiner*—Gary B Nickol
*Assistant Examiner*—Nirmal S Basi
(74) *Attorney, Agent, or Firm*—Gargi Talukder; David J. Brezner; Morgan Lewis & Bockius LLP

(57) ABSTRACT

The present invention is related to the detection of GPCR ligands in a test sample by using a single cell biosensor expressing a GPCR. Preferably, the test sample is derived from a biological or environmental sample. This invention may be used to detect the presence of a disease or to detect the presence of a harmful agent in the environment. Included in the present invention is an array of biosensors that detect ligands of various GPCRs.

35 Claims, 19 Drawing Sheets

U.S. PATENT DOCUMENTS

| | | | |
|---|---|---|---|
| 5,541,309 | A | 7/1996 | Prasher |
| 5,569,824 | A | 10/1996 | Donehower et al. |
| 5,569,827 | A | 10/1996 | Kessous-Elbaz et al. |
| 5,574,656 | A | 11/1996 | Agrafiotis et al. |
| 5,575,997 | A | 11/1996 | Leung et al. |
| 5,576,436 | A | 11/1996 | McCabe et al. |
| 5,578,079 | A | 11/1996 | Kamel et al. |
| 5,582,834 | A | 12/1996 | Leung et al. |
| 5,591,618 | A | 1/1997 | Chantry et al. |
| 5,597,699 | A | 1/1997 | Lanzara |
| 5,602,240 | A | 2/1997 | DeMesmaeker et al. |
| 5,625,048 | A | 4/1997 | Tsien et al. |
| 5,627,039 | A | 5/1997 | Pereira-Smith et al. |
| 5,658,783 | A | 8/1997 | Grandy et al. |
| 5,661,184 | A | 8/1997 | Helton et al. |
| 5,663,344 | A * | 9/1997 | Kozikowski et al. .......... 546/93 |
| 5,665,710 | A | 9/1997 | Rahman et al. |
| 5,670,113 | A | 9/1997 | Akong et al. |
| 5,684,711 | A | 11/1997 | Agrafiotis et al. |
| 5,700,673 | A | 12/1997 | McElroy et al. |
| 5,705,335 | A | 1/1998 | Hendry |
| 5,714,331 | A | 2/1998 | Buchardt et al. |
| 5,719,262 | A | 2/1998 | Buchardt et al. |
| 5,744,313 | A | 4/1998 | Williams et al. |
| 5,750,353 | A * | 5/1998 | Kopin et al. ............... 435/7.21 |
| 5,767,337 | A | 6/1998 | Roses et al. |
| 5,770,176 | A | 6/1998 | Nargessi |
| 5,777,079 | A | 7/1998 | Tsien et al. |
| 5,804,387 | A | 9/1998 | Cormack et al. |
| 5,821,067 | A | 10/1998 | Grandy et al. |
| 5,854,004 | A | 12/1998 | Czernilofsky et al. |
| 5,856,111 | A | 1/1999 | Ullrich et al. |
| 5,864,488 | A | 1/1999 | Issacs et al. |
| 5,874,219 | A | 2/1999 | Rava et al. |
| 5,882,944 | A * | 3/1999 | Sadee ........................ 436/501 |
| 5,891,646 | A | 4/1999 | Barak et al. |
| 5,912,122 | A | 6/1999 | Daggett et al. |
| 5,912,137 | A | 6/1999 | Tsien et al. |
| 5,912,138 | A | 6/1999 | Tonks et al. |
| 5,919,646 | A | 7/1999 | Okun et al. |
| 5,958,713 | A | 9/1999 | Thastrup et al. |
| 5,968,750 | A | 10/1999 | Zolotukhin et al. |
| 5,972,629 | A | 10/1999 | Niman |
| 5,972,639 | A | 10/1999 | Parandoosh |
| 5,987,390 | A | 11/1999 | Ladunga |
| 5,989,835 | A | 11/1999 | Dunlay et al. |
| 5,998,204 | A | 12/1999 | Tsien et al. |
| 6,007,986 | A | 12/1999 | Sadée |
| 6,017,496 | A | 1/2000 | Nova et al. |
| RE36,547 | E | 2/2000 | Crain et al. |
| 6,025,129 | A | 2/2000 | Nova et al. |
| 6,027,890 | A | 2/2000 | Ness et al. |
| 6,028,175 | A | 2/2000 | Grandy et al. |
| 6,051,386 | A | 4/2000 | Lerner et al. |
| 6,057,114 | A | 5/2000 | Akong et al. |
| 6,066,476 | A | 5/2000 | Tsien et al. |
| 6,087,115 | A | 7/2000 | Gershengorn et al. |
| 6,096,756 | A | 8/2000 | Crain et al. |
| 6,100,026 | A | 8/2000 | Nova et al. |
| 6,100,042 | A * | 8/2000 | Fowlkes et al. ............... 435/7.1 |
| 6,103,492 | A | 8/2000 | Yu |
| 6,107,324 | A | 8/2000 | Behan et al. |
| 6,110,693 | A | 8/2000 | Barak et al. |
| 6,124,102 | A | 9/2000 | Fodor et al. |
| 6,127,133 | A | 10/2000 | Akong et al. |
| 6,140,509 | A | 10/2000 | Behan et al. |
| 6,150,393 | A | 11/2000 | Behan et al. |
| 6,199,017 | B1 | 3/2001 | Tomonaga et al. |
| 6,203,987 | B1 | 3/2001 | Friend et al. |
| 6,219,622 | B1 | 4/2001 | Schmidt |
| 6,221,600 | B1 | 4/2001 | MacLeod et al. |
| 6,221,612 | B1 | 4/2001 | Knapp et al. |
| 6,255,059 | B1 * | 7/2001 | Klein et al. ................ 435/7.31 |
| 6,376,198 | B1 * | 4/2002 | Kopin et al. ................ 435/7.2 |

FOREIGN PATENT DOCUMENTS

| | | |
|---|---|---|
| WO | WO93/24510 A1 | 12/1993 |
| WO | WO94/16684 A1 | 8/1994 |
| WO | WO94/26764 A1 | 11/1994 |
| WO | WO95/21191 A1 | 8/1995 |
| WO | WO96/23810 A1 | 8/1996 |
| WO | WO96/23898 A1 | 8/1996 |
| WO | WO96/27027 A1 | 9/1996 |
| WO | WO96/27675 A1 | 9/1996 |
| WO | WO96/40062 A1 | 12/1996 |
| WO | WO97/11091 A1 | 3/1997 |
| WO | WO98/12310 A1 | 3/1998 |
| WO | WO98/44350 A1 | 10/1998 |
| WO | WO98/55635 A2 | 12/1998 |
| WO | WO99/66324 A2 | 12/1999 |
| WO | WO00/12704 A2 | 3/2000 |
| WO | WO01/58923 A2 | 8/2001 |
| WO | WO02/099381 A2 | 12/2002 |

OTHER PUBLICATIONS

Atlas, D., et al., Probing of β-adrenergic receptors by novel fluorescent β-adrenergic blockers, *Proceedings of the National Academy of Sciences*, vol. 74, No. 12, Dec. 1977, pp. 5290-5294, Proc. Natl Acad. Sci, USA.

Angers, S., et al., Detection of $β_2$-Adrenergic receptor dimerization in living cells using bioluminescence resonance energy transfer (*BRET*), *Proceedings of the National Academy of Sciences*, vol. 97, No. 7, Mar. 28, 2000, pp. 3684-3689, Proc. Natl Acad. Sci, USA.

Attramadal, H., et al., β-Arrestin2, a Novel Member of the Arrestin/β-Arrestin Gene Family, *Journal of Biological Chemistry*, vol. 267, No. 25, Sep. 5, 1992, pp. 17882-17890, The American Society for Biochemistry and Molecular Biology, Inc., USA.

Barak, L.S., et al., Constitutive arrestin-mediated desensitization of a human vasopressin receptor mutant associated with nephrogenic diabetes insipidus, published Dec. 26, 2000, *Proc. Natl. Acad. Sci USA Online*, and *Proceedings of the National Academy of Sciences*, vol. 98, No. 1, Jan. 2, 2001, pp. 93-98.

Barak, L.S., et al., Real-time Visualization of the Cellular Redistribution of G Protein-coupled Receptor Kinase 2 and β-arrestin 2 during Homologous Desensitization of the Substance P Receptor, *Journal of Biological Chemistry*, vol. 274, No. 11, Mar. 12, 1999, pp. 7565-7569, The American Society for Biochemistry and Molecular Biology, Inc., USA.

Barak, L.S., et al., A β-Arrestin/Green Fluorescent Protein Biosensor for Detecting G Protein-coupled Receptor Activation, *Journal of Biological Chemistry*, vol. 272, No. 44, Oct. 31, 1997, pp. 27497-27500, The American Society for Biochemistry and Molecular Biology, Inc., USA.

Barak, L.S. et al., Internet Trafficking and Surface Mobility of a Functionally Intact β2-Adrenergic Receptor-Green Fluorescent Protein Conjugate, *Molecular Pharmacology*, vol. 51, 1997, pp. 177-184.

Barak, L.S., et al., Characterization of a Green Fluorescent Protein Conjugated Beta2-Adrenergic Receptor, *Molecular Biology of the Cell* (supplement), Abstract #2484, vol. 7, p. 427a (Dec. 1996).

Barak, L.S., et al., The Conserved Seven-Transmembrane Sequence NP(X)2,3 Y of the G-Protein-Coupled Receptor Superfamily Regulates Multiple Properties of the $β_2$-Adrenergic Receptor, *Biochemistry*, vol. 34, No. 47, 1995, pp. 15407-15414.

Barak, L, et al., A Highly Conserved Tyrosine Residue in G Protein-coupled Receptors is Required for Agonist-mediated β2-Adrenergic Receptor Sequestration, *Journal of Biological Chemistry*, vol. 269, No. 4, Jan. 28, 1994, pp. 2790-2795.

Bardram, L., et al., Processing-Independent Radioimmunoanalysis: A General Analytical Principle Applied to Progastrin and its Products, *Anal Biochem*, vol. 175, pp. 537-543, 1988, Academic Press, Inc.

Benovic, J.L., et al., *Regulation of Adenylyl Cyclase-Coupled β-Adrenergic Receptors*, Annual Review Cell Biology, vol. 4, pp. 405-428, 1988, Annual Reviews, Inc.

Bohn, Laura M., et al., Enhanced Morphine Analgesia in Mice Lacking β-Arrestin2, *Science*, (Washington D.C.), vol. 286, No. 5449, Dec. 24, 1999, pp. 2495-2498.

Brady, III, C.E., Secretin Provocation Test in the Diagnosis of Zollinger-Ellison Syndrome, *The American Journal of Gastroenterology*, vol. 86, pp. 129-134, Feb. 1991, USA.

Bugat, R., et al., Gastric Mucosal Lesions Produced By Intravenous Infusion of Aspirin in Cats, *Gastroenterology*, vol. 71, pp. 754-759, Nov. 1976, USA.

Carey, K.L., et al., *Evidence Using a Green Fluorescent Protein-Glucocorticoid Receptor Chimera that the RAN/TC4 GTPase Mediates an Essential Function Independent of Nuclear Protein Import*, The Journal of Cell Biology, vol. 133, pp. 985-996, 1996, The Rockefeller University Press, USA.

Chalfie, M., et al., Green fluorescent protein as a Marker for Gene Expression, *Science*, vol. 263, pp. 802-805 (1994).

Chen, Jeannie, et al., Increased Susceptibility to Light Damage in an Arrestin Knockout Mouse Model of Oguchi Disease (Stationary Night Blindness), *Investigative Ophthalmology & Visual Science*, vol. 40, No. 12, Nov. 1999, pp. 2978-2982.

Cox, B.M., Mechanisms of Tolerance, *Opioids in Pain Control: Basic and Clinical Aspects*, Ch. 6, pp. 109-130 (1999). Cambridge University Press.

Cubitt, A., et al., Understanding, Improving and Using Green Fluorescent Proteins, *Trends in Biochemical Sciences*, pp. 448-455, Nov. 1995.

*Current Protocols in Molecular Biology*, vol. 1, Section II, Supplement 24, 6.3.1-6.3.6, 1993, John Wiley & Sons, N.Y.

Czerwinski, G., et al., Cytotoxic agents directed to peptide hormone receptors: Defining the requirements for a successful drug, *Proceedings of the National Academy of Sciences*, vol. 95, Sep. 1998, pp. 11520-11525, Proc. Natl. Acad. Sci, USA.

Daulhac, L., et al., Src-family Tyrosine Kinases in Activation of ERK-1 and p85/p110-phosphatidylinositol 3-Kinase by G/CCKs Receptors, *Journal of Biological Chemistry*, vol. 274, No. 29, Jul. 16, 1999, pp. 20657-20663, The American Society of Biochemistry and Molecular Biology, Inc., USA.

Drews, J., Drug Discovery: A Historical Perspective, *Science*, vol. 287, Mar. 17, 2000, pp. 1960-1964, American Association for the Advancement of Science, Washington, D.C.

Edkins, J.S., *On the Chemical Mechanism of Gastric Secretion*, Proc R Soc Lond [Biol], vol. 76, p. 376, 1905.

Ferguson, S.S.G., et al., G-protein-coupled receptor regulation: role of G-protein-coupled receptor kinases and arrestins, *Can. J. Physiol. Pharmacol.*, vol. 74, 1996, pp. 1095-1110, NRC, Canada.

Ferguson, S.S.G., et al., Role of Phosphorylation in Agonist-promoted β2-Adrenergic Receptor Sequestration, *Journal of Biological Chemistry*, vol. 270, No. 42, Oct. 20, 1995, pp. 24782-24789, The American Society for Biochemistry and Molecular Biology, Inc., USA.

Ferguson, S.S.G., et al., Molecualr Mechanisms of G Protein-Coupled Receptor Desensitization and Resensitization, *Life Sciences*, 62:17/18 1561-1565 (1998).

Ferguson, S.S.G. et al., Role of β-Arrestin in Mediating Agonist-Promoted G Protein-Coupled Receptor Internalization, *Science*, vol. 271, pp. 363-366 (1996).

Ganguli, P.C., et al., Radioimmunoassay of Plasma-Gastrin In Pernicious Anaemia, Achlorhydria Without Pernicious Anaemia, Hypochlorhydria, and in Controls, *The Lancet*, vol. 1, pp. 155-158, Jan. 23, 1971.

Goodman, Jr. O.B., et al., β-Arrestin acts as a clathrin adaptor in endocytosis of the $β_2$-adrenergic receptor, *Nature*, vol. 383, pp. 447-450, Oct. 3, 1996.

Grady, E., et al., Mechanisms Attenuating Cellular Responses to Neuropeptides: Extracellular Degradation of Ligands and Desensitization of Receptors, *The Journal of Investigative Dermatology Symposium Proceedings*, vol. 21, No. 1, pp. 69-75, Aug. 1997, The Society of Investigative Dermatology, Inc.

Gregory, R.A., et al., The constitution and properties of two gastrins extracted from hog antral mucosa, *Gut*, vol. 5, pp. 103-117, 1964.

Grisshammer, R., et al., Expression of rat NK-2 (neurokinin A) receptor in *E. coli*, *Receptor Channels*, vol. 2, pp. 295-302 (1994) Abstract.

Grisshammer, R., et al., Expression of a rat neurotensin receptor in *Escherichia coli*, *Biochem. J.*, vol. 295, pp. 571-576, Oct. 1993, Abstract.

Gurevich, V.V., et al., Arrestin Interactions with G Protein-coupled Receptors, *Journal of Biological Chemistry*, vol. 270, No. 2, pp. 720-731, 1995, The American Society for Biochemistry and Molecular Biology, Inc., USA.

Gurevich, V.V., et al., Binding of Wild Type and Chimeric Arrestins to the m2 Muscarinic Cholinergic Receptor, *Journal of Biological Chemistry*, vol. 268, No. 23, pp. 16879-16882, 1993, The American Society for Biochemistry and Molecular Biology, Inc., USA.

Gurevich, V.V., et al., Visual Arrestin Interaction with Rhodopsin, *Journal of Biological Chemistry*, vol. 268, No. 16, pp. 11628-11638, 1993, The American Society for Biochemistry and Molecular Biology, Inc., USA.

Hanninen, A.L., et al., Expression in *Escherichia coli* of rat neurotensin receptor fused to membrane proteins from the membrane-containing bacteriophage PRD1 *Biol. Chem. Hoppe Sevler*, vol. 375, pp. 833-836 (1994) Abstract.

Harada, A., et al., Altered microtubule organization in small-calibre axons of mice lacking tau protein, *Nature*, vol. 369, No. 6480, pp. 488-491, Jun. 9, 1994, Macmillian Magazines, Ltd., London.

Harden, T.K., Agonist-induced Desensitization of the β-Adrenergic Receptor-linked Adenylate Cyclase, *Pharmacological Reviews*, vol. 35, No. 1, pp. 5-32, 1983, USA.

Harris, E., et al., *Protein Purification Methods*, Oxford University Press, New York, pp. 12-18 (1990).

Hausdorff, W.P., et al., A Mutation of the $β_2$-Adrenergic Receptor Impairs Agonist Activation of Adenylyl Cylclase Without Affecting High Affinity Agonist Binding, *Journal of Biological Chemistry*, vol. 265, No. 3, Jan. 25, 1990, pp. 1388-1393, The American Society for Biochemistry and Molecular Biology, Inc. USA.

Heim, R., et al., Wavelength mutations and posttranslational autoxidation of green fluorescent protein, *Proceedings of the National Academy of Sciences*, USA, vol. 91, No. 26, pp. 12501-12504, 1994.

Hersey, S.J., et al., Gastric Acid Secretion, *Physiological Reviews*, vol. 75, No. 1, 1995, pp. 155-189, USA.

Htun, H., et al., Visualization of glucocorticoid Receptor Translocation and Intranuclear Organization in Living Cells with a Green Fluorescent Protein Chimera, *Proceedings of the National Academy of Sciences*, May 1996, vol. 93, pp. 4845-4850, USA.

Hughes, J., et al., Development of a class of selective cholecystokinin type B receptor antagonists having potent anxiolytic activity, *Proceedings of the National Academy of Sciences*, vol. 87, Sep. 1990, pp. 6728-6732, Proc. Natl. Acad. Sci, USA.

Joshi, S.N., et al., Gastrin and Colon Cancer: A Unifying Hypothesis, *Digestive Diseases*, vol. 14, pp. 334-344, 1996.

Kaether, C., et al., Visualization of protein transport along the secretory pathway using green fluorescent protein, *FEBS Letters*, vol. 369, pp. 267-271, 1995.

Keith, D.E., et al., Morphine Activates Opioid Receptors without Causing their Rapid Internalization, *Journal of Biological Chemistry*, vol. 271, No. 32, pp. 19021-19024, 1996, American Society for Biochemistry and Molecular Biology, Inc., USA.

Kim, K.M., et al., Differential Regulation of the Dopamine $D_2$ and $D_3$ Receptors by G Protein-coupled Receptor Kinases and β-arrestins, published Jul. 25, 2001, JBC Papers in Press, and *Journal of Biological Chemistry*, vol. 276, No. 40, Oct. 5, 2001, pp. 37409-37414, American Society for Biochemistry and Molecular Biology, Inc., USA.

Klein, U., et al., A Novel Interaction between Adrenergic Receptors and the α-Subunit of Eukaryotic Initiation Factor 2B, *Journal of Biological Chemistry*, vol. 272, No. 31, Aug. 1, 1997, pp. 19099-19102, American Society for Biochemistry and Molecular Biology, Inc., USA.

Kopin, A.S., et al., Expression cloning and characterization of the canine parietal cell gastrin receptor, *Proceedings of the National Academy of Sciences*, vol. 89, Apr. 1992, pp. 3605-3609, Proc. Natl. Acad. Sci, USA.

Kovoor, Abraham, et al., μ and δ Opioid Receptors Are Differentially Desensitized by the Coexpression of β-Adrenergic Receptor Kinase 2 and β-Arrestin 2 in Xenopus Oocytes, *The Journal of Biological Chemistry* (U.S.A.), vol. 272, No. 44, Oct. 31, 1997, pp. 27605-27611.

Laporte, S. A., et al., The Interaction of β-Arrestin with the AP-2 Adaptor is Required for the Clustering of $\beta_2$ Adrenergic Receptor into Clathrin-coated Pits, published Apr. 17, 2000, JBC Papers in Press, and *Journal of Biological Chemistry*, vol. 275, No. 30, Jul. 28, 2000, pp. 23120-23126, The American Society for Biochemistry and Molecular Biology, Inc., USA.

Laporte, S.A., et al., The $\beta_2$-Adrenergic Receptor/Barrestin complex recruits the clathrin adaptor AP-2 during endocytosis, *Proceedings of the National Academy of Sciences*, vol. 96, No. 7, Mar. 30, 1999, pp. 3712-3717, Proc. Natl. Acad. Sci. USA.

Lee, Y.M., et al., The Human Brain Cholecystokinin-B/Gastrin Receptor, *Journal of Biological Chemistry*, vol. 268, No. 11, Apr. 15, 1993, pp. 8164-8169, The American Society of Biochemistry and Molecular Biology, Inc., USA.

Lefkowitz, et al., Adenylate Cyclase-coupled Beta-Adrenergic Receptors: Structure and Mechanisms of Activation and Desensitization, *Ann. Rev. Biochem*, vol. 52, pp. 159-186, 1983, Annual Reviews Inc.

Lefkowitz, R.J., G Protein-coupled Receptors, III. New Roles For Receptor Kinases and β-arrestins in Receptor Signaling and Desensitization, *Journal of Biological Chemistry*, vol. 273, No. 30, Jul. 24, 1998, pp. 18677-18680, The American Society of Biochemistry and Molecular Biology, Inc., USA.

Leopoldt, D., et al., Gβγ Stimulates Phosphoinositide 3-Kinase-γ by Direct Interaction with Two Domains of the Catalytic p110 Subunit, *Journal of Biological Chemistry* vol. 273, No. 12, Mar. 20, 1998, pp. 7024-7029.

Lohse, M., et al., β-arrestin: A Protein That Regulates β-Adrenergic Receptor Function, *Science*, vol. 248, pp. 1547-1550, Jun. 22, 1990.

Luttrell, L.M., et al., Barrestin-Dependent Formation of $\beta_2$ Adrenergic Receptor-Src Protein Kinase Complexes, vol. 283, Jan. 29, 1999, *Science*, pp. 655-661, USA.

Mantyh, C.R., et al., Localization of Cholecystokinin A and Cholecystokinin B/Gastrin Receptors in the Canine Upper Gastrointestinal Tract, *Gastroenterology*, vol. 107, 1994, pp. 1019-1030, American Gastroenterological Association, USA.

Mathier, Michael, A. et al., Enhanced Left Ventricular Contractile Responses to Acute β-Adrenergic Stimulation in a β-Arrestin 1 Knockout Mouse, *Circulation*, 70th Scientific Sessions of the American Heart Association, Orlando, Florida, US, vol. 96, No. 8, Suppl., 1997, p. 1445.

McConalogue, K., et al., Activation and Internalization of the μ-opioid Receptor by the Newly Discovered Endogenous Agonists, Endomorphin-1 and Endomorphin-2, *Neuroscience*, vol. 90, No. 3, pp. 1051-1059, 1999, Elsevier Science Ltd., Great Britain.

McConalogue, K., et al., Cellular And Subcellular Localization Of G-Protein Receptor Kinases, Arrestins And G-Proteins: Implications For Receptor Regulation, *Gastroenterology*, vol. 110, No. 4: 1 Supplement: A1098 AGA Abstracts, 1996.

McConalogue, K., et al., G Protein-Coupled Receptors in Gastrointestinal Physiology II. Regulation of neuropeptide receptors in enteric neurons, *American J. Physiol.*, vol. 274, pp. G792-G796, 1998, American Physiological Society.

McConalogue, K., et al., Substance P-induced Trafficking of β-arrestins, *Journal of Biological Chemistry*, vol. 274, No. 23, pp. 16257-16268, Jun. 4, 1999, The American Society for Biochemistry and Molecular Biology, Inc., USA.

Ménard, L., et al., Members of the G Protein-Coupled Receptor Kinase Family That Phosphorylate the $\beta_2$-Adrenergic Receptor Facilitate Sequestration, *Biochemistry*, vol. 35, No. 13, pp. 4155-4160 (1996).

Ménard, L., et al., Synergistic Regulation of $\beta_2$-Adrenertic Receptor Sequestration: Intracellular Complement of $\beta_2$-Adrenergic Receptor Kinase and β-Arrestin Determine Kinetics of Internalization, *Molecular Pharmacology*, vol. 51, No. 5, May 1997, pp. 800-808, The American Society for Pharmacology and Experimental Therapeutics.

Mhaouty-Kodja, S., et al., Constitutively Active Alpha-1b Adrenergic Receptor Mutants Display Different Phosphorylation and Internalization Features, *Molecular Pharmacology*, vol. 55, No. 2, Feb. 1999, pp. 339-347, The American Society for Pharmacology and Experimental Therapeutics.

Morise, H., et al., Intermolecular Energy Transfer in the Bioluminescent System of Aequorea, *Biochemistry*, vol. 13, No. 12, pp. 2656-2662, 1974.

Naga Prasad, S.V., et al., Agonist-dependent Recruitment of Phosphoinositide 3-Kinase to the Membrane by β-Adrenergic Receptor Kinase 1, published Mar. 19, 2001, JBC Papers in Press, and *Journal of Biological Chemistry*, vol. 276, No. 22, Jun. 1, 2001, pp. 18953-18959.

Naga Prasad, S.V., et al., Gβγ-dependent Phosphoinositide 3-Kinase Activation in Hearts with in Vivo Pressure Overload Hypertrophy, *Journal of Biological Chemistry*, vol. 275, No. 7, Feb. 18, 2000, pp. 4693-4698.

Nelson, S., et al., Characterization of an Intrinsically Fluorescent Gonadotropin-Releasing Hormone Receptor and Effects of Ligand Binding on Receptor Lateral Diffusion, *Endocrinology*, vol. 140, No. 2, 1999, pp. 950-957, The Endocrine Society, USA.

Nestler, E.J., Under Siege: The Brain on Opiates, *Neuron*, vol. 16, pp. 897-900, May 1996, Cell Press.

Neuwald, A.F. et al., Heat Repeats associated with Condensins, Cohesins, and Other Complexes Involved in Chromosome Related Functions, *Genome Research*, Cold Spring Laboratory Press, vol. 10, 2000, pp. 1445-1452.

Oakley, R.H., et al., Molecular Determinants Underlying the Formation of Stable Intracellular G Protein-coupled Receptor—β-Arrestin Complexes after Receptor Endocytosis, published Mar. 9, 2001, JBC Papers in Press, and *Journal of Biological Chemistry*, vol. 276, No. 22, Jun. 1, 2001, pp. 19452-19460, The American Society for Biochemistry and Molecular Biology, Inc., USA.

Oakley, R.H., et al., Differential Affinities of Visual Arrestin, β-Arrestin 1, and β-Arrestin2 for G Protein-coupled Receptors Delineate Two Major Classes of Receptors, published Mar. 29, 2000, JBC Papers in Press, and *Journal of Biological Chemistry*, vol. 275, No. 22, Jun. 2, 2000, pp. 17201-17210, The American Society for Biochemistry and Molecular Biology, Inc., USA.

Oakley, R.H., et al., Association of β-Arrestin with G Protein-coupled Receptors during Clathrin-mediated Endocytosis Dictates the Profile of Receptor Resensitization, *Journal of Biological Chemistry*, vol. 274, No. 45, Nov. 5, 1999, pp. 32248-32257, The American Society for Biochemistry and Molecular Biology, Inc., USA.

Olson, K.R. et al., Analysis of MAP 4 Function in Living Cells Using Green Fluorescent Protein (GFP) Chimeras, *Journal of Cell Biology*, 1995, vol. 130, No. 3, pp. 639-650, The Rockefeller University Press.

Ormö, M., et al., Crystal Structure of the Aequorea victoria Green Fluorescent Proteins, *Science*, vol. 273, pp. 1392-1395, Sep. 6, 1996.

Pisegna, J.R., et al., Molecular Cloning of the Human Brain and Gastric Cholecystokinin Receptor: Structure, Functional Expression and Chromosomal Localization, *Biochemical And Biophysical Research Communications*, vol. 189, No. 1, Nov. 30, 1992, pp. 296-303, Academic Press, USA.

Pitcher, J.A., et al., G Protein-coupled Receptor Kinases, *Annual Review of Biochemistry*, vol. 67, 1998, pp. 653-692, Annual Reviews, USA.

Prasher, D. C., et al., Primary structure of the Aequorea victoria green-fluorescent protein, *Gene*, vol. 111, pp. 229-233, 1992, Elsevier Science Publishers B.V.

Probst, W.C., et al., Sequence Alignment of the G-Protein Coupled Receptor Superfamily, *DNA and Cell Biology*, vol. 11, No. 1, Jan. & Feb. 1992, pp. 1-20, Mary Ann Liebert, Inc. Publishers.

Rehfeld, J.F., et al., Structure of the Bioactive Gastrins, Chapter 1, 1993, pp. 1-14, *Gastrin*, Raven Press, New York, USA.

Rehfeld, J.F., The New Biology of Gastrointestinal Hormones, *Physiological Reviews*, vol. 78, No. 4, Oct. 1998, pp. 1087-1108, The American Physiological Society, USA.

Sadeghi, H.M., et al., Maturation of Receptor Proteins in Eukaryotic Expression Systems, *Journal of Receptor & Signal Transduction Research*, vol. 17, No. 1-3, 1997, pp. 433-445, Marcel Dekker, Inc., USA.

Sadeghi, H., et al., O-Glycosylation of the V2 vasopressin receptor, *Glycobiology*, vol. 9, No. 7, pp. 731-737, 1999, Oxford University Press, Printed by the Sheridan Press, USA.

Schöneberg, T., et al., Functional rescue of mutant V2 vasopressin receptors causing nephrogenic diabetes insipidus by a co-expressed receptor polypeptide, *Embo Journal*, vol. 15, No. 6, pp. 1283-1291, 1996, Oxford University Press.

Schöneberg, T., et al., V2 Vasopressin Receptor Dysfunction in Nephrogenic Diabetes Insipidus Caused by Different Molecular Mechanisms, *Human Mutation*, vol. 12, No. 3, pp. 196-205, 1998, Wiley-Liss. Inc.

Schulz, Rüdiger, et al., Phosducin, β-arrestin and Opioid receptor migration, *European Journal of Pharmacology*, vol. 375, No. 1-3, Jun. 30, 1999, pp. 349-357, Elsevier Science B.V.

Shi, W., et al., Rhodopsin Arginine-135 Mutants Are Phosphorylated by Rhodopsin Kinase and Bind Arrestin in the Absence of 11 -cis-Retinal, *Biochemistry*, vol. 37, pp. 4869-4874, 1998, American Chemical Society, Washington, D.C.

Shetzline, M.A., et al., A Role for Receptor Kinases in the Regulation of Class II G Protein-coupled Receptors: Phosphorylation and Desensitization of the Secretin Receptor, *Journal of Biological Chemistry*, vol. 273, No. 12, Mar. 20, 1998, pp. 6756-6762, The American Society for Biochemistry and Molecular Biology, Inc., USA.

Sloas, D.D., et al., A Nongastrin Malignant Ampullary Tumor Causing Gastric Acid and Pepsin Hypersecretion, *J. Clin Gastroenterol.* vol. 12(5), 1990, pp. 573-578, Raven Press, Ltd., New York, USA.

Smith, A.J., et al., CCK-B Receptor-Mediated Stimulation of Polyphosphoinositide Turnover in $GH_3$ Pituitary Cells in Response to Cholecystokinin and Pentagastrin, *Life Sciences*, vol. 58, No. 11, 1996, pp. 883-895, Elsevier Science Inc., USA.

Sterne-Marr, R., et al., Regulation of G Protein-coupled Receptors by Receptor Kinases and Arrestins, *Vitamins and Hormones*, vol. 51, 1995, pp. 193-234, Academic Press, Inc.

Sternini, Catia, et al., Agonist-selective endocytosis of μ opiod receptor by neurons in vivo, *Proceedings of the National Academy of Sciences USA*, vol. 93, pp. 9241-9246 (Aug. 1996).

Tucker, J., et al., Purification of a rat neurotensin receptor expressed in *Escherichia coli, Biochem. J.* vol. 317, 1996, pp. 891-899, Printed in Great Britain.

Valette, F., et al., Construction of mutant and chimeric genes using the polymerase chain reaction, *Nucleic Acids Research*, vol. 17, No. 2, pp. 723-733, 1989, IRL Press.

Van Solinge, W.W., et al., Radioimmunoassay for Sequence 38-54 of Human Progastrin: Increased Diagnostic Specificity of Gastrin-Cell Disease, *Clinica Chimica Acta*, vol. 192, 1990, pp. 35-46, Elsevier Science Publishers B.V.

Walker, J.K.L., et al., Properties of Secretin Receptor Internalization Differ from Those of the $β_2$-Adrenergic Receptor, *Journal of Biological Chemistry*, vol. 274, No. 44, Oct. 29, 1999, pp. 31515-31523, The American Society for Biochemistry and Molecular Biology, Inc., USA.

Wank, S.A., Cholecystokinin Receptors, *Am. J. Physiol.* vol. 269, 1995, pp. G628-G646.

Wank, S.A., et al., Brain and Gastrointestinal Cholecystokinin Receptor Family: Structure and Functional Expression, *Proceedings of the National Academy of Sciences*, vol. 89, Sep. 1992, pp. 8691-8695, Proc. Natl. Acad. Sci, USA.

Ward, W.W., et al., Spectrophotometric Identity of the Energy Transfer Chromophores in Renilla and Aequorea Green-Fluorescent Proteins, *Photochemistry and Photobiology*, 1980, vol. 31, pp. 611-615, Pergamon Press, Ltd., Great Britain.

Whistler, Jennifer, L., et al., Morphine-activated opioid receptors elude desensitization by β-arrestin, *Proceedings of the National Academy of Science of the United States*, vol. 95, No. 17, Aug. 18, 1998, pp. 9914-9919.

Wolfe, M.M., et al., Zollinger-Ellison Syndrome Associated with Persistently Normal Fasting Serum Gastrin Concentrations, *Annals of Internal Medicine*, vol. 103, 1985, pp. 215-217, USA.

Wolfe, M.M., et al., Zollinger-Ellison Syndrome, Current Concepts in Diagnosis and Management, *New England Journal of Medicine*, vol. 317, Nov. 5, 1987, pp. 1200-1209, USA.

Yokoe, H., et al., Spatial Dynamics of GFP-tagged proteins investigated by local fluorescence enhancement, *Nature Biotechnology*, vol. 14, pp. 1252-1256 (Oct. 1996).

Yu, Yunkai, et al., μ Opiod Receptor Phosphorylation, Desensitization, and Ligand Efficacy, *Journal of Biological Chemistry*, vol. 272, No. 46, pp. 28869-28874 (1997).

Zhang, J., et al., Cellular Trafficking of G Protein-coupled Receptor/β-Arrestin Endocytic Complexes, *Journal of Biological Chemistry*, vol. 274, No. 16, Apr. 16, 1999, pp. 10999-11006, The American Society for Biochemistry and Molecular Biology, Inc., USA.

Zhang, J. et al., Role for G protein-coupled receptor kinase in agonist-specific regulation of μ-opiod receptor responsiveness, *Proceedings of the National Academy of Sciences, USA*, vol. 95, pp. 7157-7162 (Jun. 1998).

Zhang, J., et al, A Central Role for β-Arrestins and Clathrin-coated Vesicle-mediated Endocytosis in $β_2$-Adrenergic Receptor Resensitization, *Journal of Biological Chemistry*, vol. 272, No. 43, Oct. 24, 1997, pp. 27005-27014, The American Society for Biochemistry and Molecular Biology, Inc., USA.

Zhang, J., et al., Dynamin and β-Arrestin Reveal Distinct Mechanisms for G Protein-coupled Receptor Internalization, *Journal of Biological Chemistry*, vol. 271, No. 31, pp. 18302-18305, 1996, USA.

Zimmer, T., et al., Brief Report: A Duodenal Gastrinoma in a Patient with Diarrhea and Normal Serum Gastrin Concentrations, *New England Journal of Medicine*, vol. 333, Sep. 7, 1995, pp. 634-636, USA.

Zuckerman, R., et al., Sites of arrestin action during the quench phenomenon in retinal rods, *Federation of European Biochemical Society*, vol. 238, No. 2, pp. 379-384, Elsevier Science Publishers, 1988.

\* cited by examiner

FIG. 1A

Human G Protein Coupled Receptor Family
(Receptors known as of January, 1999)

| CLASS | LIGAND | NUMBER | TISSUE | PHYSIOLOGY | THERAPEUTICS |
|---|---|---|---|---|---|
| Class I Rhodopsin like | | | | | |
| | • Amine | | | | |
| | • Acetylcholine (muscarinic & nicotinic) | 5 | Brain, Nerves, Heart | Neurotransmitter | Acuity, Alzheimer's |
| | • Adrenoceptors | | | | |
| | • Alpha Adrenoceptors | 6 | Brain, Kidney, Lung | Gluconeogenesis | Diabetes, Cardiovascular |
| | • Beta Adrenoceptors | 3 | Kidney, Heart | Muscle Contraction | Cardiovascular, Respiratory |
| | • Dopamine | 5 | Brain, Kidney, GI | Neurotransmitter | Cardiovascular, Parkinson's |
| | • Histamine | 2 | Vascular, Heart, Brain | Vascular Permeability | Anti-inflammatory, Ulcers |
| | • Serotonin (5-HT) | 16 | Most Tissues | Neurotransmitter | Depression, Insomnia, Analgesic |
| | • Peptide | | | | |
| | • Angiotensin | 2 | Vascular, Liver, Kidney | Vasoconstriction | Cardiovascular, Endocrine |
| | • Bradykinin | 1 | Liver, Blood | Vasodilation, | Anti-inflammatory, Asthma |
| | • C5a anaphylatoxin | 1 | Blood | Immune System | Anti-inflammatory |
| | • Fmet-leu-phe | 3 | Blood | Chemoattractant | Anti-inflammatory |
| | • Interleukin-8 | 1 | Blood | Chemoattractant | Anti-inflammatory |
| | • Chemokine | 6 | Blood | Chemoattractant | Anti-inflammatory |
| | • Orexin | 2 | Brain | Fat Metabolism | Obesity |
| | • Nociceptin | 1 | Brain | Bronchodilator, Pain | Airway Diseases, Anesthetic |
| | • CCK (Gastrin) | 2 | Gastrointestinal | Motility, Fat Absorption | Gastrointestinal, Obesity, Parkinson's |
| | • Endothelin | 2 | Heart, Bronchus, Brain | Muscle Contraction | Cardiovascular, Respiratory |
| | • Melanocortin | 5 | Kidney, Brain | Metabolic Regulation | Anti-inflammatory, Analgesics |
| | • Neuropeptide Y | 5 | Nerves, Intestine, Blood | Neurotransmitter | Behavior, Memory, Cardiovascular |
| | • Neurotensin | 1 | Brain, | CNS | Cardiovascular, Analgesic |
| | • Opioid | 3 | Brain, | CNS | Depression, Analgesic |
| | • Somatostatin | 5 | Brain, Gastrointestinal | Neurotransmitter | Oncology, Alzheimer's |

FIG. 1B

| | | | |
|---|---|---|---|
| •Tachykinin (Substance P, NKA₁) | 3 | Brain Nerves | Neurohormone | Depression, Analgesic |
| •Thrombin | 3 | Platelets, Blood Vessels | Coagulation | Anti-coagulant, Anti-inflammatory |
| •Vasopressin-like | 4 | Arteries, Heart, Bladder | Water Balance | Anti-diuretic, Diabetic Complications |
| •Galanin | 1 | Brain, Pancreas | Neurotransmitter | Analgesics, Alzheimer's |
| •Hormone protein | | | | |
| •Follicle stimulating hormone | 1 | Ovary, Testis | Endocrine | Infertility |
| •Lutropin-choriogonadotropic | 1 | Ovary, Testis | Endocrine | Infertility |
| •Thyrotropin | 1 | Thyroid | Endocrine | Thyroidism, Metabolism |
| •(Rhod)opsin | | | | |
| •Opsin | 5 | Eye | Photoreception | Ophthalmic Diseases |
| •Olfactory | 4(~1000) | Nose | Smell | Olfactory Diseases |
| •Prostanoid | | | | |
| •Prostaglandin | 5 | Arterial, Gastrointestinal | Vasodilation, Pain | Cardiovascular, Analgesic |
| •Lysophosphatidic Acid | 2 | Vessels, Heart, Lung | Inflammation | Cancer, Anti-Inflammatory |
| •Sphingosine-1-phosphate | 2 | Most Cells | Cell proliferation | Cancer |
| •Leukotriene | 1 | White Blood Cells, Bronchus | Inflammation | Asthma, Rheumatoid Arthritis |
| •Prostacyclin | 1 | Arterial, Gastrointestinal | Platelet Regulation | Cardiovascular |
| •Thromboxane | 1 | Arterial, Bronchus | Vasoconstriction | Cardiovascular, Respiratory |
| •Nucleotide-like | | | | |
| •Adenosine | 4 | Vascular, Bronchus | Multiple Effects | Cardiovascular, Respiratory |
| •Purinoceptors | 4 | Vascular, Platelets | Relaxes Muscle | Cardiovascular, Respiratory |
| •Cannabis | 2 | Brain | Sensory Perception | Analgesics, Memory |
| •Platelet activating factor | 1 | Most Peripheral Tissues | Inflammation | Anti-inflammatory, Anti-asthmatic |
| •Gonadotropin-releasing hormone like | | | | |
| •Gonadotropin-releasing hormone | 1 | Reproductive Organs, Pituitary | Reproduction | Prostate Cancer, Endometriosis |
| •Thyrotropin-releasing hormone | 1 | Pituitary, Brain | Thyroid Regulation | Metabolic Regulation |
| •Growth hormone-inhibiting factor | 1 | Gastrointestinal | Neuroendocrine | Oncology, Alzheimer's |
| •Melatonin | 1 | Brain, Eye, Pituitary | Neuroendocrine | Regulation of Circadian Cycle |

FIG. 1C

- Class II
  Secretin like

| | | | |
|---|---|---|---|
| •Secretin | 1 | Gastrointestinal, Heart | Digestion | Obesity, Gastrointestinal |
| •Calcitonin | 1 | Bone, Brain | Calcium Resorption | Osteoporosis |
| •Corticotropin releasing factor/urocortin | 1 | Adrenal, Vascular, Brain | Neuroendocrine | Stress, Mood, Obesity |
| •Gastric inhibitory peptide (GIP) | 1 | Adrenals, Fat Cells | Sugar/Fat Metabolism | Diabetes, Obesity |
| •Glucagon | 1 | Liver, Fat Cells, Heart | Gluconeogenesis | Cardiovascular |
| •Glucagon-like Peptide 1 (GLP-1) | 1 | Pancreas, Stomach, Lung | Gluconeogenesis | Cardiovascular, Diabetes, Obesity |
| •Growth hormone-releasing hormone | 1 | Brain | Neuroendocrine | Growth Regulation |
| •Parathyroid hormone | 1 | Bone, Kidney | Calcium Regulation | Osteoporosis |
| •PACAP | 1 | Brain, Pancreas, Adrenals | Metabolism | Metabolic Regulation |
| •Vasoactive intestinal polypeptide (VIP) | 1 | Gastrointestinal | Motility | Gastrointestinal |

- Class III

| | | | |
|---|---|---|---|
| •Metabotropic Glutamate | 7 | Brain | Sensory Perception | Hearing, Vision |
| •GABA$_B$ | 1 | Brain | Neurotransmitter | Mood Disorders |
| •Extracellular Calcium Sensing | 1 | Parathyroid, Kidney, GI Tract | Calcium Regulation | Cataracts, GI Tumors |

FIG. 2

G Protein-Coupled Receptors that Translocate Arrestins

| Adrenergic Receptors | Serotonergic Receptors | Others | |
|---|---|---|---|
| alpha 1B | 5HT1A | FMLP | f-Met-Leu-Phe Receptor |
| alpha 2A | 5HT2A | AT1AR | Angiotensin Receptor |
| alpha 2B | Chemokine Receptors | CRFR | Corticotropin Releasing Factor |
| alpha 2C | CXCR2 | ETAR | Endothelin A Receptor |
| beta1 | CXCR4 | NK-1 | Substance P Receptor |
| beta2 | Edg Receptors | NTR | Neurotensin Receptor |
| Dopaminergic Receptors | Edg1 | OAMB | Octopamine Receptor (Drosophila) |
| D1A | Edg2 | OXY | Oxytocin Receptor |
| D1B | Edg3 | TRHR | Thyroid Releasing Hormone Receptor |
| D2 | Edg5 | V2 | Vasopressin Receptor |
| D3 | GI Receptors | | |
| D4 | CCK- A and B | | |
| Muscarinic Receptors | glucagon | | |
| m1 | secretin | | |
| m2 | VIP | | |
| m3 | Prostaglandin Receptors | | |
| m4 | | | |
| | EP3 | | |
| Opioid Receptors | | | |
| Mor1 | EP4 | | |
| Delta | | | |

FIG. 3A homo sapiens muscarinic receptor 1
Amino acid sequence
Accession NM_000738
MNTSAPPAVSPNITVLAPGKGPWQVAFIGITTGLLSLATVTGNL
LVLISFKVNTELKTVNNYFLLSLACADLIIGTFSMNLYTTYLLMGHWALGTLACD
ALDYVASNASVMNLLLISFDRYFSVTRPLSYRAKRTPRRAALMIGLAWLVSFVLWAPA
ILFWQYLVGERTMLAGQCYIQFLSQPIITFGTAMAAFYLPVTVMCTLYWRIYRETENR
ARELAALQGSETPGKGGGSSSSSERSQPGAEGSPETPPGRCCRCCRAPRLLQAYSWKE
EEEEDEGSMESLTSSEGEEPGSEVVIKMPMVDPEAQAPTKQPPRSSPNTVKRPTKKGR
DRAGKGQKPRGKEQLAKRKTFSLVKEKKAARTLSAILLAFILTWTPYNIMVLVSTFCK
DCVPETLWELGYWLCYVNSTINPMCYALCNKAFRDTFRLLLLCRWDKRRWRKIPKRPG
SVHRTPSRQC
SEQ ID NO: 1 homo sapiens muscarinic receptor 1 (gene CHRM1, CDS 1..1383)
Nucleic acid sequence
```
   1 atgaacactt cagccccacc tgctgtcagc cccaacatca ccgtcctggc accaggaaag
  61 ggtccctggc aagtggcctt cattgggatc accacgggcc tcctgtcgct agccacagtg
 121 acaggcaacc tgctggtact catctctttc aaggtcaaca cggagctcaa gacagtcaat
 181 aactacttcc tgctgagcct ggcctgtgct gacctcatca tcggtacctt ctccatgaac
 241 ctctatacca cgtacctgct catgggccac tgggctctgg gcacgctggc ttgtgacctc
 301 tggctggccc tggactatgt ggccagcaat gcctccgtca tgaatctgct gctcatcagc
 361 tttgaccgct acttctccgt gactcggccc ctgagctacc gtgccaagcg cacaccccgc
 421 cgggcagctc tgatgatcgg cctggctgg ctggtttcct tgtgctctg ggccccagcc
 481 atcctcttct ggcagtacct ggtagggag cggacgatgc tagctgggca gtgctacatc
 541 cagttcctct cccagcccat catcaccttt ggcacagcca tggctgcctt ctacctccct
 601 gtcacagtca tgtgcacgct ctactggcgc atctaccggg agacagagaa ccgagcacgg
 661 gagctggcag cccttcaggg ctccgagacg ccaggcaaag ggggtggcag cagcagcagc
 721 tcagagaggt ctcagccagg ggctgagggc tcaccagaga ctcctccagg ccgctgctgt
 781 cgctgctgcc gggcccccag gctgctgcag gcctacagct ggaaggaaga agaggaagag
 841 gacgaaggct ccatggagtc cctcacatcc tcagagggag aggagcctgg ctccgaagtg
 901 gtgatcaaga tgccaatggt ggaccccgag gcacaggccc caccaagca gccccacgg
 961 agctccccaa atacagtcaa gaggccgact aagaagggc gtgatcgagc tggcaagggc
1021 cagaagcccc gtggaaagga gcagctggcc aagcggaaga ccttctcgct ggtcaaggag
1081 aagaaggcgg ctcggaccct gagtgccatc ctcctggcct tcatcctcac ctggacaccg
1141 tacaacatca tggtgctggt gtccaccttc tgcaaggact gtgttccga gaccctgtgg
1201 gagctggct actggctgtg ctacgtcaac agcaccatca ccccatgtg ctacgcactc
1261 tgcaacaaag ccttccggga cacctttcgc ctgctgctgc tttgccgctg ggacaagaga
1321 cgctggcgca agatccccaa gcgccctggc tccgtgcacc gcactccctc cgccaatgc
1381 tga
```
SEQ ID NO: 2

FIG. 3B homo sapiens muscarinic receptor 2
Amino acid sequence
Accession NM_000739
MNNSTNSSNNSLALTSPYKTFEVVFIVLVAGSLSLVTIIGNILV
MVSIKVNRHLQTVNNYFLFSLACADLIIGVFSMNLYTLYTVIGYWPLGPVVCDLWLAL
DYVVSNASVMNLLIISFDRYFCVTKPLTYPVKRTTKMAGMMIAAAWVLSFILWAPAIL
FWQFIVGVRTVEDGECYIQFFSNAAVTFGTAIAAFYLPVIIMTVLYWHISRASKSRIK
KDKKEPVANQDPVSPSLVQGRIVKPNNNNMPSSDDGLEHNKIQNGKAPRDPVTENCVQ
GEEKESSNDSTSVSAVASNMRDDEITQDENTVSTSLGHSKDENSKQTCIRIGTKTPKS
DSCTPTNTTVEVVGSSGQNGDEKQNIVARKIVKMTKQPAKKKPPPSREKKVTRTILAI
LLAFIITWAPYNVMVLINTFCAPCIPNTVWTIGYWLCYINSTINPACYALCNATFKKT
FKHLLMCHYKNIGATR
SEQ ID NO: 3 homo sapiens muscarinic receptor 2 (gene CHRM2, CDS 1..1401)
Nucleic acid sequence
       1 atgaataact caacaaactc ctctaacaat agcctggctc ttacaagtcc ttataagaca
      61 tttgaagtgg tgtttattgt cctggtggct ggatccctca gtttggtgac cattatcggg
     121 aacatcctag tcatggtttc cattaaagtc aaccgccacc tccagaccgt caacaattac
     181 tttttattca gcttggcctg tgctgacctt atcataggtg ttttctccat gaacttgtac
     241 accctctaca ctgtgattgg ttactggcct ttgggacctg tggtgtgtga cctttggcta
     301 gccctggact atgtggtcag caatgcctca gttatgaatc tgctcatcat cagctttgac
     361 aggtacttct gtgtcacaaa acctctgacc tacccagtca agcggaccac aaaaatggca
     421 ggtatgatga ttgcagctgc ctgggtcctc tctttcatcc tctgggctca agccattctc
     481 ttctggcagt tcattgtagg ggtgagaact gtggaggatg gggagtgcta cattcagttt
     541 ttttccaatg ctgctgtcac ctttggtacg gctattgcag ccttctattt gccagtgatc
     601 atcatgactg tgctatattg gcacatatcc cgagccagca agagcaggat aaagaaggac
     661 aagaaggagc ctgttgccaa ccaagacccc gtttctccaa gtctggtaca aggaaggata
     721 gtgaagccaa caataacaa catgcccagc agtgacgatg gcctggagca caacaaaatc
     781 cagaatggca aagcccccag ggatcctgtg actgaaaact gtgttcaggg agaggagaag
     841 gagagctcca atgactccac ctcagtcagt gctgttgcct ctaatatgag agatgatgaa
     901 ataacccagg atgaaaacac agtttccact tccctgggcc attccaaaga tgagaactct
     961 aagcaaacat gcatcagaat tggcaccaag accccaaaaa gtgactcatg tacccaact
    1021 aataccaccg tggaggtagt ggggtcttca ggtcagaatg gagatgaaaa gcagaatatt
    1081 gtagcccgca agattgtgaa gatgactaag cagcctgcaa aaaagaagcc tcctccttcc
    1141 cgggaaaaga agtcaccag acaatcttg ctattctgt ggctttcat catcacttgg
    1201 gccccataca atgtcatggt gctcattaac accttttgtg caccttgcat ccccaacact
    1261 gtgtggacaa ttggttactg gctttgttac atcaacagca ctatcaaccc tgcctgctat
    1321 gcactttgca atgccacctt caagaagacc tttaaacacc ttctcatgtg tcattataag
    1381 aacataggcg ctacaaggta a
SEQ ID NO: 4

FIG. 3C homo sapiens muscarinic receptor 3
Amino acid sequence
Accession NM_000740
MTLHNNSTTSPLFPNISSSWIHSPSDAGLPPGTVTHFGSYNVSR
AAGNFSSPDGTTDDPLGGHTVWQVVFIAFLTGILALVTIIGNILVIVSFKVNKQLKTV
NNYFLLSLACADLIIGVISMNLFTTYIIMNRWALGNLACDLWLAIDYVASNASVMNLL
VISFDRYFSITRPLTYRAKRTTKRAGVMIGLAWVISFVLWAPAILFWQYFVGKRTVPP
GECFIQFLSEPTITFGTAIAAFYMPVTIMTILYWRIYKETEKRTKELAGLQASGTEAE
TENFVHPTGSSRSCSSYELQQQSMKRSNRRKYGRCHFWFTTKSWKPSSEQMDQDHSSS
DSWNNNDAAASLENSASSDEEDIGSETRAIYSIVLKLPGHSTILNSTKLPSSDNLQVP
EEELGMVDLERKADKLQAQKSVDDGGSFPKSFSKLPIQLESAVDTAKTSDVNSSVGKS
TATLPLSFKEATLAKRFALKTRSQITKRKRMSLVKEKKAAQTLSAILLAFIITWTPYN
IMVLVNTFCDSCIPKTFWNLGYWLCYINSTVNPVCYALCNKTFRTTFKMLLLCQCDKK
KRRKQQYQQRQSVIFHKRAPEQAL
SEQ ID NO: 5 homo sapiens muscarinic receptor 3 (gene CHRM3, CDS 1..1773)
Nucleic acid sequence
```
   1 atgaccttgc acaataacag tacaacctcg cctttgtttc aaacatcag ctcctcctgg
  61 atacacagcc cctccgatgc agggctgccc ccgggaaccg tcactcattt cggcagctac
 121 aatgtttctc gagcagctgg caatttctcc tctccagacg gtaccaccga tgaccctctg
 181 ggaggtcata ccgtctggca agtggtcttc atcgctttct aacgggcat cctggccttg
 241 gtgaccatca tcggcaacat cctggtaatt gtgtcattta aggtcaacaa gcagctgaag
 301 acggtcaaca actacttcct cttaagcctg gcctgtgccg atctgattat cggggtcatt
 361 tcaatgaatc tgtttacgac ctacatcatc atgaatcgat gggcttagg aacttggcc
 421 tgtgacctct ggcttgccat tgactacgta gccagcaatg cctctgttat gaatcttctg
 481 gtcatcagct tgacagata ctttccatc acgaggccgc tcacgtaccg agccaaacga
 541 acaacaaaga gagccggtgt gatgatcggt ctggcttggg tcatctcctt tgtcctttgg
 601 gctcctgcca tcttgttctg gcaatacttt gttggaaaga gaactgtgcc tcgggagag
 661 tgcttcattc agttcctcag tgagcccacc attacttttg gcacagccat cgctgctttt
 721 tatatgcctg tcaccattat gactatttta tactggagga tctataagga aactgaaaag
 781 cgtaccaaag agcttgctgg cctgcaagcc tctgggacag aggcagagac agaaaacttt
 841 gtccaccca cgggcagttc tcgaagctgc agcagttacg aacttcaaca gcaaagcatg
 901 aaacgctcca acaggaggaa gtatggccgc tgccacttct ggttcacaac caagagctgg
 961 aaacccagct ccgagcagat ggaccaagac acagcagca gtgacagttg aacaacaat
1021 gatgctgctg cctccctgga gaactccgcc tcctccgacg aggaggacat tggctccgag
1081 acgagagcca tctactccat cgtgctcaag cttccgggtc acagcaccat cctcaactcc
1141 accaagttac cctcatcgga caacctgcag gtgcctgagg aggagctggg gatggtggac
1201 ttggagagga agccgacaa gctgcaggcc cagaagagcg tggacgatgg aggcagtttt
1261 ccaaaaagct tctccaagct tcccatccag ctagagtcag ccgtggacac agctaagact
1321 tctgacgtca actcctcagt gggtaagagc acggccactc tacctctgtc cttcaaggaa
1381 gccactctgg ccaagaggtt tgctctgaag accagaagtc agatcactaa gcggaaaagg
1441 atgtccctgg tcaaggagaa gaaagcggcc cagaccctca gtgcgatctt gcttgccttc
1501 atcatcactt ggaccccata acacatcatg gttctggtga caccttttg tgacagctgc
1561 atacccaaaa ccttttggaa tctgggctac tggctgtgct acatcaacag caccgtgaac
1621 ccgtgtgct atgctctgtg caacaaaaca ttcagaacca ctttcaagat gctgctgctg
1681 tgccagtgtg acaaaaaaaa gaggcgcaag cagcagtacc agcagagaca gtcggtcatt
1741 tttcacaagc gcgcacccga gcaggccttg tag
```
SEQ ID NO: 6

FIG. 3D homo sapiens muscarinic receptor 4
Amino acid sequence
Accession NM_000741
MANFTPVNGSSGNQSVRLVTSSSHNRYETVEMVFIATVTGSLSL
VTVVGNILVMLSIKVNRQLQTVNNYFLFSLACADLIIGAFSMNLYTVYIIKGYWPLGA
VVCDLWLALDYVVSNASVMNLLIISFDRYFCVTKPLTYPARRTTKMAGLMIAAAWVLS
FVLWAPAILFWQFVVGKRTVPDNHCFIQFLSNPAVTFGTAIAAFYLPVVIMTVLYIHI
SLASRSRVHKHRPEGPKEKKAKTLAFLKSPLMKQSVKKPRPGGRPGGLRNGKLEEAPP
PALPPPPRPVADKDTSNESSSGSATQNTKERPATELSTTEATTPAMPAPPLQPRALNP
ASRWSKIQIVTKQTGNECVTAIEIVPATPAGMRPAANVARKFASIARNQVRKKRQMAA
RERKVTRTIFAILLAFILTWTPYNVMVLVNTFCQSCIPDTVWSIGYWLCYVNSTINPA
CYALCNATFKKTFRHLLLCQYRNIGTAR
SEQ ID NO: 7 homo sapiens muscarinic receptor 4 (gene CHRM4, CDS 1..1437)
Nucleic acid sequence
```
   1 atggccaact tcacacctgt caatggcagc tcgggcaatc agtccgtgcg cctggtcacg
  61 tcatcatccc acaatcgcta tgagacggtg gaaatggtct tcattgccac agtgacaggc
 121 tccctgagcc tggtgactgt cgtgggcaac atcctggtga tgctgtccat caaggtcaac
 181 aggcagctgc agacagtcaa caactactte ctcttcagcc tggcgtgtgc tgatctcatc
 241 ataggcgcct tctccatgaa cctctacacc gtgtacatca tcaagggcta ctggcccctg
 301 ggcgccgtgg tctgcgacct gtggctggcc ctggactacg tggtgagcaa cgcctccgtc
 361 atgaacctte tcatcatcag ctttgaccgc tacttctgcg tcaccaagcc tctcacctac
 421 cctgcccggc gcaccaccaa gatggcaggc ctcatgattg ctgctgcctg gtactgtcc
 481 ttcgtgctct gggcgcctgc catcttgttc tggcagtttg tggtgggtaa gcggacggtg
 541 cccgacaacc actgcttcat ccagttcctg tccaacccag cagtgacctt ggcacagcc
 601 attgctgcct tctacctgcc tgtggtcatc atgacggtgc tgtacatcca catctccctg
 661 gccagtcgca gccgagtcca caagcaccgg cccgagggcc cgaaggagaa gaaagccaag
 721 acgctggcct tcctcaagag cccactaatg aagcagagcg tcaagaagcc ccgcccggga
 781 ggccgcccgg gaggactgcg caatggcaag ctggaggagg ccccccccgcc agcgctgcca
 841 ccgccaccgc gccccgtggc tgataaggac acttccaatg agtccagctc aggcagtgcc
 901 acccagaaca ccaaggaacg cccagccaca gagctgtcca ccacagaggc caccactcc
 961 gccatgcccg cccctcccct gcagccgcgg gccctcaacc cagcctccag atggtccaag
1021 atccagattg tgacgaagca gacaggcaat gagtgtgtga cagccattga gattgtgcct
1081 gccacgccgg ctggcatgcg ccctgcggcc aacgtggccc gcaagttcgc cagcatcgct
1141 cgcaaccagg tgcgcaagaa gcggcagatg gcggcccggg agcgcaaagt gacacgaacg
1201 atctttgcca ttctgctagc cttcatcctc acctggacgc cctacaacgt catggtcctg
1261 gtgaacacct tctgccagag ctgcatccct gacacggtgt ggccattgg ctactggctc
1321 tgctacgtca acagcaccat caaccctgcc tgctatgctc tgtgcaacgc cacctttaaa
1381 aagaccttcc ggcacctgct gctgtgccag tatcggaaca tcggcactgc caggtag
```
SEQ ID NO: 8

FIG. 3E homo sapiens acetylcholinesterase (YT blood group)
Amino acid sequence
Accession XM_036148
MRPPQCLLHTPSLASPLLLLLLWLLGGGVGAEGREDAELLVTVR
GGRLRGIRLKTPGGPVSAFLGIPFAEPPMGPRRFLPPEPKQPWSGVVDATTFQSVCYQ
YVDTLYPGFEGTEMWNPNRELSEDCLYLNVWTPYPRPTSPTPVLVWIYGGGFYSGASS
LDVYDGRFLVQAERTVLVSMNYRVGAFGFLALPGSREAPGNVGLLDQRLALQWVQENV
AAFGGDPTSVTLFGESAGAASVGMHLLSPPSRGLFHRAVLQSGAPNGPWATVGMGEAR
RRATQLAHLVGCPPGGTGGNDTELVACLRTRPAQVLVNHEWHVLPQESVFRFSFVPVV
DGDFLSDTPEALINAGDFHGLQVLVGVVKDEGSYFLVYGAPGFSKDNESLISRAEFLA
GVRVGVPQVSDLAAEAVVLHYTDWLHPEDPARLREALSDVVGDHNVVCPVAQLAGRLA
AQGARVYAYVFEHRASTLSWPLWMGVPHGYEIEFIFGIPLDPSRNYTAEEKIFAQRLM
RYWANFARTGDPNEPRDPKAPQWPPYTAGAQQYVSLDLRPLEVRRGLRAQACAFWNRF
LPKLLSATDTLDEAERQWKAEFHRWSSYMVHWKNQFDHYSKQDRCSDL
SEQ ID NO: 9 homo sapiens acetylcholinesterase (YT blood group)
(gene ACHE, CDS 95..1939)
Nucleic acid sequence
```
   1 cagcctgcgc cggggaacat cggccgcctc cagctcccgg cgcggcccgg cccggcccgg
  61 ctcggccgcc tcagacgccg cctgccctgc agccatgagg ccccgcagt gtctgctgca
 121 cacgccttcc ctggcttccc cactccttct cctcctcctc tggctcctgg gtggaggagt
 181 gggggctgag gccgggagg atgcagagct gctggtgacg gtgcgtgggg gccggctgcg
 241 gggcattcgc ctgaagaccc cggggggccc tgtctctgct tcctgggca tcccctttgc
 301 ggagccaccc atgggacccc gtcgctttct gccaccggag cccaagcagc cttggtcagg
 361 ggtggtagac gctacaacct ccagagtgt ctgctaccaa tatgtggaca ccctataccc
 421 aggttttgag gcaccgaga tgtggaaccc caaccgtgag ctgagcgagg actgcctgta
 481 cctcaacgtg tggacaccat accccggcc tacatccccc accctgtcc tcgtctggat
 541 ctatgggggt ggcttctaca gtgggcctc ctccttggac gtgtacgatg gccgcttctt
 601 ggtacaggcc gagaggactg tgctggtgtc catgaactac cgggtgggag cctttggctt
 661 cctggccctg ccggggagcc gagaggcccc gggcaatgtg gtctcctgg atcagaggct
 721 ggccctgcag tgggtgcagg agaacgtggc agccttcggg ggtgacccga tcagtgac
 781 gctgtttggg gagagcgcgg gagccgcctc ggtgggcatg cacctgctgt ccccgcccag
 841 ccggggcctg ttccacaggg ccgtgctgca gagcggtgcc cccaatggac cctgggccac
 901 ggtgggcatg ggagaggccc gtcgcagggc cacgcagctg gccacccttg tgggctgtcc
 961 tccaggcggc actggtggga atgacacaga gctggtagcc tgccttcgga cacgaccagc
1021 gcaggtcctg gtgaaccacg aatggcacgt gctgcctcaa gaaagcgtct tccggttctc
1081 cttcgtgcct gtggtagatg gagacttcct cagtgacacc ccagaggccc tcatcaacgc
1141 gggagacttc acggcctgc aggtgctggt gggtgtggtg aaggatgagg gctcgtattt
1201 tctggtttac ggggccccag gcttcagcaa agacaacgag tctctcatca gccgggccga
1261 gttcctggcc ggggtgcggg tcggggttcc caggtaagt gacctggcag ccgaggctgt
1321 ggtcctgcat tacacagact ggctgcatcc cgaggacccg cacgcctga ggaggccct
1381 gagcgatgtg gtgggcgacc acaatgtcgt gtgccccgtg cccagctgg ctggcgact
1441 ggctgcccag ggtgcccggg tctacgccta cgtctttgaa caccgtgctt ccacgctctc
1501 ctggcccctg tggatggggg tgccccacgg ctacgagatc gagttcatct ttgggatccc
1561 cctggacccc tctcgaaact acacggcaga ggagaaaatc ttcgcccagc gactgatgcg
1621 atactgggcc aactttgccc gcacagggga tccaatgag ccccgagacc caaggcccc
1681 acaatggccc ccgtacacgg cgggggctca gcagtacgtt agtctggacc tgcggccgct
1741 ggaggtgcgg cggggctgc gcccaggc ctgcgccttc tggaaccgct cctccccaa
1801 attgctcagc gccaccgaca cgctcgacga ggcggagcgc cagtggaagg ccgagttcca
1861 ccgctggagc tctacatgg tgcactggaa gaaccagttc gaccactaca gcaagcagga
1921 tcgctgctca gacctgtgac cccggcggga ccccatgtc ctccgctccg cccggccccc
1981 tagctgtata tactatttat ttcagggctg gctataaca cagacgagcc ccagactctg
2041 cccatcccca ccccaccccg acgtccccg gggctcccgg tcctctgcat gtctcaggct
2101 gagctccctc ccccgcggtg ccttcgcccc tctgggctgc caataaactg ttacag
```
SEQ ID NO: 10

FIG. 3F

Human cholecystokinin A receptor
Amino acid sequence
Accession L13605
MDVVDSLLVNGSNITPPCELGLENETLFCLDQPRPSKEWQPAVQ
ILLYSLIFLLSVLGNTLVITVLIRNKRMRTVTNIFLLSLAVSDLMLCLFCMPFNLIPN
LLKDFIFGSAVCKTTTYFMGTSVSVSTFNLVAISLERYGAICKPLQSRVWQTKSHALK
VIAATWCLSFTIMTPYPIYSNLVPFTKNNNQTANMCRFLLPNDVMQQSWHTFLLLILF
LIPGIVMMVAYGLISLELYQGIKFEASQKKSAKERKPSTTSSGKYEDSDGCYLQKTRP
PRKLELRQLSTGSSSRANRIRSNSSAANLMAKKRVIRMLIVIVVLFFLCWMPIFSANA
WRAYDTASAERRLSGTPISFILLLSYTSSCVNPIIYCFMNKRFRLGFMATFPCCPNPG
PPGARGEVGEEEEGGTTGASLSRFSYSHMSASVPPQ
SEQ ID No: 11

Human cholecystokinin A receptor (gene CCKAR, CDS 72..1358)
Nucleic acid sequence
```
   1 cattagagga atgagccggg agtgagcaat tcaccagctc tccagcactt ggtggaaagc
  61 agcaggcaag gatggatgtg gttgacagcc ttcttgtgaa tggaagcaac atcactcctc
 121 cctgtgaact cgggctcgaa aatgagacgc ttttctgctt ggatcagccc cgtccttcca
 181 aagagtggca gccagcggtg cagattctct tgtactcctt gatattcctg ctcagcgtgc
 241 tgggaaacac gctggtcatc accgtgctga ttcggaacaa gcggatgcgg acggtcacca
 301 acatcttcct cctctccctg gctgtcagcg acctcatgct ctgtctcttc tgcatgccgt
 361 tcaacctcat ccccaatctg ctcaaggatt tcatcttcgg gagcgccgtt tgcaagacca
 421 ccacctactt catgggcacc tctgtgagtg tatctacctt taatctggta gccatatctc
 481 tagagagata tggtgcgatt tgcaaaccct acagtcccg ggtctggcag acaaaatccc
 541 atgctttgaa ggtgattgct gctacctggt gcctttcctt taccatcatg actccgtacc
 601 ccatttatag caacttggtg ccttttacca aaaataacaa ccagaccgcg aatatgtgcc
 661 gctttctact gccaaatgat gttatgcagc agtcctggca cactattctg ttactcatcc
 721 tctttcttat tcctggaatt gtgatgatgg tggcatatgg attaatctct ttggaactct
 781 accagggaat aaaatttgag gctagccaga agaagtctgc taaagaaagg aaacctagca
 841 ccaccagcag cggcaaatat gaggacagcg atgggtgtta cctgcaaaag accaggcccc
 901 cgaggaagct ggagctccgg cagctgtcca ccggcagcag cagcagggcc aaccgcatcc
 961 ggagtaacag ctccgcagcc aacctgatgg ccaagaaaag ggtgatccgc atgctcatcg
1021 tcatcgtggt cctcttcttc ttgtgctgga tgcccatctt cagcgccaac gcctggcggg
1081 cctacgacac cgcctccgca gagcgccgcc tctcaggaac ccccatttcc ttcatcctcc
1141 tcctgtccta cacctcctcc tgcgtcaacc ccatcatcta ctgcttcatg aacaaacgct
1201 tccgcctcgg cttcatggcc accttcccct gctgccccaa tcctggtccc caggggcga
1261 ggggagaggt gggggaggag gaggaaggcg ggaccacagg agcctctctg tccaggttct
1321 cgtacagcca tatgagtgcc tcggtgccac cccagtgaga tgtcccctga ccctccaccg
1381 cagaaggaag gca
```
SEQ ID No: 12

FIG. 3G

Homo sapiens cholecystokinin B receptor
Amino acid sequence
Accession NM_000731
MELLKLNRSVQGTGPGPGASLCRPGAPLLNSSSVGNLSCEPPRI
RGAGTRELELAIRITLYAVIFLMSVGGNMLIIVVLGLSRRLRTVTNAFLLSLAVSDLL
LAVACMPFTLLPNLMGTFIFGTVICKAVSYLMGVSVSVSTLSLVAIALERYSAICRPL
QARVWQTRSHAARVIVATWLLSGLLMVPYPVYTVVQPVGPRVLQCVHRWPSARVRQTW
SVLLLLLLFFIPGVVMAVAYGLISRELYLGLRFDGDSDSDSQSRVRNQGGLPGAVHQN
GRCRPETGAVGEDSDGCYVQLPRSRPALELTALTAPGPGSGSRPTQAKLLAKKRVVRM
LLVIVVLFFLCWLPVYSANTWRAFDGPGAHRALSGAPISFIHLLSYASACVNPLVYCF
MHRRFRQACLETCARCCPRPPRARPRALPDEDPPTPSIASLSRLSYTTISTLGPG
SEQ ID No: 13

Homo sapiens cholecystokinin B receptor (gene CCKBR, CDS 1..1344)
Nucleic acid sequence
```
    1 atggagctgc tcaagctgaa ccggagcgtg cagggaaccg gacccgggcc ggggggcttcc
   61 ctgtgccgcc cggggggcgcc tctcctcaac agcagcagtg tgggcaacct cagctgcgag
  121 cccccctcgca ttcgcggagc cgggacacga gaattggagc tggccattag aatcactctt
  181 tacgcagtga tcttcctgat gagcgttgga ggaaatatgc tcatcatcgt ggtcctggga
  241 ctgagccgcc gcctgaggac tgtcaccaat gccttcctcc tctcactggc agtcagcgac
  301 ctcctgctgg ctgtggcttg catgcccttc accctcctgc ccaatctcat gggcacattc
  361 atctttggca ccgtcatctg caaggcggtt tcctacctca tggggtgtc tgtgagtgtg
  421 tccacgctaa gcctcgtggc catcgcactg gagcggtaca gcgccatctg ccgaccactg
  481 caggcacgag tgtggcagac gcgctcccac gcggctcgcg tgattgtagc cacgtggctg
  541 ctgtccggac tactcatggt gccctacccc gtgtacactg tcgtgcaacc agtggggcct
  601 cgtgtgctgc agtgcgtgca tcgctggccc agtgcgcggg tccgccagac ctggtccgta
  661 ctgctgcttc tgctcttgtt cttcatcccg ggtgtggtta tggccgtggc ctacgggctt
  721 atctctcgcg agctctactt agggcttcgc tttgacggcg acagtgacag cgacagccaa
  781 agcagggtcc gaaaccaagg cgggctgcca ggggctgttc accagaacgg gcgttgccgg
  841 cctgagactg gcgcggttgg cgaagacagc gatggctgct acgtgcaact tccacgttcc
  901 cggcctgccc tggagctgac ggcgctgacg gctccagggc cgggatccgg ctcccggccc
  961 acccaggcca agctgctggc taagaagcgc gtggtgcgaa tgttgctggt gatcgttgtg
 1021 ctttttttc tgtgttggtt gccagtttat agtgccaaca cgtggcgcgc ctttgatggc
 1081 ccgggtgcac accagcact ctcgggtgct cctatctcct tcattcactt gctgagctac
 1141 gcctcggcct gtgtcaaccc cctggtctac tgcttcatgc accgtcgctt cgccaggcc
 1201 tgcctggaaa cttgcgctcg ctgctgcccc cggcctccac gagctcgccc cagggctctt
 1261 cccgatgagg acccctcccac tccctccatt gcttcgctgt ccaggcttag ctacaccacc
 1321 atcagcacac tgggccctgg ctgaggagta gaggggccgt gggggttgag gcagggcaaa
 1381 tgacatgcac tgacccttcc agacatagaa aacacaaacc acaactgaca caggaaacca
 1441 acacccaaag catggactaa ccccaacgac aggaaaaggt agcttacctg acacaagagg
 1501 aataagaatg gagcagtaca tgggaaagga ggcatgcctc tgatatggga ctgagcctgg
 1561 cccatagaaa catgacactg accttggaga gacacagcgt ccctagcagt gaactatttc
 1621 tacacagtgg gaactctgac aagggctgac ctgcctctca cacacataga ttaatggcac
 1681 tgattgtttt agagactatg gagcctggca caggactgac tctgggatgc tcctagtttg
 1741 acctcacagt gacccttccc aatcagcact gaaatacca tcaggcctaa tctcatacct
 1801 ctgaccaaca ggctgttctg cactgaaaag gttcttcatc ccttccagt taaggaccgt
 1861 ggccctgccc tctccttcct tcccaaactg ttcaagaaat aataaattgt ttggcttcct
 1921 cctgaaaaaa aaaaaaaaa aaaaaaaaa aaaaaaaaa aggaattcc
```
SEQ ID No: 14

− Gastrin-17          + Gastrin-17

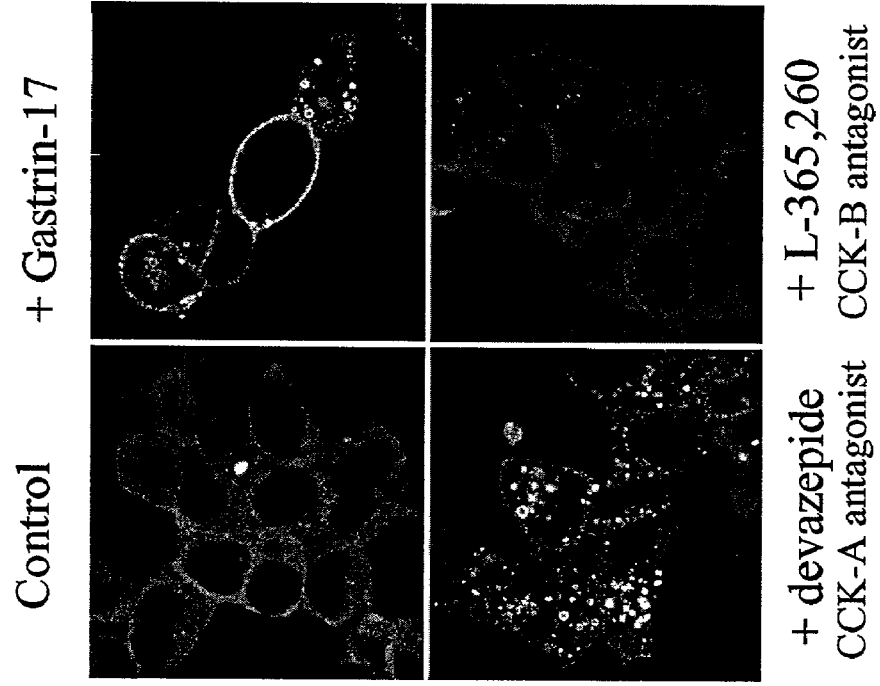
FIG 5C
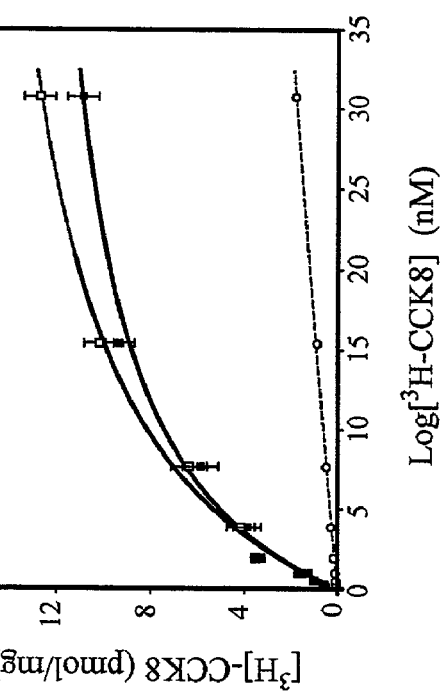
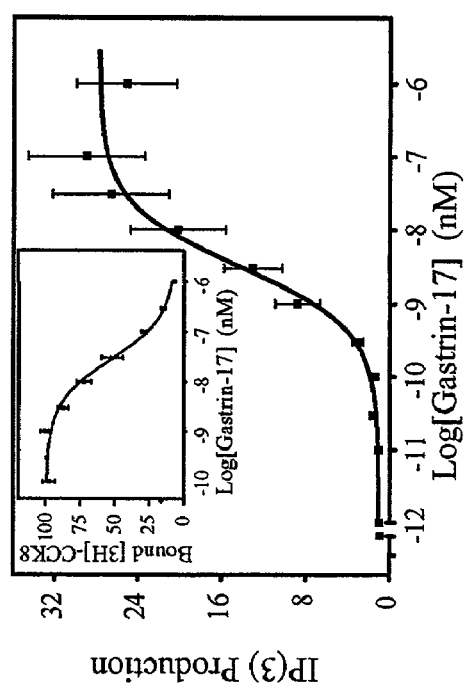

SINGLE-CELL BIOSENSOR FOR THE MEASUREMENT OF GPCR LIGANDS IN A TEST SAMPLE

This application claims priority under 35 U.S.C. § 119(e) to U.S. Ser. No. 60/295,945 filed Jun. 5, 2001, and is a continuation-in-part claiming priority under 35 U.S.C. § 120 to U.S. Ser. No. 09/631,468 filed Aug. 3, 2000, now abandoned which is a continuation of U.S. Ser. No. 09/233,530 filed on Jan. 20, 1999, now U.S. Pat. No. 6,110,693, which is a continuation of U.S. Ser. No. 08/869,568 filed on Jun. 5, 1997, now U.S. Pat. No. 5,891,646, the contents of which are hereby incorporated by reference in their entireties.

This work was supported by National Institutes of Health Grants DK 02544, HL 61365, and NS 19576, and therefore the government may have certain rights to the invention.

FIELD OF THE INVENTION

The present invention relates to methods of analyzing the presence and concentration of a GPCR ligand in test samples, including biological and environmental samples. Preferably, the present invention relates to the detection of multiple GPCR ligands in a test sample, wherein the test sample may be heterogeneous. The present invention provides improved methods of disease diagnosis, as well as detection of harmful chemicals, such as insecticides, neurotoxins, and chemicals used in bioterrorism.

BACKGROUND

G protein-coupled receptors (GPCRs) are cell surface proteins that translate hormone or ligand binding into intracellular signals. GPCRs are found in all animals, insects, and plants. GPCR signaling plays a pivotal role in regulating various physiological functions including phototransduction, olfaction, neurotransmission, vascular tone, cardiac output, digestion, pain, and fluid and electrolyte balance. Although they are involved in various physiological functions, GPCRs share a number of common structural features. They contain seven membrane domains bridged by alternating intracellular and extracellular loops and an intracellular carboxyl-terminal tail of variable length.

GPCRs have been implicated in a number of disease states, including, but not limited to cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer.

The magnitude of the physiological responses controlled by GPCRs is linked to the balance between GPCR signaling and signal termination. The signaling of GPCRs is controlled by a family of intracellular proteins called arrestins. Arrestins bind activated GPCRs, including those that have been agonist-activated and especially those that have been phosphorylated by G protein-coupled receptor kinases (GRKs).

The abnormal regulation of hormones that bind to G protein-coupled receptors underlies the pathogenesis of many diseases. The ability to measure serum and tissue levels of these regulators, while clinically and scientifically desirable, is presently limited to very specialized biochemical and immunochemical assays.

Altered concentrations of a GPCR ligand in a biological sample may be indicative of a disease state. Altered concentrations of a GPCR ligand in an environmental sample may indicate the presence of harmful chemicals. There is a need for highly sensitive and specific methods for the quantitative detection of GPCR ligands in a heterogeneous sample, as well as methods for the detection of the multiple bioactive isoforms of a GPCR ligand in a heterogeneous sample. Sensitive, rapid methods of analyzing the presence of GPCR ligands in heterogeneous samples, both biological and environmental, would improve disease diagnosis and the detection of harmful compounds in the environment.

SUMMARY

A first aspect of the present invention is a method of detecting a GPCR ligand in a test sample. The test sample is a biological sample, an environmental sample, or a sample derived from a biological sample or an environmental sample. Preferably, a cell is provided that includes at least one GPCR and an arrestin. The test sample is provided and the cell is exposed to the test sample. The cellular distribution of the GPCR or arrestin in the presence of the test sample is determined. The cellular distribution of the GPCR or the arrestin in the presence of the test sample may be compared to the cellular distribution of the GPCR or arrestin in the absence of the test sample.

In one aspect of the present invention, the GPCR or the arrestin is detectably labeled, another endogenous molecule is detectably labeled, or another exogenous molecule is detectably labeled. The distribution of the detectably labeled molecules represents the cellular distribution of the GPCR or the arrestin proteins.

In a further aspect, the cellular distribution of the GPCR or arrestin is determined at different time points after exposure to the test sample. The cellular distribution of the GPCR or arrestin is determined after exposure to different concentrations of the test sample. The cellular distribution of the detectably labeled molecules may be quantified.

In an additional aspect, the concentration of the ligand in the test sample is quantified by comparing the cellular distribution of the GPCR of arrestin in the presence of the test sample to the cellular distribution of the GPCR or arrestin in the presence of a known concentration of the ligand.

The biological sample provided as the test sample may be serum, tissue, blood, urine, or derived therefrom.

In a further aspect, the GPCR is CCK-B or CCK-A. The ligand may be gastrin, preprogastrin, cleaved preprogastrin, gastrin-34, gastrin-17, pentagastrin, progastrin, glycine-extended gastrin-17, glycine-extended gastrin-34, gastrin-71, gastrin-6, hG17, a compound with an amidated tetrapeptide of the sequence Trp-Met-Asp-Phe-NH$_2$ (SEQ ID NO: 15), or another bioactive isoform of gastrin.

In a further aspect, the GPCR is a muscarinic receptor. The ligand may be acetylcholine.

In an additional aspect, the labeled molecule may be localized in the cytosol, plasma membrane, clathrin-coated pits, endocytic vesicles, or endosomes. An increase in the local concentration of the labeled molecule results in an increase in the local signal intensity. The signal intensity of the labeled molecule in the plasma membrane, clathrin-coated pits, endocytic vesicles, or endosomes may be increased with respect to the level of signal intensity in the cytosol. The local signal intensity may be increased in the presence of increased concentration of ligand in the test sample.

In a further aspect, the concentration of the ligand in the test sample indicates a disease state. The concentration of the ligand in the test sample may indicate the presence of a compound in the test sample that alters the ligand concentration. The concentration of the ligand in the test sample indicates the presence of a compound in the test sample that modifies acetylcholine. The concentration of the ligand in the test sample indicates the presence of a compound that inhibits an acetylcholinesterase.

The detectable molecule may be a radioisotope, an epitope tag, an affinity label, an enzyme, a fluorescent group, or a chemiluminescent group. The molecule may be detectably labeled due to its interaction with another molecule, which may be detectable labeled.

The present invention relates to a method of monitoring a GPCR ligand in a mammal. The test sample is a biological sample derived from the mammal. Preferably, a cell is provided that includes at least one GPCR and an arrestin. The test sample is provided and the cell is exposed to the test sample. The cellular distribution of the GPCR or arrestin in the presence of the test sample is determined. The concentration of the ligand in the test sample may be quantified by comparing the cellular distribution of the GPCR or arrestin in the presence of the test sample to the cellular distribution of the GPCR or arrestin in the presence of a known concentration of the ligand. This method may be used to monitor a clinical condition, which may indicate the presence of a disease state, or may indicate that the subject has a disorder or is at risk for developing a disorder. The clinical condition monitored may be gastrointestinal cancer, hypergastrinemia, atrophic gastritis, gastric ulcers, malignant tumors, or other GPCR-related disease. The mammal may be on prolonged acid suppressive medications.

In a further aspect of the present invention, the provided cell may express a protein that increases the internalization of the GPCR. The GPCR may itself be modified, resulting in an increased concentration of the labeled molecule at the plasma membrane, clathrin-coated pits, endocytic vesicles, or endosomes. The provided cell may express a G protein-coupled receptor kinase (GRK).

One aspect of the present invention is a single cell biosensor. This biosensor includes a cell which overexpresses arrestin and at least one GPCR, wherein the GPCR, the arrestin, or the cell is detectably labeled for monitoring internalization of the GPCR. A further aspect of the present invention is a method of detecting a GPCR ligand in a test sample, wherein the test sample is a biological sample, an environmental sample, or a sample derived therefrom. In this method, the single cell biosensor is provided, the biosensor is exposed to the test sample, and the cellular distribution of the GPCR or arrestin in the presence of the test sample is determined. In the single cell biosensor, the GPCR may be a CCK-A, a CCK-B, or a muscarinic receptor. The arrestin may be conjugated to a Green Fluorescent Protein. The biosensor may have increased sensitivity due to longer incubation time, increased concentration of test sample, GPCR mutation, or GPCR antibodies.

The present invention is related to a method of altering GPCR internalization, comprising providing to the cells an effective amount of an antagonist of CCK-B.

In the methods of the present invention, the cellular distribution may be visualized by flow cytometry or fluorescence confocal microscopy. A computer may analyze an image of the cellular distribution and the distribution may be quantified. The test sample to be analyzed may comprise a ligand of the GPCR, or an antagonist of the GPCR.

The present invention is related to a method of detecting a compound which modulates a GPCR ligand in a test sample. The test sample is a biological sample, an environmental sample, or a sample derived from a biological sample or an environmental sample. Preferably, a cell is provided that includes at least one GPCR and an arrestin. The test sample is provided and the cell is exposed to the test sample. The cellular distribution of the GPCR or arrestin in the presence of the test sample is determined. The cellular distribution of the GPCR or the arrestin in the presence of the test sample may indicate the presence of a compound which modulates a GPCR ligand.

The present invention is related to a method of detecting a compound which modulates a GPCR ligand in a test sample. The test sample is a biological sample, an environmental sample, or a sample derived from a biological sample or an environmental sample. Preferably, a cell is provided that includes at least one GPCR and an arrestin. The test sample is provided and the cell is exposed to the test sample. The cellular distribution of the GPCR or arrestin in the presence of the test sample is determined.

The present invention is related to a method of continuous screening of GPCR ligands in a test sample. The test sample is a biological sample, an environmental sample, or a sample derived from a biological sample or an environmental sample. Preferably, a cell is provided that includes at least one GPCR and an arrestin. The test sample is provided and the cell is exposed to the test sample. The cellular distribution of the GPCR or arrestin in the presence of the test sample is determined. Then, the cell is replaced with another cell comprising a GPCR and an arrestin.

A further aspect of the present invention is a method of detecting an inhibitor of acetylcholinesterase in a test sample. The test sample is a biological sample, an environmental sample, or a sample derived from a biological sample or an environmental sample. Preferably, a cell is provided that expresses a muscarinic receptor and an arrestin. A mixture, containing a test sample, acetylcholinesterase, and an agonist of the muscarinic receptor, is provided. The agonist is sensitive to acetylcholinesterase. The cell is exposed to the mixture. The cellular distribution of the muscarinic receptor or arrestin in the presence of the test sample is determined. The agonist may be acetylcholine.

In an aspect of the present invention, the test sample may contain acetylcholine and acetylcholinesterase. The test sample may contain an agonist. The ligand may have been identified, and multiple bioactive isoforms of the GPCR ligand in the test sample may be detected.

In a further aspect of the invention, the test sample may be derived from a mammal with hypergastrinemia. The gastrin concentration in the test sample may be less than 10 nM. The test sample may be heterogeneous.

In an aspect of the present invention, the cellular distribution may determined after 15-30 minutes of exposure to the test sample. The cellular distribution may be determined after 1 hour of exposure to the test sample. The cell may be exposed to the test sample at a temperature of approximately 37° C.

The present invention is related to a method of detecting a compound that modulates GPCR internalization in a test sample. The test sample is a biological sample, an environmental sample, or a sample derived from a biological sample or an environmental sample. Preferably, a cell is provided that includes at least one GPCR and an arrestin. The test sample is provided and the cell is exposed to the test sample. The cellular distribution of the GPCR or arrestin in the presence of the test sample is determined.

In a further aspect, the present invention is related to a method of detecting a compound that modulates GPCR internalization in a test sample. The test sample is a biological sample, an environmental sample, or a sample derived from a biological sample or an environmental sample. Preferably, a cell is provided that includes at least one GPCR and an arrestin. The cell is exposed to an agonist. The test sample is provided and the cell is exposed to the test sample. The cellular distribution of the GPCR or arrestin in the presence of the test sample is determined.

A further aspect of the present invention is a bioarray containing at least one single cell biosensor. The bioarray may detect multiple GPCR ligands.

BRIEF DESCRIPTION OF DRAWINGS

The objects and advantages of the invention will be understood by reading the following detailed description in conjunction with the drawings in which:

FIG. 1 is an illustrative, non-limiting list of known GPCRs with which the present invention may be used is contained in FIG. 1. The receptors are grouped according to classical divisions based on structural similarities and ligands. FIGS. 1A to 1B includes a non-limiting list of the known Class I GPCRs. FIG. 1C is a non-limiting list of the known Class II and Class III GPCRs.

FIG. 2 lists some of the over 40 different GPCRs that may associate with arrestin and subsequently internalize. This may be visualized using expressed GPCRs and fusion proteins between arrestin and a green fluorescent protein.

FIG. 3A illustrates the amino acid and nucleic acid sequences of the *homo sapiens* muscarinic receptor 1, Accession NM_000738. FIG. 3B illustrates the amino acid and nucleic acid sequences of the *homo sapiens* muscarinic receptor 2, Accession NM_000739. FIG. 3C illustrates the amino acid and nucleic acid sequences of the *homo sapiens* muscarinic receptor 3, Accession NM_000740. FIG. 3D illustrates the amino acid and nucleic acid sequences of the *homo sapiens* muscarinic receptor 4, Accession NM_000741. FIG. 3E illustrates the amino acid and nucleic acid sequences of the *homo sapiens* acetylcholinesterase (YT blood group), Accession XM_036148. FIG. 3F illustrates the amino acid and nucleic acid sequences of the human cholecystokinin A receptor, Accession L13605. FIG. 3G illustrates the amino acid and nucleic acid sequences of the *homo sapiens* cholecystokinin B receptor, Accession NM_000731. Amino acid sequences are listed in the amino-terminal to carboxy-terminal orientation. Nucleic acid sequences are listed in the 5'→3' orientation.

FIG. 4 illustrates the uniformity of arrestin-GFP and CCK-B receptor expression in cells by flow cytometry and arrestin-GFP translocation.

FIG. 5 shows the characterization of ligand binding and second messenger response in a cell line expressing arrestin-GFP and the CCK-B receptor. As shown in FIG. 5A, cells from Clone A were incubated with increasing concentrations of [$^3$H]CCK-8 in order to determine the average CCK-B receptor expression per cell and the receptor affinity for [$^3$H] CCK-8. FIG. 5B shows that Clone A cells were exposed to increasing concentrations of hG17 peptide in order to evaluate the IP3 second messenger response. The inset shows the competitive displacement of [$^3$H]CCK8 by hG17 from this cell line. FIG. 5C shows the fluorescence images of cells from Clone A that were treated with vehicle (upper left panel), or treated for one hour with 10 nM of the agonist hG17 (upper right panel), or with 10 nM hG17 plus 1 µM of the CCK-A antagonist devazepide (L-364,718, lower left panel); or with 10 nM hG17 plus 1 µM, of the CCK-B antagonist (lower right panel).

FIG. 6 illustrates the dose response to hG17 at five minutes in an HEK-293 cell line containing arrestin-GFP and the CCK-B receptor.

FIG. 7 shows the calculation of the Fluorescence Signal from the Distribution of βarrestin2-GFP.

FIG. 9 shows the dose response at one hour in a clonal cell line containing arrestin-GFP and the CCK-B receptor.

DETAILED DESCRIPTION

Figure 4A:
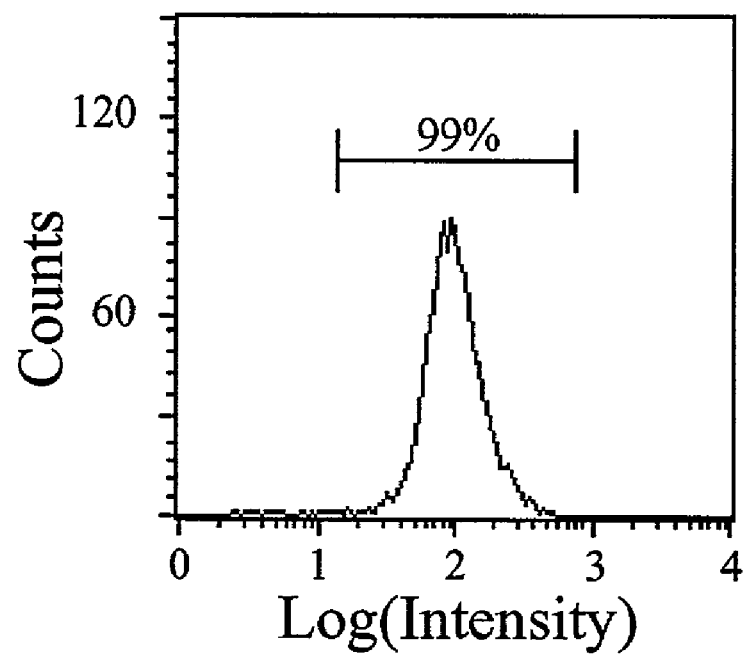
FIG. 4A shows the relative expression of arrestin-GFP in cells belonging to Clone A.

In accordance with the present invention there may be employed conventional molecular biology, microbiology, immunology, and recombinant DNA techniques within the skill of the art. Such techniques are explained fully in the literature. See, e.g., Sambrook et al, "Molecular Cloning: A Laboratory Manual" (3$^{rd}$ edition, 2001); "Current Protocols in Molecular Biology" Volumes I-IV [Ausubel, R. M., ed. (2002 and updated bimonthly)]; "Cell Biology: A Laboratory Handbook" Volumes I-III [J. E. Celis, ed. (1994)]; "Current Protocols in Immunology" Volumes I-IV [Coligan, J. E., ed. (2002 and updated bimonthly)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Culture of Animal Cells, 4th edition" [R. I. Freshney, ed. (2000)]; "Immobilized Cells And Enzymes" [IRL Press, (1986)]; B. Perbal, "A Practical Guide To Molecular Cloning" (1988); *Using Antibodies: A Laboratory Manual Portable Protocol No. I*, Harlow, Ed and Lane, David (Cold Spring Harbor Press, 1998); *Using Antibodies: A Laboratory Manual*, Harlow, Ed and Lane, David (Cold Spring Harbor Press, 1999); "G Protein-Coupled Receptors" [T. Haga, et al., eds. (1999)].

Unless otherwise stated, the following terms used in the specification and claims have the meanings given below:

"hG17" is the human gastrin-17 amino acid peptide. It may be produced in a human, another organism, such as *E. coli*, yeast, mouse, or it may be synthesized chemically.

"RIA", or radioimmunoassay, is an antibody-based method of detecting a particular compound in a sample. Presently, serum gastrin measurements are performed by RIA using antibodies directed against one or more distinct gastrin isoforms.

A "neurotoxin" is any compound that has the ability to damage or destroy nerve tissues. Of particular relevance to the present invention are compounds which inhibit acetylcholinesterase. Normally, acetylcholinesterase breaks down acetylcholine, a natural ligand of the muscarinic receptor. Nerve toxins which inhibit acetylcholinesterase prevent the normal degradation of acetylcholine. The present invention can be used to detect the presence of nerve toxins which inhibit acetylcholinesterase by detecting the acetylcholine concentration in a sample. Compounds that inhibit acetylcholinesterase include organophosphate insecticides such as diazinon and the neurotoxin sarin.

"Acetylcholine" is a neurotransmitter and functions at least at neuromuscular synapses, which are synapses between neurons and cardiac, smooth, and skeletal muscle, as well as at a variety of neuron-neuron synapses in the central and peripheral nervous systems. It is synthesized in nerve terminals from acetylCoA and choline, in a reaction catalyzed by the enzyme choline acetyltransferase.

A "muscarinic receptor" is a GPCR which is located at least in many brain neurons, sympathetic neurons, smooth muscle, gland cells and heart cells. Muscarinic receptor is meant to include muscarinic acetylcholine receptor, muscarinic cholinergic receptor, other references for muscarinic receptors, including sub-types 1, 2, 3, 4, and other sub-types known to those of skill in the art. The term muscarinic receptor includes, but is not limited to, muscarinic receptor sequences of *homo sapiens*, eukaryota, metazoa, chordata, craniata, vertebrate, euteleostomi, mammalia, eutheria, primates, catarrhini, homimidae, homo, and others. Acetylcholine is an agonist of the muscarinic receptor.

"Acetylcholinesterase" is the enzyme which degrades acetylcholine into acetate and choline. This enzyme is clustered at high concentrations in the synaptic cleft.

An "acetylcholinesterase inhibitor" is a compound that inhibits the activity of acetylcholinesterase. Compounds that inhibit acetylcholinesterase include organophosphate insecticides such as diazinon and the neurotoxin sarin.

"Insecticides" include compounds which are nerve toxins. Insecticides, including organophosphate insecticides such as diazinon, may be acetylcholinesterase inhibitors.

A "bioassay" is the use of a physiological response to assay for a biologically active compound.

A "biosensor" utilizes a biological process or component to detect the presence of compound. The single-cell biosensors of the present invention are cells which include a GPCR and an arrestin. By exposing the cells to a heterogeneous sample and monitoring the GPCR or arrestin response to the sample, they are useful for the detection of a GPCR ligand in a heterogeneous sample.

"ZE syndrome" is Zollinger-Ellison syndrome, which is caused by a gastrin producing tumor.

"Biological sample" is intended to include tissues, cells and/or biological fluids isolated from a subject, as well as tissues, cells and fluids present within a subject; wherein said sample can be blood, serum, a urine sample, a fecal sample, a tumor sample, a cellular wash, an oral sample, sputum, biological fluid, a tissue extract, freshly harvested cells, or cells which have been incubated in tissue culture. The biological sample may be selected from the group consisting of whole blood, serum, plasma, saliva, urine, sweat, ascitic fluid, peritoneal fluid, synovial fluid, amniotic fluid, cerebrospinal fluid, skin biopsy, and the like. The biological sample may includes serum, whole blood, plasma, lymph and ovarian follicular fluid as well as other circulatory fluid and saliva, mucus secretion, and respiratory fluid or fractionated portions thereof. The sample may be extracted, untreated, treated, diluted or concentrated from a patient.

"Biologically active" and "bioactive" are used interchangeably herein to refer to a compound, compound fragment, or compound isoform which has biological activity. Preferably, biologically active or bioactive is used to describe a GPCR ligand, or ligand isoforms, which have the ability to bind a GPCR.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. For example, stringent conditions may include hybridization 6×SSC or 6×SSPE at 68° C. for 1 hour to 3 days. Defining appropriate hybridization conditions is within the skill of the art. See, e.g., Sambrook et al, "Molecular Cloning: A Laboratory Manual" ($3^{rd}$ edition, 2001), supra; DNA Cloning, Vols. I & II, supra; Nucleic Acid Hybridization, supra.

It should be appreciated that also within the scope of the present invention are DNA sequences having the same amino acid sequence as SEQ ID NO:1, 3, 5, 7, 9, 11, and 13, but which are degenerate to SEQ ID NO:1, 3, 5, 7, 9, 11, and 13. By "degenerate to" is meant that a different three-letter codon is used to specify a particular amino acid.

"Arrestin" means all types of naturally occurring and engineered variants of arrestin, including, but not limited to, visual arrestin (sometimes referred to as Arrestin 1), βarrestin 1 (sometimes referred to as Arrestin 2), and βarrestin 2 (sometimes referred to as Arrestin 3).

"βARK1" is a GRK termed β-adrenergic receptor kinase 1, also called GRK2.

"βAR" is a GPCR termed a β-adrenergic receptor.

"Gastrin receptors" are GPCRs, preferably CCK-A and CCK-B, that bind gastrin. CCK-A and CCK-B, the cholecystokinin A and B receptors, are GPCRs that bind gastrin, cholecystokinin, and similar ligands.

"Internalization" of a GPCR is the intracellular translocation of a GPCR. Internalization includes the translocation of a GPCR to clathrin-coated pits, endocytic vesicles, and endosomes.

"Carboxyl-terminal tail" means the carboxyl-terminal tail of a GPCR. The carboxyl-terminal tail of many GPCRs begins shortly after the conserved NPXXY motif that marks the end of the seventh transmembrane domain (i.e. what follows the NPXXY motif is the carboxyl-terminal tail of the GPCR). The carboxyl-terminal tail may be relatively long (approximately tens to hundreds of amino acids), relatively short (approximately tens of amino acids), or virtually non-existent (less than approximately ten amino acids). As used herein, "carboxyl-terminal tail" shall mean all three variants (whether relatively long, relatively short, or virtually non-existent).

"Class A receptors" preferably do not translocate arrestin to endocytic vesicles or endosomes in HEK-293 cells.

"Class B receptors" preferably do translocate arrestin to endocytic vesicles or endosomes in HEK-293 cells.

"DACs" mean any desensitization active compounds. Desensitization active compounds are any compounds that influence the GPCR desensitization mechanism by either stimulating or inhibiting the process. DACs influence the GPCR desensitization pathway by acting on any cellular component of the process, as well as any cellular structure implicated in the process, including but not limited to, arrestins, GRKs, GPCRs, PI3K, AP-2 protein, clathrin, protein phosphatases, and the like. DACs may include, but are not limited to, compounds that inhibit arrestin translocating to a GPCR, compounds that inhibit arrestin binding to a GPCR, compounds that stimulate arrestin translocating to a GPCR, compounds that stimulate arrestin binding to a GPCR, compounds that inhibit GRK phosphorylation of a GPCR, compounds that stimulate GRK phosphorylation of a GPCR, compounds that inhibit protein phosphatase dephosphorylation of a GPCR, compounds that stimulate protein phosphatase dephosphorylation of a GPCR, compounds that regulate the release of arrestin from a GPCR, antagonists of a GPCR, inverse agonists and the like. DACs preferably inhibit or stimulate the GPCR desensitization process without binding to the same ligand binding site of the GPCR as traditional agonists and antagonists of the GPCR. DACs act independently of the GPCR, i.e., they do not have high specificity for one particular GPCR or one particular type of GPCRs.

"Detectable molecule" means any molecule capable of detection by spectroscopic, photochemical, biochemical, immunochemical, electrical, radioactive, and optical means, including but not limited to, fluorescence, phosphorescence, and bioluminescence and radioactive decay. Detectable molecules include, but are not limited to, GFP, luciferase, $\beta$-galactosidase, rhodamine-conjugated antibody, and the like. Detectable molecules include radioisotopes, epitope tags, affinity labels, enzymes, fluorescent groups, chemiluminescent groups, and the like. Detectable molecules include molecules which are directly or indirectly detected as a function of their interaction with other molecule(s).

"GFP" means Green Fluorescent Protein which refers to various naturally occurring forms of GFP which may be isolated from natural sources or genetically engineered, as well as artificially modified GFPs. GFPs are well known in the art. See, for example, U.S. Pat. Nos. 5,625,048; 5,777,079; and 6,066,476. It is well understood in the art that GFP is readily interchangeable with other fluorescent proteins, isolated from natural sources or genetically engineered, including but not limited to, yellow fluorescent proteins (YFP), red fluorescent proteins (RFP), cyan fluorescent proteins (CFP), blue fluorescent proteins, luciferin, UV excitable fluorescent proteins, or any wave-length in between. As used herein, "GFP" shall mean all fluorescent proteins known in the art.

"Unknown or Orphan Receptor" means a GPCR whose function and/or ligands are unknown.

"NPXXY motif" means a conserved amino acid motif that marks the end of the seventh transmembrane domain. The conserved amino acid motif begins with asparagine and proline followed by two unspecified amino acids and then a tyrosine. The two unspecified amino acids may vary among GPCRs but the overall NPXXY motif is conserved.

In referring to a polypeptide, "downstream" means toward a carboxyl-terminus of an amino acid sequence, with respect to the amino-terminus. In referring to a polynucleotide, "downstream" means in the 3' direction.

In referring to a polypeptide, "upstream" means toward an amino-terminus of an amino acid sequence, with respect to the carboxyl-terminus. In referring to a polynucleotide, "upstream" means in the 5' direction.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces $\beta$-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. Heterologous DNA may include, but is not limited to, DNA from a heterologous species ("foreign DNA"), as described in U.S. Pat. No. 6,331,415, which is incorporated by reference herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

"Hybridization" means hydrogen bonding, which may be Watson-Crick, Hoogsteen or reversed Hoogsteen hydrogen bonding, between complementary nucleoside or nucleotide bases. For example, adenine (A) and thymine (T) are complementary nucleobases which pair through the formation of hydrogen bonds.

The term "standard hybridization conditions" refers to salt and temperature conditions substantially equivalent to 6×SSC and 68° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined Tm with washes of higher stringency, if desired. These conditions are described in Protocol 10 of Sambrook et al, "Molecular Cloning: A Laboratory Manual" ($3^{rd}$ edition, 2001).

By "animal" is meant any member of the animal kingdom including vertebrates (e.g., frogs, salamanders, chickens, or horses) and invertebrates (e.g., worms, etc.). "Animal" is also meant to include "mammals." Preferred mammals include livestock animals (e.g., ungulates, such as cattle, buffalo, horses, sheep, pigs and goats), as well as rodents (e.g., mice, hamsters, rats and guinea pigs), canines, felines, primates, lupine, camelid, cervidae, rodent, avian and ichthyes.

"Antagonist(s)" include all agents that interfere with wild-type and/or modified GPCR binding to an agonist, wild-type and/or modified GPCR desensitization, wild-type and/or modified GPCR binding arrestin, wild-type and/or modified GPCR endosomal localization, internalization, and the like, including agents that affect the wild-type and/or modified GPCRs as well as agents that affect other proteins involved in wild-type and/or modified GPCR signaling, desensitization, endosomal localization, resensitization, and the like.

"GPCR" means G protein-coupled receptor and includes GPCRs naturally occurring in nature, as well as GPCRs which have been modified. Such modified GPCRs are described in U.S. Ser. No. 09/993,844 filed on Nov. 5, 2001 and U.S. Ser. No. 10/054,616 filed on Jan. 22, 2002 which is incorporated herein by reference in its entirety.

"Abnormal GPCR desensitization" and "abnormal desensitization" mean that the GPCR desensitization pathway is disrupted such that the balance between active receptor and desensitized receptor is altered with respect to wild-type conditions. There may be more active receptor than normal or there may be more desensitized receptor than wild-type conditions. Abnormal GPCR desensitization may be the result of a GPCR that is constitutively active or constitutively desensitized, leading to an increase above normal in the signaling of that receptor or a decrease below normal in the signaling of that receptor.

"Concurrent administration," "administration in combination," "simultaneous administration," or "administered simultaneously" mean that the compounds are administered at the same point in time or sufficiently close in time that the results observed are essentially the same as if the two or more compounds were administered at the same point in time.

"Conserved abnormality" means an abnormality in the GPCR pathway, including but not limited to, abnormalities in GPCRs, GRKs, arresting, AP-2 protein, clathrin, protein phosphatase and the like, that may cause abnormal GPCR signaling. This abnormal GPCR signaling may contribute to a GPCR-related disease.

"Desensitized GPCR" means a GPCR that presently does not have ability to respond to agonist and activate conventional G protein signaling. Desensitized GPCRs of the present invention do not properly respond to agonist, are phosphorylated, bind arrestin, constitutively localize in clathrin-coated pits, and/or constitutively localize to endocytic vesicles or endosomes.

"Desensitization pathway" means any cellular component of the desensitization process, as well as any cellular structure implicated in the desensitization process and subsequent processes, including but not limited to, arrestins, GRKs, GPCRs, AP-2 protein, clathrin, protein phosphatases, and the like. In the methods of assaying of the present invention, the polypeptides may be detected, for example, in the cytoplasm, at a cell membrane, in clathrin-coated pits, in endocytic vesicles, endosomes, any stages in between, and the like.

"GPCR signaling" means GPCR induced activation of G proteins. This may result in, for example, cAMP production.

"G protein-coupled receptor kinase" (GRK) includes any kinase that has the ability to phosphorylate a GPCR.

"G protein-coupled receptor phosphatase" includes any phosphatase that has the ability to dephosphorylate a GPCR.

"*Homo sapien* GPCR" means a naturally occurring GPCR in a *Homo sapien*.

"Inverse agonist" means a compound which, upon binding to the GPCR, inhibits the basal intrinsic activity of the GPCR. An inverse agonist is a type of antagonist.

An "isolated" or "purified" nucleic acid molecule or protein, biologically active portion thereof, or antibody is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5 and 3 ends of the nucleic acid) in the genomic DNA of the organism from which the nucleic acid is derived. For purposes of the invention, "isolated" when used to refer to nucleic acid molecules, excludes isolated chromosomes. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, or 5% (by dry weight) of another protein. When the protein or biologically active portion thereof is recombinantly produced, preferably, culture medium represents less than about 30%, 20%, 10%, or 5% of the volume of the protein preparation. When protein is produced by chemical synthesis, preferably the protein preparations have less than about 30%, 20%, 10%, or 5% (by dry weight) of chemical precursors or non-protein chemicals.

"Modified GRK" means a GRK modified such that it alters desensitization.

"Naturally occurring GPCR" means a GPCR that is present in nature.

"Odorant ligand" means a ligand compound that, upon binding to a receptor, leads to the perception of an odor including a synthetic compound and/or recombinantly produced compound including agonist and antagonist molecules.

"Odorant receptor" means a receptor protein normally found on the surface of olfactory neurons which, when activated (normally by binding an odorant ligand) leads to the perception of an odor.

"Sensitized GPCR" means a GPCR that presently has ability to respond to agonist and activate conventional G protein signaling.

GPCRs and Desensitization

The present invention is generally directed to the detection of a GPCR ligand present in a heterogeneous solution that contains one or more GPCR ligands. For example, such solutions could include serum, blood, another biological sample, or an environmental sample.

G protein-coupled receptors (GPCRs) regulate a wide variety of physiological processes and are important targets for clinical drug discovery. GPCRs function in vivo as sensitive plasma-membrane sensors that sample the extracellular environment for biologically active molecules. They transduce the binding event across the plasma membrane by interacting with one or more of the numerous classes of intracellular G proteins.

The exposure of a GPCR to agonist produces rapid attenuation of its signaling ability that involves uncoupling of the receptor from its cognate heterotrimeric G-protein. The cellular mechanism mediating agonist-specific or homologous desensitization is a two-step process in which agonist-occupied receptors are phosphorylated by a G protein-coupled receptor kinases (GRKs) and then bind an arrestin protein.

It has been discovered that after agonists bind GPCRs, G-protein coupled receptor kinases (GRKs) phosphorylate intracellular domains of GPCRs. After phosphorylation, an arrestin protein associates with the GRK-phosphorylated receptor and uncouples the receptor from its cognate G protein. The interaction of the arrestin with the phosphorylated GPCR terminates GPCR signaling and produces a non-signaling, desensitized receptor.

The arrestin bound to the desensitized GPCR targets the GPCR to clathrin-coated pits for endocytosis (i.e., internalization) by functioning as an adaptor protein, which links the GPCR to components of the endocytic machinery, such as adaptor protein-2 (AP-2) and clathrin. The internalized GPCRs are dephosphorylated and are recycled back to the cell surface desensitized. The stability of the interaction of arrestin with the GPCR is one factor which dictates the rate of GPCR dephosphorylation, recycling, and resensitization. The involvement of GPCR phosphorylation and dephosphorylation in the desensitization process has been exemplified in U.S. Ser. No. 09/993,844, filed Nov. 5, 2001, the disclosure of which is hereby incorporated by reference in its entirety.

The abnormal regulation of hormones that bind to G protein-coupled receptors underlies the pathogenesis of many diseases. The ability to measure serum and tissue levels of these regulators, while clinically and scientifically desirable, is presently limited to very specialized biochemical and immunochemical assays. The present invention provides generalized methods that evaluate a process common to GPCR activity, providing useful methods for the screening and diagnosis of GPCR-based disease. Additionally, the present invention provides a method of screening a sample, biological, environmental, or the like, for compounds which alter GPCR ligands.

The present inventors have harnessed this desensitization process common among GPCRs to develop a method of detecting the presence of a GPCR ligand in a biological or environmental solution. The present invention is related to methods of detecting the concentration, presence, absence, or altered concentration of GPCR agonists, ligands, antagonists, or related compounds in a biological sample, environmental sample such as water or soil, or other solution.

In one embodiment of the present invention, a biosensor is employed. The biosensor is a host cell or cells that include a GPCR and arrestin. In the presence of agonist, the arrestin binds the GPCR, and the GPCR is internalized. Preferably, this process is visualized by the detection of the arrestin or the GPCR. The biosensor may be used to detect the presence of an agonist in a test sample, such as a biological or environmental sample. The detection of agonists by biosensors of the present invention is useful in disease diagnosis, as well as in the detection of dangerous compounds in the environment.

The present inventors determined that the host cells including a GPCR and arrestin could be used to detect various ligands of a GPCR in a test sample. The biosensors of the present invention are useful for the detection of multiple bioactive isoforms of a ligand in a test sample. In U.S. Ser. No. 09/993,844 filed on Nov. 5, 2001, U.S. Ser. No. 10/054,616 filed on Jan. 22, 2002, and U.S. Ser. No. 10/101,235 filed on Mar. 19, 2002, which are hereby incorporated by reference in their entirety, cells expressing GPCRs and arrestin-GFP were used for the identification of a ligand, or antagonist, in a solution. In the present invention, the present inventors determined that cells expressing GPCRs and arrestin-GFP were useful for the detection of all bioactive isoforms of a ligand in the test sample, not just one ligand isoform. The present invention is useful for determining the concentration of all bioactive isoforms, not just one, of a ligand in a test sample.

In a preferred embodiment of the present invention, the test samples are heterogeneous. They may include various proteins and compounds. They may include multiple isoforms of a GPCR ligand.

The methods of the present invention present a number of advantages over current methods of detecting GPCR ligands in a test sample. The present methods are highly sensitive and specific. In the methods of the present invention, the GPCRs detect the various bioreactive ligand species in the sample, as opposed to other antibody-based methods, such as RIA, which detect only the ligand species with the reactive epitope. Additionally, the present method broadly applies to all GPCRs and is easily adapted for the various GPCRs.

A particular strength of the bioassay of the present invention is the virtual elimination of all false positive results. In a standard RIA any epitope capable of interacting with antisera could produce a positive reading. In contrast, the bioassay of the present invention, employing a GPCR, measures bioactivity rather than immunoreactivity. A ligand-receptor interaction that results in arrestin translocation is biologically relevant regardless of the immunological properties of the ligand. The ability to determine the degree of biological activity in the absence of radioactivity in a serum or tissue sample is a much needed laboratory addition for identifying disease pathology or predicting potential complications arising from abnormal hormone concentrations.

As opposed to other methods, the methods of the present invention are not subject to cross-reactivity with other compounds in the sample. The methods of the present invention are specific for the detection of GPCR ligands which are biologically active and do not cross-react with compounds in the sample which are not biologically active. Additionally, as opposed to the methods of the present inventions, other methods of detection do not have the ability to detect all of the bioactive isoforms of a ligand in a test sample.

Detecting Gastrin

A number of disease conditions are associated with abnormal regulation of GPCR ligand concentration. The present invention provides a method of detecting the presence, absence, concentration, or change in concentration of a GPCR ligand. Using such methods, the present invention provides methods of diagnosing a disease or a disease-causative state.

Clinical assays are often hampered by an inability to diagnose disease when it exists, a false negative result, or inappropriately indicating pathology, a false positive result. The methods of the present invention are resistant to false negative results because the methods involve the detection of all bioactive isoforms of the GPCR ligands. For example, the present inventors have determined that the methods of the present invention detected all bioactive isoforms of gastrin rather than just immunoactive forms of gastrin, and the methods are resistant to false negative results. This is particularly evident from the robust response observed in response to pentagastrin, a potent receptor agonist that is not detectable by the immunological assays. The experimental sensitivity for detecting endogenous ligand using hG17 as a standard was approximately 100-200 μM (200-400 pg/ml of hG17), a range approximating the upper limit of normal as defined by RIA (<200 pg/ml, approximately 50 to 90 pM). Various strategies to increase the sensitivity include blocking receptor recycling to allow for more internalization, sample concentration, or receptor modification by mutagenesis to increase affinity.

One embodiment of the present invention is the diagnosis of hypergastrinemia by analyzing the location of the CCK-B GPCR after exposure to gastrin in a test sample. Cells are provided that express the CCK-B GPCR and arrestin. The GPCR or arrestin may be detectably labeled. These cells are exposed to a test sample, and subsequent changes in the location of the GPCR or arrestin are analyzed. Such analyses may be quantitative and may indicate the concentration of gastrin, or biologically-active isoforms, in a test sample. As discussed below, the gastrin concentration may be indicative of a disease condition, such as hypergastrinemia.

Gastrin is a ligand which binds a GPCR, and is the major hormonal regulator of gastric acid secretion. Two major forms of gastrin are secreted (Gastrin-34 and Gastrin-17), however, all gastrins have an amidated tetrapeptide (Trp-Met-Asp-Phe-$NH_2$) at the carboxyl terminus, which imparts full biological activity. The vast majority of gastrin is produced in endocrine cells of the gastric antrum. Progastrin is known to be expressed in a number of mammalian tissues: the gastrin antrum, jejunum, ileum, colon, and pancreas of the gastrointestinal tract; the ovaries, testicles, and spermatozoa of the genital tract; the cerebellum, vagus nerve, hypothalamus, pituitary, and adrenal medulla of the neuroendocrine tissue; and the bronchial mucosa of the respiratory tract, although it may be expressed in other tissues as well.

Gastrin is a member of the cholecystokinin (CCK) family of gastrointestinal (GI) peptides, hormones that bind to CCK-A and CCK-B receptors, GPCRs found in the GI tract and brain. The cloning and characterization of the CCK-B receptor as a typical heptahelical G protein-coupled receptor (GPCR) has provided a valuable tool in the study of gastrin. The human CCK-B receptor has a nanomolar affinity for gastrin and cholecystokinin. The circulating levels of CCK are beyond detection by conventional radioimmunoassay (RIA), but the major biologically active forms of gastrin, gastrin-17 and gastrin-34 that are secreted into the blood are immunologically detectable by RIA. Presently, serum gastrin measurements are performed by radioimmunoassay using antibodies directed against one or more distinct gastrin isoforms. Occasionally, antisera may show cross-reactivity to gastrin precursors or other serum proteins that vary in their biological potency or have no biological consequence related to CCK-B receptor signaling. Alternatively, patients have presented with symptoms of hypergastrinemia, and/or known gastrin-secreting tumors where the RIA determinations of serum gastrin were normal. This has lead to the hypothesis that certain tumors may produce non-RIA detectable gastrin variants.

The two major biologically active forms of gastrin, 17 and 34 amino acids in length, are produced by enzymatic digestion of preprogastrin and secreted into the blood by gastric antral G cells. Gastrin primarily regulates the release of stomach acid and the growth of GI mucosa, and its oversecretion is associated with enterochromaffin cell hyperplasia and tumors.

In the endoplasmic reticulum, the signal peptide of preprogastrin is cleaved resulting in progastrin. Further enzymatic modification of progastrin in the Golgi generates products which are packaged into secretory granules. A number of secretory granule products are derived from preprogastrin: progastrin, glycine-extended gastrin-17, glycine-extended gastrin-34, gastrin-71, gastrin-34, gastrin-17, and gastrin-6.

Hypergastrinemia is associated with GI malignancies and consequently serum gastrin levels are routinely measured in clinical practice. Hypergastrinemia may occur in pathophysiologic states and serum gastrin levels can also become elevated in patients on prolonged acid suppressive medications. Presently, serum gastrin measurements are performed by radioimmunoassay (RIA), using antibodies directed against one or more distinct gastrin isoforms. Occasionally, antisera may show cross-reactivity to gastrin precursors or other serum proteins that vary in their biological potency or have no biological consequence related to CCK-B receptor signaling. Alternatively, patients have presented with symptoms of hypergastrinemia, and/or known gastrin-secreting tumors where the RIA determinations of serum gastrin were normal. This has lead to the hypothesis that certain tumors may elaborate non-RIA detectable gastrin variants.

Detecting Acetylcholine

In another embodiment of the present invention, a number of chemical/biological agents of interest to the military and civilian communities may be sensed readily by the described sensors. The present invention may be used to detect biological agents, toxins, neurotoxins, nerve gases, and the like. The ability to rapidly and accurately detect and quantify biologically relevant molecules with high sensitivity is a central issue for medical technology, national security, public safety, environmental safety and civilian and military medical diagnostics.

Such a biosensor for the detection of agents, such as bioterrorism agents, in the environment provides a number of advantages over present detection methods. First, the assay is sensitive and, since based on the biological activity of the ligand, detects the presence of any bioactive variants of the ligand of interest. Secondly, the assay is quantitative and can detect altered or minimal concentrations of the ligand in the sample. The assay also can be monitored in a continuous fashion. Additionally, sample preparation is quite straightforward: a sample need only be suspended in an aqueous solution for detection.

A number of neurotoxins including sarin and organophosphate insecticides, for example diazinon, inhibit acetylcholinesterase, an enzyme which inactivates the neurotransmitter acetylcholine. In vivo, compounds which decrease acetylcholine esterase activity result in an increase in the concentration of acetylcholine in the synaptic cleft, producing excessive nerve excitation. Levels of acetylcholine in a test sample can be used to monitor acetylcholinesterase activity, and detect the presence of acetylcholinesterase inhibitors. One aspect of the present invention is the use of a single cell biosensor expressing the muscarinic receptor as a method of detecting the presence of acetylcholine esterase inhibitors in the environmental or a biological sample.

Another embodiment of the invention pertains to field-testing of environmental conditions. Automated sensing of environmental conditions, including the presence of natural chemicals, industrial wastes, and biological/chemical warfare agents is possible using an embodiment of the invention. Uploading of test results via radio transmission may provide remote sensing capabilities, and may provide response capabilities through human or central computer directed action. Response instructions may then be downloaded either to the sensing site or to another strategic response position. Such a system may be useful, for example, in determining the presence of toxins in a public water supply, and the subsequent centralized-directed cessation of water flow from the supply pool.

Described above are embodiments of the present invention employing the CCK-B or the muscarinic GPCRs. Additionally, the present invention encompasses biosensors employing any GPCR. By fluorescence microscopy, GPCR association with arrestin and subsequent internalization at least 40 different GPCRs using fusion proteins between arrestin and a green fluorescent protein is possible (FIG. 2). Each of these cells, as well as other like cells, is a useful biosensor of the present invention.

Methods of the Present Invention

The present invention provides highly specific, sensitive, generalized, and quantitative methods of analyzing the presence of GPCR-binding compounds in samples.

One embodiment of the present invention is a method of detecting a GPCR ligand in a test sample. Most preferably, this method comprises the steps of (a) providing a cell including a GPCR and an arrestin; (b) exposing the cell to the test sample; and (c) determining the cellular distribution of the GPCR or arrestin in the presence of the test sample, wherein the test sample is, or is derived from, a biological sample or an environmental sample.

In a preferred embodiment, the cellular distribution of the GPCR or arrestin in the presence of the test sample is compared to the cellular distribution of the GPCR or arrestin in the absence of the test sample. Different concentrations of the test sample may be analyzed. The cellular distribution may be determined at different time points after exposure to the test sample.

In one embodiment of the present invention, the GPCR or arrestin is detectably labeled, other endogenous molecules are detectably labeled, or exogenous molecules are detectably labeled. The distribution of the detectably labeled molecules represents the cellular distribution of the GPCR or arrestin. The distribution of the GPCR or arrestin may indicate the extent to which the GPCR is internalized. The cellular distribution of the detectably labeled molecule may be quantified.

In one embodiment of the present invention, a sample may include a known concentration of the ligand. By comparing the cellular distribution of the detectably labeled molecule in the presence of the test sample to the distribution in the presence of known concentrations of ligand, the concentration of ligand in the test sample may be determined.

The test sample may be a biological sample or an environmental sample. The biological sample may be or may be derived from serum, tissue, blood, or urine.

In one embodiment, the GPCR is CCK-B or CCK-A. The ligand may be gastrin, preprogastrin, cleaved preprogastrin, gastrin-34, gastrin-17, pentagastrin, progastrin, glycine-extended gastrin-17, glycine-extended gastrin-34, gastrin-71, or gastrin-6. In one embodiment, the GPCR is a muscarinic receptor. The ligand may be acetylcholine.

In a preferred embodiment, the labeled molecule is localized in the cytosol, clathrin-coated pits, the plasma membrane, endocytic vesicles, or endosomes. An increase in the local concentration of the labeled molecule results in a local increase in signal intensity. The signal intensity in the plasma membrane, clathrin-coated pits, endocytic vesicles, or endosomes may be greater than the signal intensity in the cytosol. The local signal intensity may be increased or decreased in the presence of increased or decreased amounts of a compound, such as a ligand, agonist, or antagonist.

In a preferred embodiment, the concentration of a ligand in the test sample indicates a disease state. The concentration of the ligand in the test sample may indicate the presence of a compound in the test sample that alters the ligand concentration. The ligand concentration may indicate the presence of a compound in the test sample that modifies acetylcholine or inhibits acetylcholinesterase.

In a preferred embodiment, the detectable molecule is a radioisotope, an epitope tag, an affinity label, an enzyme, a fluorescent group, or a chemiluminescent group. In one embodiment, a molecule may be detectably labeled due to its interaction with another molecule which is detectably labeled.

One embodiment of the present invention is a method of monitoring a GPCR ligand in mammals, wherein the analysis of the ligand concentration in a test sample is based on the binding of the ligand to the GPCR. This method may be used to monitor a clinical condition and/or may indicate the presence of a disease state. The clinical condition may indicate that the subject has a disorder or is at risk for developing a disorder. The clinical condition may be gastrointestinal cancer, hypergastrinemia, atrophic gastritis, gastric ulcers, or malignant tumors.

Arrestin coupled to a detectable molecule may be detected and monitored as it functions in the GPCR pathway. The location of the arrestin may be detected, for example, evenly distributed in the cell cytoplasm, concentrated at a cell membrane, concentrated in clathrin-coated pits, localized in endocytic vesicles or endosomes, and the like. The proximity of arrestin to a GPCR may be monitored, as well as the proximity to any other cell structure.

Preferably, the arrestin, the GPCR, and/or the arrestin/GPCR complex may be detected in endocytic vesicles or endosomes. The arrestin, the GPCR, and/or the arrestin/GPCR complex thus may be detected in endocytic vesicles or endosomes absence of agonist. The association of arrestin with a GPCR in endocytic vesicles or endosomes may give a strong, readily recognizable signal that persists for extended periods of time. Under magnification of 40× objective lens, the signal may be doughnut-like in appearance. The signal resulting from the compartmentalization of arrestin and GPCR colocalized in endocytic vesicles or endosomes is typically easy to detect. Similarly, blocking this association is easy to detect. Examples of detection methods are described herein. Such methods include, for example, polarization microscopy, BRET, FRET, evanescent wave excitation microscopy, and standard or confocal microscopy.

One embodiment of the present invention is a method of measuring the gastrin concentration in a test sample. By employing cell lines permanently expressing the gastrin receptor (CCK-B) and a fusion protein consisting of β-arrestin 2 and green fluorescent protein (GFP), the present inventors have constructed a single cell biosensor for the measurement of serum gastrin. The quantitative redistribution of arrestin-GFP in response to agonist-activated gastrin receptors was measured by analysis of cell images obtained by fluorescence confocal microscopy, and provided a sensitive and specific determination of receptor activation. Such a single cell biosensor is a practical means to measure the bioactive serum concentration of gastrin, allowing the diagnosis of hypergastrinemia.

In one embodiment, the presence of GPCR ligand in the test sample indicates the presence of a disease, that a subject has a disorder, or is at risk for getting a disorder. Alternatively, the absence, altered concentration, or other alteration of the GPCR ligand may indicate the presence of a disease, that a subject has a disorder, or is at risk for getting a disorder.

In one embodiment, the analysis of the GPCR ligand indicates the presence, absence, enhancement, inhibition, or other alteration of a compound that alters the GPCR ligand. The analysis may indicate the presence, absence, altered concentration, or other alteration of the ligand. The compound that alters the GPCR ligand may be an enzyme, an inhibitor, an activator, a small molecule, or other compound that directly affects the GPCR ligand. The compound that alters the GPCR ligand may be an enzyme, an inhibitor, an activator, a small molecule, or other compound that indirectly affects the GPCR ligand.

In a specific embodiment, the GPCR is the muscarinic receptor and the method of determining the concentration of acetylcholine in a test sample. By employing cell lines transiently transfected with the muscarinic receptor and a fusion protein consisting of β-arrestin 2 and green fluorescent protein, the present inventors have constructed a single cell biosensor for the measurement of acetylcholine in a sample.

Acetylcholine, the ligand of the muscarinic receptor, is altered by acetylcholinesterase. In the presence of acetylcholinesterase, the concentration of acetylcholine in a test sample is decreased. A decrease in the amount of acetylcholine in a test sample decreased the amount of internalization of the muscarinic receptor, as visualized by the decreased internalization of the arrestin-GFP conjugate.

An additional embodiment of the present invention is related to methods of increasing the sensitivity of the above methods. In one aspect, as described in U.S. Ser. No. 09/993,844 filed on Nov. 5, 2001, which is hereby incorporated by reference in its entirety, the GPCR itself may be modified in its C-terminal tail such that it has enhanced phosphorylation sites. The sensitivity of the assay may also be increased with GRK over-expression. The biosensor may be exposed to the test sample for longer periods of time, or at increased concentrations, in order to increase the signal.

Expression of the Proteins

Another feature of this invention is the expression of the DNA sequences encoding a GPCR and/or arrestin in a cell to form a biosensor, as disclosed herein. As is well known in the art, DNA sequences may be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences. Useful expression vectors, for example, may consist of segments of chromosomal, non-chromosomal and synthetic DNA sequences. Suitable vectors include derivatives of SV40 and known bacterial plasmids, e.g., E. coli plasmids col EI, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences— sequences that control the expression of a DNA sequence operatively linked to it—may be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences. These hosts may include well known eukaryotic and prokaryotic hosts, such as strains of E. coli, Pseudomonas, Bacillus, Streptomyces, fungi such as yeasts, plant cells, nematode cells, and animal cells, such as HEK-293, CHO, RI.I, B-W and L-M cells, African Green Monkey kidney cells (e.g., COS 1, COS 7, BSC1, BSC40, and BMT10), insect cells (e.g., Sf9), and human cells and plant cells in tissue culture. However, mammalian cells are preferred for creating the biosensors of the invention.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences on fermentation or in large scale animal culture.

As mentioned above, a DNA sequence encoding a modified GPCR can be prepared synthetically rather than cloned. The DNA sequence can be designed with the appropriate codons for the GPCR amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Synthetic DNA sequences allow convenient construction of genes which will express GPCR analogs or "muteins". Alternatively, DNA encoding muteins can be made by site-directed mutagenesis of native or modified GPCR genes or cDNAs, and muteins can be made directly using conventional polypeptide synthesis.

A general method for site-specific incorporation of unnatural amino acids into proteins is described in Christopher J.

Noren, Spencer J. Anthony-Cahill, Michael C. Griffith, Peter G. Schultz, Science, 244:182-188 (April 1989). This method may be used to create analogs with unnatural amino acids.

Conjugates

The cells used in the methods of assaying of the present invention may comprise a conjugate of an arrestin protein and a detectable molecule, a conjugate of a GPCR and a detectable molecule, a conjugate of any member of a GPCR/arrestin complex and a detectable molecule, a conjugate of a detectable molecule and a molecule that interacts with any member of a GPCR/arrestin complex, and the like. The detectable molecule allows detection of molecules interacting with the detectable molecule, as well as the molecule itself.

All forms of arrestin, naturally occurring and engineered variants, including but not limited to, visual arrestin, β-arrestin 1 and β-arrestin 2, may be used in the present invention. GPCRs may interact to a detectable level with all forms of arrestin.

Detectable molecules that may be used include, but are not limited to, molecules that are detectable by spectroscopic, photochemical, biochemical, immunochemical, electrical, radioactive, and optical means, including but not limited to bioluminescence, phosphorescence, and fluorescence. These detectable molecules should be a biologically compatible molecule and should not compromise the biological function of the molecule and must not compromise the ability of the detectable molecule to be detected. Preferred detectable molecules are optically detectable molecules, including optically detectable proteins, such that they may be excited chemically, mechanically, electrically, or radioactively to emit fluorescence, phosphorescence, or bioluminescence. More preferred detectable molecules are inherently fluorescent molecules, such as fluorescent proteins, including, for example, Green Fluorescent Protein (GFP). The detectable molecule may be conjugated to the arrestin protein by methods as described in Barak et al. (U.S. Pat. Nos. 5,891,646 and 6,110,693). The detectable molecule may be conjugated at the front-end, at the back-end, or in the middle.

The GPCRs may also be conjugated with a detectable molecule. Preferably, the carboxyl-terminus of the GPCR is conjugated with a detectable molecule. If the GPCR is conjugated with a detectable molecule, proximity of the GPCR with the arrestin may be readily detected. In addition, if the GPCR is conjugated with a detectable molecule, compartmentalization of the GPCR with the arrestin may be readily confirmed. The detectable molecule used to conjugate with the GPCRs may include those as described above, including, for example, optically detectable molecules, such that they may be excited chemically, mechanically, electrically, or radioactively to emit fluorescence, phosphorescence, or bioluminescence. Preferred optically detectable molecules may be detected by immunofluorescence, luminescence, fluorescence, and phosphorescence.

For example, the GPCRs may be antibody labeled with an antibody conjugated to an immunofluorescence molecule or the GPCRs may be conjugated with a luminescent donor. In particular, the GPCRs may be conjugated with, for example, luciferase, for example, *Renilla* luciferase, or a rhodamine-conjugated antibody, for example, rhodamine-conjugated anti-HA mouse monoclonal antibody. Preferably, the carboxyl-terminal tail of the GPCR may be conjugated with a luminescent donor, for example, luciferase. The GPCR, preferably the carboxyl-terminal tail, also may a be conjugated with GFP as described in L. S. Barak et al. Internal Trafficking and Surface Mobility of a Functionally Intact β2-Adrenergic Receptor-Green Fluorescent Protein Conjugate, Mol. Pharm. (1997) 51, 177-184.

Cell Types and Substrates

The cells of the present invention express at least one GPCR, and arrestin, wherein at least one of the molecules is detectably labeled. Cells useful in the present invention include eukaryotic and prokaryotic cells, including, but not limited to, bacterial cells, yeast cells, fungal cells, insect cells, nematode cells, plant cells, and animal cells. Suitable animal cells include, but are not limited to, HEK cells, HeLa cells, COS cells, U2OS cells and various primary mammalian cells. An animal model expressing a conjugate of an arrestin and a detectable molecule throughout its tissues or within a particular organ or tissue type, may also be used in the present invention.

A substrate may have deposited thereon a plurality of cells of the present invention. The substrate may be any suitable biologically substrate, including but not limited to, glass, plastic, ceramic, semiconductor, silica, fiber optic, diamond, biocompatible monomer, or biocompatible polymer materials.

Methods of Detection

Methods of detecting the intracellular location of the detectably labeled arrestin, the intracellular location of a detectably labeled GPCR, or interaction of the detectably labeled arrestin, or other member of GPCR/arrestin complex with a GPCR or any other cell structure, including for example, the concentration of arrestin or GPCR at a cell membrane, colocalization of arrestin with GPCR in endosomes, and concentration of arrestin or GPCR in clathrin-coated pits, and the like, will vary dependent upon the detectable molecule(s) used.

One skilled in the art readily will be able to devise detection methods suitable for the detectable molecule(s) used. For optically detectable molecules, any optical method may be used where a change in the fluorescence, bioluminescence, or phosphorescence may be measured due to a redistribution or reorientation of emitted light. Such methods include, for example, polarization microscopy, BRET, FRET, evanescent wave excitation microscopy, and standard or confocal microscopy.

In a preferred embodiment arrestin may be conjugated to GFP and the arrestin-GFP conjugate may be detected by confocal microscopy. In another preferred embodiment, arrestin may conjugated to a GFP and the GPCR may be conjugated to an immunofluorescent molecule, and the conjugates may be detected by confocal microscopy. In an additional preferred embodiment, arrestin may conjugated to a GFP and the carboxy-terminus of the GPCR may be conjugated to a luciferase and the conjugates may be detected by bioluminescence resonance emission technology. In a further preferred embodiment arrestin may be conjugated to a luciferase and GPCR may be conjugated to a GFP, and the conjugates may be detected by bioluminescence resonance emission technology. The methods of the present invention are directed to detecting GPCR activity. The methods of the present invention allow enhanced monitoring of the GPCR pathway in real time.

In a preferred embodiment, the localization pattern of the detectable molecule is determined. In a further preferred embodiment, alterations of the localization pattern of the detectable molecule may be determined. The localization pattern may indicated cellular localization of the detectable molecule. Certain methods of detection are described in U.S. Ser. No. 10/095,620, filed Mar. 12, 2002, which claims priority to U.S. Provisional Patent Application No. 60/275,339, filed Mar. 13, 2001, the contents of which are incorporated by reference in their entirety.

Molecules may also be detected by their interaction with another detectably labeled molecule, such as an antibody.

Test Kits

The present invention includes test kits for analysis of test samples. Most preferably, the test kits would be useful for determining the GPCR ligand concentration in a biological or environmental sample. Even more preferably, the test kit would include a host cell expressing a GPCR and arrestin, and method of determining ligand concentration in sample.

EXAMPLES

The invention will be further explained by the following illustrative examples which are intended to be non-limiting.

Example 1

Materials & Methods

Human Embryonic Kidney Cells (HEK-293) were obtained from the American Type Culture Collection (ATCC, Manassas, Va.). Media, fetal bovine serum (FBS), and antibiotics were purchased from MediaTech (Herndon, Va.) and Gibco Invitrogen Corp (Carlsbad, Calif.). 96 well glass plates were obtained from Whatman (Clifton, N. J.) and binding resins from BioRad Laboratories (Hercules, Calif.). The CCK-A receptor antagonist devazepide and a specific CCK-B receptor antagonist were used. Pentagastrin was obtained from Sigma.

Membrane Preparation/Binding—All steps were performed at 4° C. Membrane binding was performed in triplicate as described in Shetzline et al., *J. Biol. Chem.* 273:6756-6752 (1998). Membrane fractions were assayed immediately or stored at −80° C. Saturation or competition binding was performed with [$^3$H]CCK-8 polypeptide (Peninsula Labs, San Carlos, Calif.), with non-specific binding determined in the presence of 1 µM hG17. Competitive binding was performed using hG17. Data were analyzed using Graph Pad-Prism.

Cloning of the Human Gastrin Receptor: The human gastrin/CCK-B receptor cDNA was amplified from a human brain cDNA library (Clontech) using two oligonucleotide primers matching the 5' and 3' ends of the coding region, a sense oligonucleotide (5'-GCGCCC GCTAGCACCGCCATGGAGCTGCTAAAGCTGAACCG-G) (SEQ ID NO: 17) with a NheI restriction site, and an antisense oligonucleotide (5'-GCGCCC GGTACCTCAGCCAGGGCCCAGTGTGCTGAT) (SEQ ID NO: 18) with a KpnI restriction site. The 1.4 kb amplified CCK-B receptor DNA band was subcloned into the pcDNA3.1-ZEO(−) expression vector (Invitrogen) at NheI and KpnI and verified on an ABI 377 fluorescent scanner.

Cell Culture and Transfection: Transient transfection in HEK-293 cells was done as described in Walker et al., *J. Biol. Chem.* 274:31515-23.

Inositol Phosphate Determination—HEK 293 cells expressing the CCK-B receptors were plated into 12-well plates coated with 25 µg/ml Poly-D-Lysine (Sigma Cat# P-6407, St. Louis, Mo.) and incubated overnight at 37° C. in MEM containing 10% FBS (fetal bovine serum). They were next placed for 24 hours in labeling media (1 µCi/0.5 mL/well of [$^3$H]inositol in 5% FBS/MEM/Gentamicin), washed with MEM, 20 mM HEPES, pH 7.40, 20 mM LiCl for 5 minutes at 37° C., and treated with agonist. The reactions were stopped by addition of 500 µL of ice-cold 0.8 M HClO$_4$, the cells gently agitated at 4° C. for 30-60 minutes and the cell lysate then added to polypropylene tubes. 200 µL of neutralizing solution (0.72 M KOH/0.6 M KCO$_3$) was added to each tube and the tubes remained at 4° C. until analysis. BioRad AG-1X8 Resin (200-400 mesh) columns (BioRad Econo-Pac) were prepared with 1 ml of 50% slurry each in order to assay IP3 activity. Each column was washed twice with 10 ml of 18 megaohm deionized water, 800 µL of lysate was added, and after 5-10 minutes the columns were again washed twice with 10 mL of water. Samples were eluted into scintillation vials containing 15 mL of Lefko-Fluor (Research Products International Mt. Prospect, Il) using 3.5 mL of a 1 M ammonium formate/0.1 M formic acid solution. Fifty µL lysate samples corresponding to each fraction were also counted to determine total radioactivity uptake per sample.

Fluorescence Confocal Microscopy and Data Analysis: The measurements of arrestin-GFP translocation for quantitative determinations of dose responses or of patient serum levels were done in the following manner. Cells permanently expressing the human CCK-B receptor and arrestin-GFP were seeded at 20,000 cells per well in 96 well, glass bottomed plates in 200 µL of MEM supplemented with 10% fetal bovine serum. 100 µl was removed and replaced by media containing a known concentration of hG17 peptide, pentagastrin, or a known volume of patient serum. Fluorescence cell images were obtained with a Zeiss LSM-510 confocal microscope. The dynamic translocation of arrestin-GFP over 5 minutes was analyzed as described. Static cell images obtained after one-two hour incubations were analyzed using the computer program IP LABS (Scanalytics, Fairfax, Va. 22031).

The analysis of translocation proceeded as follows. An average and standard deviation of pixel intensity was determined for images of untreated cells containing arrestin-GFP. An intensity corresponding to 3 standard deviations above the mean for these cells was set as the threshold to define translocation. To determine the subset of pixels representing translocated arrestin-GFP, only pixels that had at least one neighbor above this threshold were counted. This second restriction was set to eliminate noise. The measured amount of translocation, TI, in an image was then calculated to be sum of the intensities from pixels representative of translocation. The number of cells in an image could vary, but the total amount of fluorescence obtained from an image was independent of the distribution of chromophore and remained constant over time. To correct for the variation in the number of cells contained in different images, the calculated translocation for an image was normalized by the total image fluorescence, TF (i.e. sum of intensities for all pixels in the image). The computed translocation was defined as TI/TF. The mean intensity of the untreated cells was set to fall within the bottom 10% of the dynamic range of the microscope imaging system in order to avoid clipping the signal from areas with large amounts of receptor/arrestin-GFP complexes. Data are presented as mean±SEM.

Evaluation of the Signal to Noise (See FIG. 7) In order to evaluate the signal/noise ratio, the following two assumptions were made about the experimental system; (1) the sum of the intensities over all pixels, is independent of time and redistribution of βarrestin2-GFP and (2) the intensity distribution of cell fluorescence is gaussian and is given by the normalized probability distribution:

$$P(I) = \frac{2}{\sigma \cdot \sqrt{\pi} \cdot [1+erf(I_o/\sigma)]^{1/2}} \exp\left(-\frac{(I-I_o)^2}{\sigma^2}\right); \quad \int_0^\infty P(I)dI = 1.$$

I is the intensity, $I_o$ is the mean intensity, $\sigma$ is the standard deviation, exp(z) is the exponential function, and erf(z) is the error function $$erf(z) = \frac{2}{\sqrt{\pi}} \cdot \int_0^z \exp(-z^2) \cdot dz.$$

The threshold for measuring the signal from translocated βarrestin2-GFP is to be set to $I_o+j$ where $j=\beta \times \sigma$. The mean square deviation of intensity above this threshold in the absence of agonist is:

$$\langle \sigma^2 \rangle_j = \langle (I-(I_o+j))^2 \rangle_j = \int_{I_o+j}^\infty P(I)(I-(I_o+j))^2 dI,$$

where $$\sigma_N = \sqrt{\langle \sigma^2 \rangle_j} = \frac{\frac{\sigma}{\sqrt{2}} \left[(1-erf(\beta))(1+2\beta^2) - \frac{2\beta}{\sqrt{\pi}}\exp(-\beta^2)\right]^{1/2}}{[1+erf(I_o/\sigma)]^{1/2}}$$

A mean intensity of translocated β-arrestin2-GFP, $I_f$, can be determined over the subset of pixels, $N_a$ that exceed the threshold value of intensity $I_o+j$. $I_f$ results from an intensity contribution from translocated β-arrestin2-GFP and from untranslocated protein. It is related to the average intensity $I_o$ before translocation by:

$$I_f = \eta \cdot I_o \cdot \frac{N_b}{N_a} + (1-\eta) \cdot I_o,$$

$N_b$ is the number of pixels that image the cells prior to translocation, $I_o$ as defined above is their mean intensity, and h is the fraction of translocated receptors. The ratio $$\frac{N_b}{N_a}$$

represents the magnitude of the change in volume occupied by the βarrestin-GFP after translocation. The signal to noise ratio for a typical individual pixel that exceeds the threshold value can now be calculated as:

$$S/N = \frac{I_f - (I_o+\beta\cdot\sigma)}{\sigma_N} = \frac{\eta \cdot I_o \cdot \frac{N_b}{N_a} + (1-\eta)\cdot I_o - I_o - \beta\cdot\sigma}{\sigma_N},$$

which simplifies to:

$$S/N = \frac{\sqrt{2} \cdot [1+erf(I_o/\sigma)]^{1/2}}{\left[(1-erf(\beta))(1+2\beta^2) - \frac{2\beta}{\sqrt{\pi}}\exp(-\beta^2)\right]^{1/2}} \cdot \left\{\eta \cdot \frac{I_o}{\sigma} \cdot \left[\frac{N_b}{N_a}-1\right] - \beta\right\}$$

and $$\eta \cdot \frac{I_o}{\sigma} \cdot \left[\frac{N_b}{N_a}-1\right] - \beta > 0$$

For a homogeneous line of cells described by a narrow gaussian distribution of intensity the ratio of the mean intensity to its standard deviation $$\frac{I_o}{\sigma}$$

can be chosen greater than 4 by appropriately adjusting the range of the imaging system. The term $\sqrt{2}\cdot[1+erf(I_o/\sigma)]^{1/2}$ is then approximately equal to 2. The fraction of translocated receptors represented by the term h varies between 0 (no translocation) and 1 (100% translocation) whereas the ratio of the volumes (areas) due to redistribution of the arrestin-GFP $$\frac{N_b}{N_a}$$

may vary between 5-100 depending upon the imaging system and the identity of the cellular compartment containing the translocated arrestins (for example, membrane, coated pits, or endosomes). The term in the denominator $$\left[(1-erf(\beta))(1+2\beta^2) - \frac{2\beta}{\sqrt{\pi}}\exp(-\beta^2)\right]^{1/2}$$

equals 0.014 and 0.00070 for the threshold intensity set to b=2 and b=3 standard deviations above the mean intensity respectively. Therefore the signal to noise, S/N, can easily exceed $10^3$-$10^4$ for very homogeneous populations of cells with even minimal amounts of translocation $$\eta > \frac{\beta}{\frac{I_o}{\sigma}\cdot\left[\frac{N_b}{N_a}-1\right]} > \frac{3}{4\cdot 10} \cong 0.1.$$

Even though an inhomogeneous fluorescence distribution or background fluorescence will cause the intensity profile to depart from this ideal case, the analysis indicates that translocation by simply considering intensity changes can be a very sensitive method for evaluating receptor behavior. Moreover, the use of simple pattern recognition algorithms could provide even greater discrimination of translocated arrestin and be useful for cell populations that are not homogenous such as in transient transfections.

Patient serum collection and serum determination by RIA: The Institutional Review Board approved this study at Duke University Medical Center. Patient serum was obtained from patients scheduled for serum gastrin analysis as requested by their primary care provider. Patients signed informed consent and an additional sample of serum was drawn for use in this study. Conventional RIA determinations were performed at Mayo Medical Laboratories, Rochester, Minn.

Example 2

Cells Expressing the CCK-B Receptor and Arrestin-GFP Respond to the Presence of Synthetic Human Gastrin-17 Peptide (hG17): Determination of the Uniformity of Arrestin-GFP and CCK-B Receptor Expression in Cells by Flow Cytometry and Arrestin-GFP Translocation To simplify quantitative analysis of arrestin-GFP redistribution, cells which respond to ligand in an identical manner were established. In order to achieve a large degree of uniformity in receptor and arrestin expression among the entire cell population, an HEK-293 cell line permanently expressing the CCK-B receptor and arrestin-GFP was established. The degree of homogeneity of arrestin expression within the clone (Clone A) used in this study was determined by flow cytometry (FIG. 4A) and confirmed by fluorescence (FIG. 4B, Left Panel). The general ability of cells to respond to the presence of synthetic human gastrin-17 peptide (hG17) by redistributing arrestin-GFP is shown in FIG. 4B (Right Panel).

Figure 4B:
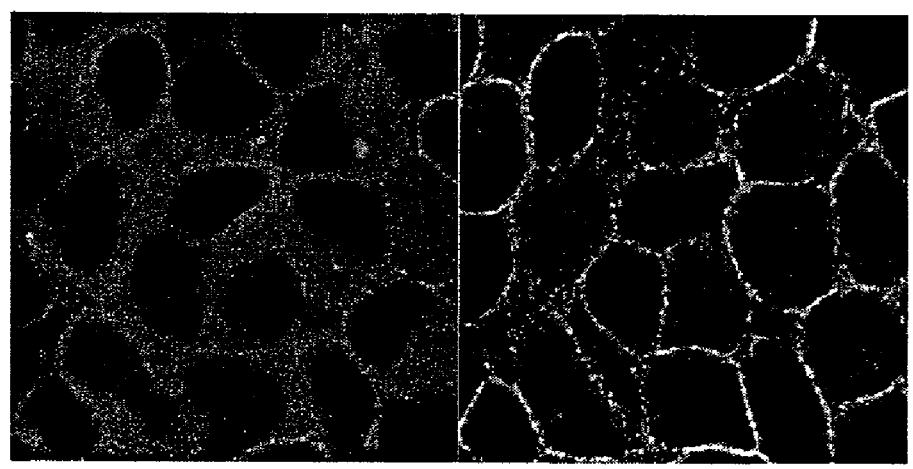
FIG. 4B shows fluorescence images of a field of cells from Clone A before (left panel) and after treatment (right panel) with 10 nM hG17 for 5 minutes at room temperature.

In FIG. 4A, the relative expression of arrestin-GFP in cells belonging to Clone A was determined using a Becton Dickenson FACScan flow cytometer. The x-axis is logarithmic in the relative cell intensity and the y-axis indicates the number of cells (Counts) at that intensity. Ninety-nine percent of the cell population was within the bounds of the bar seen above the intensity profile. FIG. 4B shows fluorescence images of a field of cells from Clone A before (left panel) and after treatment (right panel) with 10 nM hG17 for 5 minutes at room temperature.

Example 3

Characterization of Ligand Binding and Second Messenger Response

Clone A was further characterized my measuring the binding of the gastrin peptide agonists [$^3$H]-CCK8 and hG17, and determining the hG17-mediated second messenger response. Saturation binding with [$^3$H]-CCK8 showed that the cells expressed (14±1) pmol CCK-B receptor/mg cell protein and had an affinity for [$^3$H]-CCK8 of (9.0±1.6) nM (FIG. 5A). Human gastrin-17 stimulation of inositol phosphate (IP3) production yielded an $EC_{50}$=(3.2±0.7) nM (FIG. 5B). The inset in FIG. 5B shows the competitive displacement of [$^3$H]-CCK8 by hG17. The $EC_{50}$ was (28±5) nM and the Kd of hG17 for the CCK-B receptor was (17±3.5) nM.

FIG. 4 shows that 10 nM hG17 produced a measurable arrestin-GFP redistribution to the plasma membrane even after five minutes. After 30-60 minutes of exposure to hG17, endosomes containing arrestin-GFP became visible (FIG. 5C Upper Right Panel). This translocation was blocked completely by addition of 10 μM of the specific CCK-B receptor antagonist (FIG. 5C Lower Left Panel), but was not blocked by 10 μM of the closely related CCK-A receptor antagonist devazepide (FIG. 5C Lower Right Panel). The data in FIG. 5C confirm that the CCK-B receptor is a class B GPCR, since it promotes arrestin internalization into endosomes.

FIG. 5A shows that cells from Clone A were incubated with increasing concentrations of [$^3$H]CCK-8 in order to determine the average CCK-B receptor expression per cell and the receptor affinity for [$^3$H]CCK-8. Total binding of [$^3$H]CCK-8, □; specific binding of [$^3$H]CCK-8, ■; non-specific binding in the presence of excess (1 μM) unlabeled hG17, ○. In FIG. 5B, Clone A cells were exposed to increasing concentrations of hG17 peptide in order to evaluate the IP3 second messenger response. The inset shows the competitive displacement of [$^3$H]CCK8 by hG17 from this cell line. Data are presented as mean±SEM. FIG. 5C shows the fluorescence images of cells from Clone A that were treated with vehicle (upper left panel), or treated for one hour with 10 nM of the agonist hG17 (upper right panel), or with 10 nM hG17 plus 1 μM of the CCK-A antagonist devazepide (L-364,718, lower left panel); or with 10 nM hG17 plus 1 μM, of the CCK-B antagonist (lower right panel).

Example 4

Dose Response to hG17 and Analysis of Serum Samples from a Patient with Hypergastrinemia Using increasing concentrations of hG17, the time-dependent loss of cytoplasmic arrestin-GFP was measured in order to determine if the pharmacology of arrestin redistribution correlated with that of IP3 production. Sequential fluorescence images of ligand-treated cells grown in 96 well plates were obtained in 30-second intervals over 5 minutes by confocal microscopy and analyzed by measuring the loss of cytosolic fluorescence. The time and dose dependence of arrestin redistribution for increasing concentrations of hG17 is plotted in FIG. 6A. From this data a dose response curve was calculated which resulted in an $EC_{50}$ for translocation of 4.2±1.5 nM (FIG. 6B), in agreement with the IP3 results.

Figure 6A:
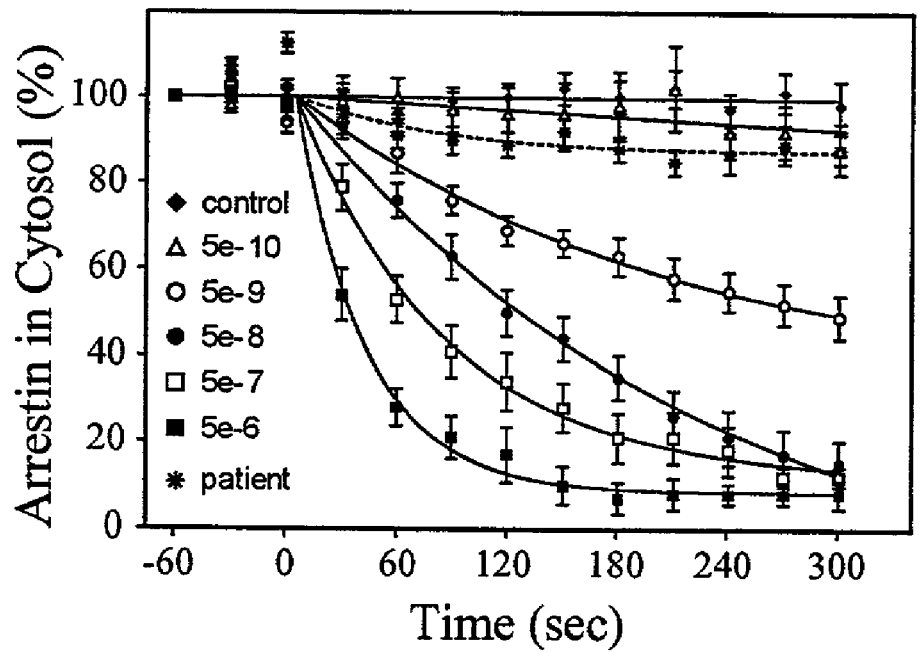
FIG. 6A is a representative experiment depicting the arrestin-GFP translocation of Clone A cells that were exposed to various concentrations of hG17 for 5 minutes.
Figure 6B:
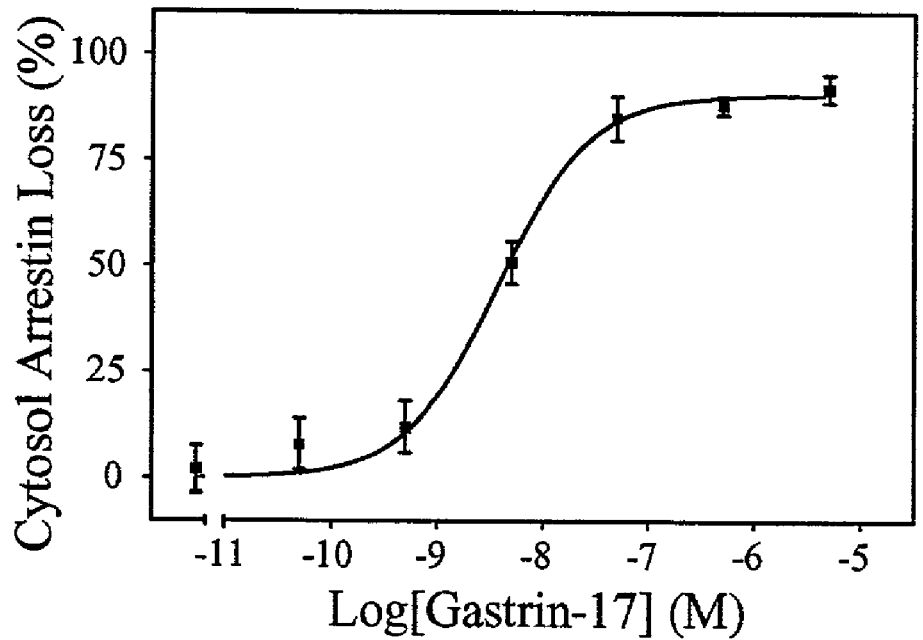
In FIG. 6B, the fractional amount of arrestin-GFP lost after 5 minutes from the cell cytosol was used to generate a sigmoid dose response curve for the increasing concentrations of hG17 shown in the graph in A.
Figure 6C:
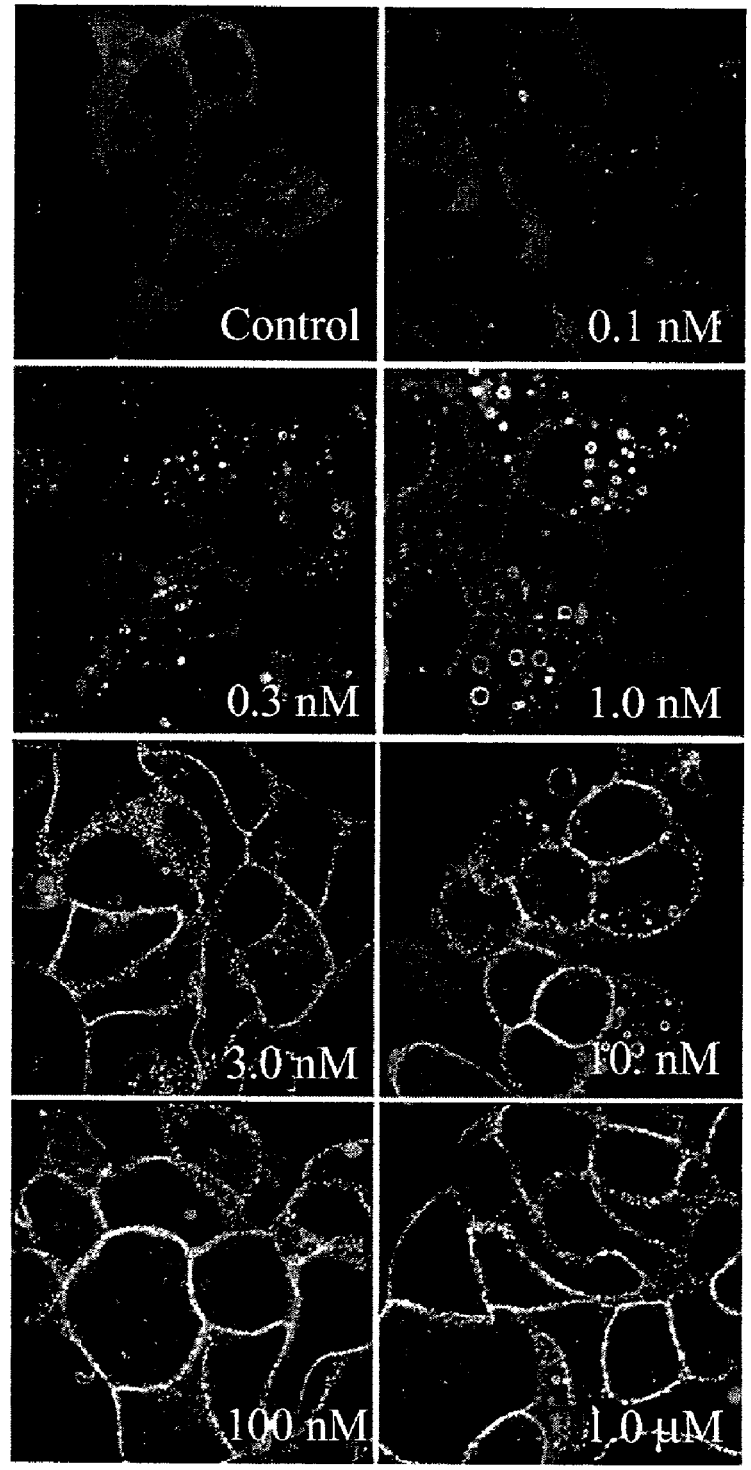
FIG. 6C illustrates images from an experiment demonstrating the response of Clone A cells exposed to hG17 for one hour at 37° C.

Serum samples from a patient with hypergastrinemia were evaluated in addition to hG17 using this 5 minutes assay paradigm (FIG. 6A). Arrestin translocated in response to the serum, but the measured response occurred in a range approximating the lower limits of assay sensitivity for hG17. In order to increase assay sensitivity at concentrations near or below 1 nM agonist, arrestin-GFP redistribution in response to hG17 after 1-2 hours of incubation at 37° C. was directly measured. FIG. 6C shows representative cell fields that were exposed to increasing concentrations of hG17. Vesicles are readily apparent at concentrations below 10 nM hG17.

FIG. 6A illustrates a representative experiment depicting the response of Clone A cells that were exposed to various concentrations of hG17 for 5 minutes. Fluorescence images were obtained every 30 seconds and analyzed for arrestin-GFP translocation. Nine to eleven cells were analyzed for each time point for each curve. The graph shows the fractional amount of arrestin-GFP remaining in the cytosol as a function of time. FIG. 6B shows that the fractional amount of arrestin-GFP lost after 5 minutes from the cell cytosol was used to generate a sigmoid dose response curve for the increasing concentrations of hG17 shown in the graph in A. Data are presented as mean±SEM. FIG. 6C shows images from an experiment demonstrating the response of Clone A cells exposed to hG17 for one hour at 37° C.

Example 5

Figure 7B:
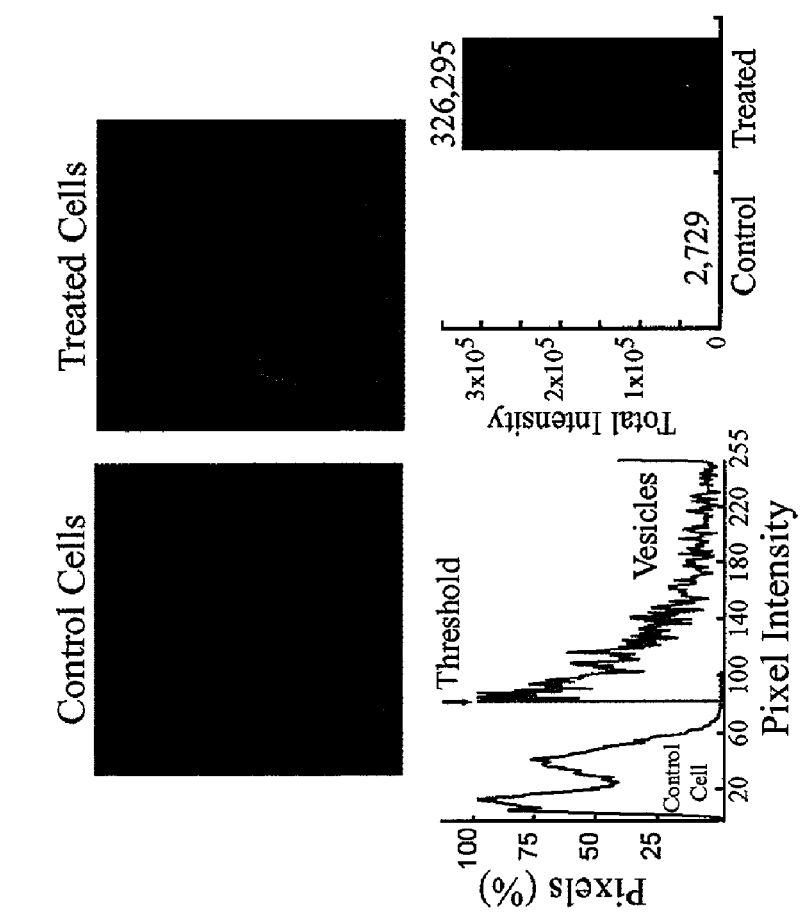
In FIG. 7B, a histogram of the pixel count versus pixel intensity (green curve in the graph at the lower left) was generated using a representative control cell.

Calculation of the Fluorescence Signal from the Distribution of βarrestin2-GFP The methodology for these measurements of Example 4 is described in FIG. 7. The signal over background obtained by simply measuring fluorescent intensities was quite large due to the concentration of translocated arrestins in small volumes, as shown in FIG. 7B where a 120-fold increase was observed.

Figure 7A:
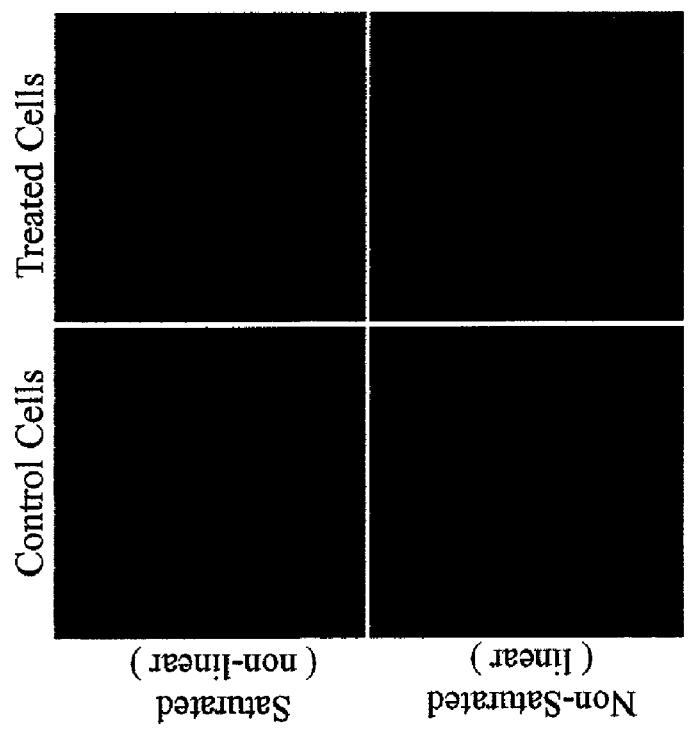
FIG. 7A shows the distribution of βarrestin-GFP fluorescence in cells stably expressing the βarrestin2-GFP fusion protein and receptor was visualized before and after a 30-minute agonist treatment.

FIG. 7A shows the distribution of βarrestin-GFP fluorescence in cells stably expressing the βarrestin2-GFP fusion protein. The receptor was visualized before and after a 30-minute agonist treatment. Image intensity was acquired using 8 bits per pixel, yielding a grayscale range of intensities from 0-255. Relative intensities greater than 255 were clipped and set equal to 255. The upper and lower panels show the same field of cells. The cells appear brighter in the upper panels because the average pixel intensity in the upper panels was selected to fall midway between 0-255. In the lower panels the mean pixel intensity falls within the bottom 12% of the dynamic range. The selection of a higher mean intensity caused many of the pixels representing translocated βarrestin2-GFP in the right upper panel to be clipped at a relative brightness of 255. This resulted in an underestimate of the amount of agonist-induced translocation, which is avoided in the lower images due to the selection of a smaller mean intensity. FIG. 7B illustrates a histogram of the pixel count versus pixel intensity (green curve in the graph at the lower left) was generated using a representative control cell. The first minimal intensity peak represents background and the second peak is green fluorescent protein. The mean cell intensity plus three standard deviations (>99$^{th}$ percentile) was selected as a threshold to separate the fluorescence signal of the untranslocated cytosolic βarrestin, from the βarrestin that translocated with the receptor into vesicles. Pixels with intensities above this baseline (magenta curve corresponds to vesicles in the treated cells) are indicated by the magenta color overlay in both the control and treated images (upper left an right panels). Note the correspondence between the magenta-colored pixels in the upper right image of FIG. 7B and the βarrestin-GFP-containing endocytic vesicles in the lower right image of FIG. 7A. Comparison of the total pixel intensity from pixels above the baseline for the two images is depicted in the lower right graph and shows a 120-fold increase in the fluorescence signal in the treated cells. Image data were analyzed by the computer program IP labs.

Example 6

Detection of Immunologically Undetectable Gastrin Receptor Agonists in serum: Dose Response to Pentagastrin There have been numerous reports of clinical hypergastrinemia in the absence of elevated serum gastrin levels. Consequently, RIA detection of serum gastrin may miss a group of patients with immunologically undetectable gastrin receptor agonists. Therefore the effects on translocation of the CCK-B receptor agonist pentagastrin, which is not detectable by conventional RIA, were evaluated. As illustrated in FIG. 8, the response of the biosensor to increasing amounts of pentagastrin produced a dose-response with an $EC_{50}$ for translocation of 2.4±1.9 nM, similar to the reported Kd of 1 nM for pentagastrin binding to the CCK-B receptor and 3.9 nM for polyphosphoinositide turnover.

Figure 8A:
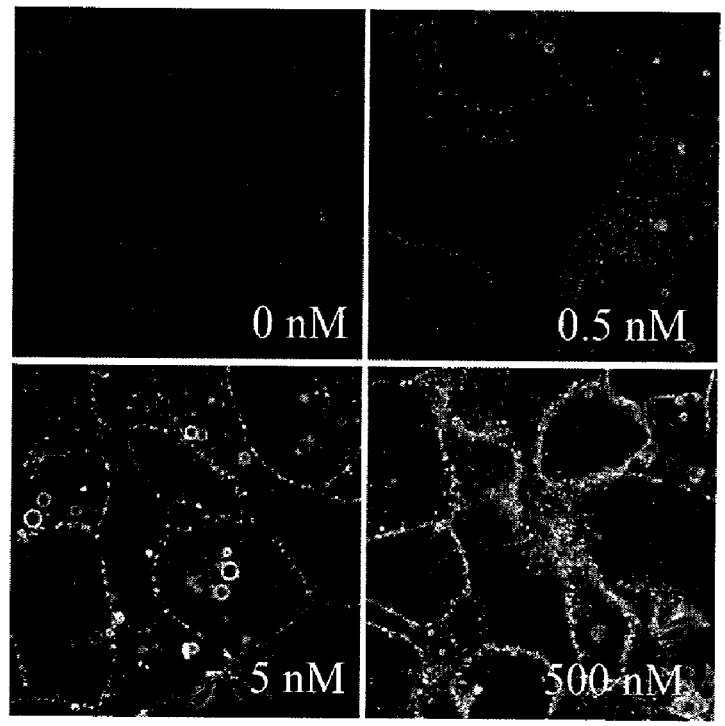
FIG. 8A shows images from a representative experiment depicting the response of Clone A cells that were exposed to pentagastrin at 37° C. for two hours. The graph in FIG. 8B depicts the increase in the normalized sum of pixel intensity (TI/TF) above a threshold value (Methods) for images obtained at each concentration of ligand.
Figure 8B:
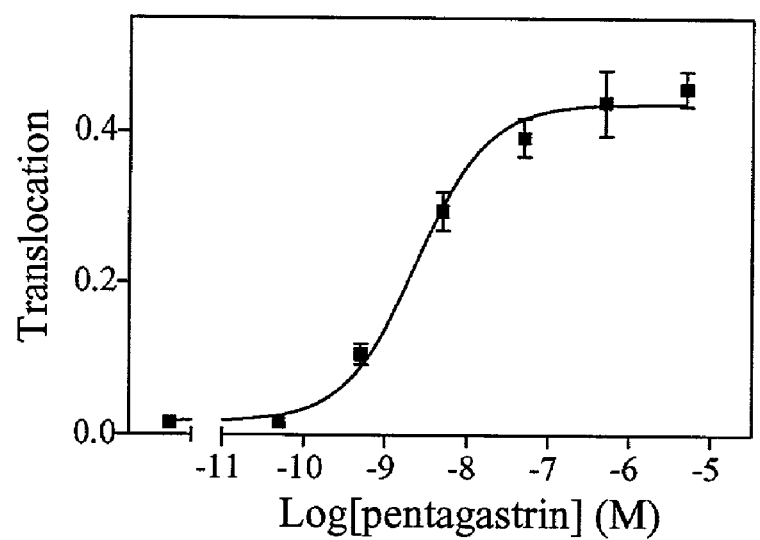
FIG. 8 shows the dose response to pentagastrin in an HEK-293 cell line containing arrestin-GFP and the CCK-B receptor.

FIG. 8A shows images from a representative experiment depicting the response of Clone A cells that were exposed to pentagastrin at 37° C. for two hours. Fluorescence images were analyzed for arrestin-GFP translocation as described in Methods. The graph in FIG. 8B depicts the increase in the normalized sum of pixel intensity (TI/TF) above a threshold value (Methods) for images obtained at each concentration of ligand. Data are representative of two experiments, each with eight to ten separate images and are presented as mean±SEM.

Example 7

Figure 9A:
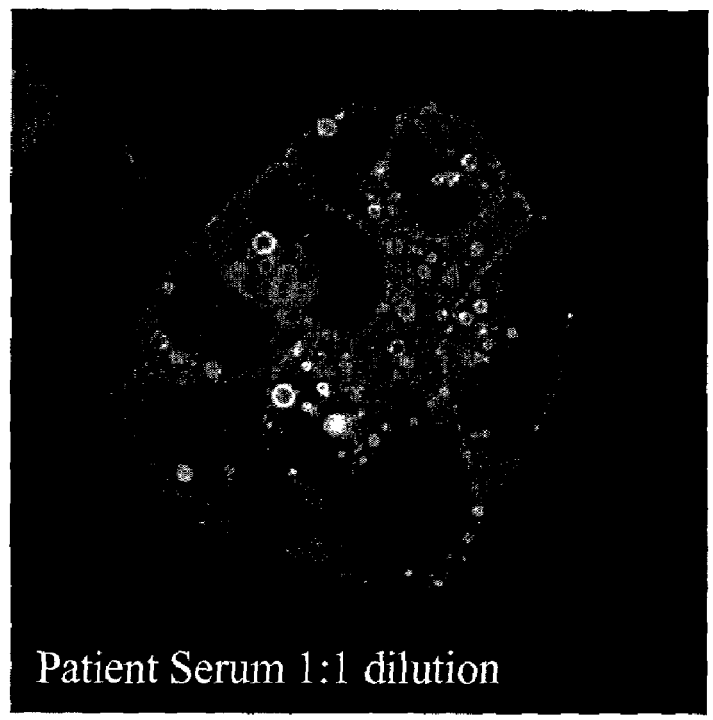
FIG. 9A illustrates the representative image of Clone A cells incubated for one hour with a 1:1 dilution of serum that was obtained from a patient with hypergastrinemia.

Detection of Gastrin from Patient with Hypergastrinemia: Dose Response at One Hour The ability of the biosensor to respond to various synthetic gastrin isoforms suggested its potential to measure the multitude of bioactive forms of gastrin contained in human serum. The upper panels in FIG. 9A show the cellular response to a patient serum sample (documented hypergastrinemia by RIA of 5000 pg/ml, range of 3,400 to 6,600 pg/ml) after one hour of incubation. Arrestin-GFP was seen at the plasma membrane and in vesicles. The amount of translocated arrestin-GFP was compared to an hG17 standard curve generated from the data represented by the images of FIG. 6C. The $EC_{50}$ of the hG17 dose response curve was (0.80±0.25) nM (FIGS. 6B and 6C), and the patient's bioactive gastrin serum concentration was determined to be 0.63 nM±0.16 nM (see arrow FIG. 9B).

Figure 9B:
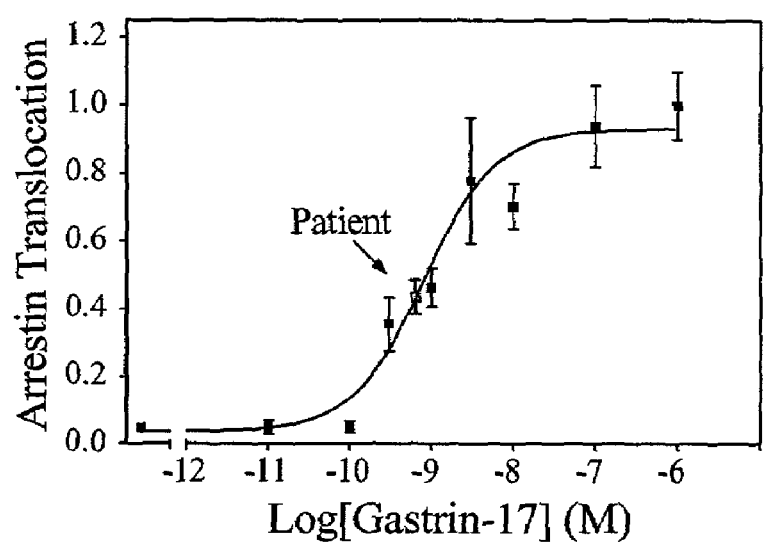
FIG. 9B shows the dose response curve to hG17 of Clone A cells computed from the imaged translocation data obtained at one hour and analyzed as in FIG. 7. Between 9 and 16 separate images were analyzed for each hG17 concentration and the patient's serum (arrow).

Depicted in FIG. 9A is a representative image of Clone A cells incubated for one hour with a 1:1 dilution of serum that was obtained from a patient with hypergastrinemia. FIG. 9B shows a dose response curve to hG17 of Clone A cells computed from the imaged translocation data obtained at one hour and analyzed as in FIG. 7. Between 9 and 16 separate images were analyzed for each hG17 concentration and the patient's serum (arrow). Data are presented as mean±SEM.

The present inventors demonstrated that the agonist-mediated arrestin interaction with the CCK-B receptor mirrored the pharmacology of CCK-B receptor signaling using a biosensor consisting of a cell permanently expressing CCK-B receptors and βarrestin2-GFP (arrestin-GFP). Moreover, this biosensor was used to determine the serum gastrin concentration of a patient with hypergastrinemia. All bioactive gastrin isoforms, including those not identified with conventional RIA, were detected with methods of the present invention.

These data show that the CCK-B receptor underwent agonist-mediated arrestin regulation. The IP3 receptor signaling was activated at the same gastrin and pentagastrin concentrations that produced arrestin translocation. The residues in gastrin that produce CCK-B receptor conformations capable of desensitization likely reside in the gastrin terminal pentapeptide.

After the CCK-B receptor bound agonist and arrestin initiated receptor internalization, the CCK-B receptor moved into the cell via arrestin-mediated clathrin-coated vesicular pathway. The CCK-B receptor was shown to be a "Class B" GPCR and subsequent receptor endocytosis may initiate secondary (or intracellular) signaling events, for example MAP kinase activation.

This pharmacology was exploited to construct a single cell biosensor to measure serum concentrations of gastrin. Given the large number of GPCRs that desensitize by arrestin, biosensors have been similarly constructed for other GPCR ligands; additional biosensors will be constructed. The novelty of this biological approach is that combinations of G protein-coupled receptors and fluorescent proteins form some of the most sensitive biosensor arrays developed and provide a mechanism to detect thousands of natural and synthetic compounds.

An area where synthetic compounds are clinically useful is in cancer chemotherapy. In particular, heptagastrin conjugated to an ellipticine moiety was used to kill tumors expressing the CCK-B receptor. The toxicity of this agent was shown to require receptor endocytosis, which based on our findings, was most likely arrestin dependent. This agent was administered to mice in concentrations well within the measurable range of our biosensor. The present invention has broad applications for the evaluation of newly designed drugs where the pharmacology is unknown and where serum or tissue levels need to be determined.

GPCRs signal the presence of bioactive substances. The present inventors exploited the common biochemical paradigm for terminating GPCR signaling and determined that GPCRs can also be used to detect those substances for clinical diagnosis.

Example 7

Muscarinic Receptor is Internalized in the Presence of Acetylcholine

Figure 10:
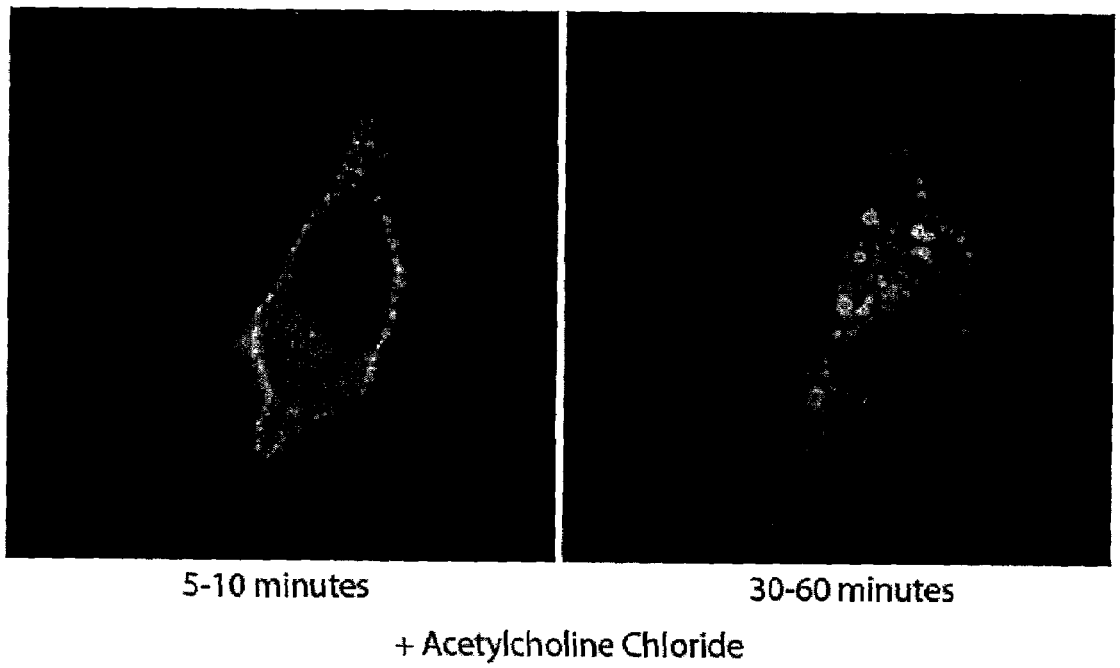
FIG. 10 illustrates the Internalization of muscarinic receptor in present of acetylcholine. HEK-293 cells expressing arrestin-GFP and the human muscarinic receptor type 1 conjugated with the Vasopressin carboxyl-terminal tail were exposed to micromolar concentrations of acetylcholine. Arrestin-GFP was observed at the membrane edge or in vesicles, in response to acetylcholine.

HEK-293 cells expressing the human muscarinic receptor type 1 conjugated with the vasopressin carboxyl tail were exposed to micromolar concentrations of acetylcholine. The translocation of arrestin-GFP was determined. Arrestin-GFP was observed at the membrane edge or in vesicles, as shown in FIG. 10.

The biosensor expressing the muscarinic receptor and arrestin-GFP was useful for the detection of acetylcholine in a sample, as indicated by the agonist-induced internalization of arrestin-GFP.

Example 8

Acetylcholinesterase Inhibits Acetylcholine Induced Internalization of Muscarinic Receptor HEK-293 cells were incubated in Minimal Essential Media containing 10% Fetal Bovine Serum (FBS). The cells had been transiently transfected with cDNA to induce the expression of arrestin-GFP and the human muscarinic receptor type 1 conjugated with the vasopressin carboxyl tail. In the presence of 10% FBS, no arrestin-GFP translocation was observed after the cells were exposed for up to 30 minutes to concentrations of acetylcholine in the range of 10-100 micromolar. However, millimolar amounts of acetylcholine did produce arrestin-GFP translocation. When cells were exposed to 10-20 micromolar concentrations of acetylcholine in the absence of serum, arrestin-GFP translocated readily to the cell membrane. Acetylcholinesterase, an enzyme known to degrade acetylcholine, is a common component of serum, including FBS. The acetylcholinesterase broke down the acetylcholine, the ligand of the muscarinic receptor, thereby preventing acetylcholine-induced internalization of the muscarinic receptor and arrestin. Exceeding large amounts of acetylcholine (millimolar) in the presence of acetylcholinesterase were able to produce only a transient amount of arrestin internalization. In contrast, a much smaller concentration of acetylcholine (10-20 micromolar) was able to produce a robust response when serum was absent from the media. This suggests that arrestin translocation can be used to assay serum for inhibitors of acetylcholinesterase, as a potent inhibitor such as an organophosphate compound would produce effects similar to removing the serum and all its constituent ingredients entirely from the environment of the test cell containing arrestin-GFP and the acetylcholine-exposed muscarinic receptor.

Example 9

Use of Muscarinic Acetyl Choline Receptor to Screen for Acetylcholinesterase Inhibitors A sample containing the putative inhibitor is extracted into an appropriate solvent, in one instance this may be an aqueous buffer. The extract either is diluted or combined with a buffer containing acetylcholinesterase protein and an agonist to the muscarinic receptor such as acetylcholine chloride sensitive to the acetylcholinesterase. This mixture containing the agonist, acetylcholinesterase, and the putative inhibitor is allowed to incubate for a given period of time between zero and a few hours, between 5 and 60 minutes is most practical, and then placed in contact with a cell containing the muscarinic receptor with its natural tail or the tail interchanged with a high affinity tail such as from the vasopressin receptor and arrestin-GFP. If a putative inhibitor of acetylcholinesterase is present, the acetylcholine chloride will not be broken down and translocation of the arrestin-GFP to the plasma membrane or endosomes will occur due to the activation of the receptor by the acetylcholine. If an inhibitor of the acetylcholinesterase is not present, the acetylcholine will be degraded and a lesser amount or no amount of arrestin-GFP translocation will occur. This assay can be used to assess commonly used inhibitors of the acetylcholinesterase enzyme in the environment such as the organophosphate insecticides, for example diazinon (EPA Completes Risk Assessment and Announces Risk Reduction Agreement for the Pesticide Diazinon. On Dec. 5, 2000, EPA released its revised risk assessment and announced an agreement with registrants to phase out/eliminate certain uses of the organophosphate pesticide diazinon.), and more potent inhibitors not commonly found such as derivatives the neurotoxin sarin. A particular use of such an assay system could be the continuous monitoring of a municipal water system for insecticides and like compounds by continuously adding aliquots of water, premixed with an acetylcholine chloride like agonist and acetylcholinesterase, to chambers with cells containing arrestin-GFP and the muscarinic receptor, and observing the cells for loss of inhibition of arrestin-GFP translocation. The assays can be performed on a high throughput basis by instruments that are commercially available for this purpose. Another use of this assay would be to assess a person's physiological exposure to compounds that inhibit acetylcholinesterase by measuring the presence of these compounds in serum or tissue. For example a drop of blood could directly be placed in a well containing a cell exposed to acetylcholine chloride and possessing, arrestin-GFP and the muscarinic acetylcholine receptor. Human blood or serum normally contains sufficient acetylcholinesterase to rapidly degrade acetylcholine. Thus, a loss of inhibition of the ability of the cell to translocate arrestin-GFP would be indicative of the presence of an acetylcholinesterase inhibitor.

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

The following is a list of documents related to the above disclosure and particularly to the experimental procedures and discussions. The following documents, as well as any documents referenced in the foregoing text, should be considered as incorporated by reference in their entirety.

Attramadal, H., Arriza, J. L., Aoki, C., Dawson, T. M., Codina, J., Kwatra, M. M., Snyder, S. H., Caron, M. G. & Lefkowitz, R. J. (1992) J. Biol. Chem. 267, 17882-17890

Barak, L. S., Oakley, R. H., Laporte, S. A. and Caron, M. G. (2001) Proc. Natl. Acad. Sci. USA 98, 93-98

Barak, L. S., Warabi, K., Feng, X., Caron, M. G. & Kwatra, M. M. (1999) J. Biol. Chem. 274, 7565-7569

Barak, L. S., Ferguson, S. S., Zhang, J. & Caron, M. G. (1997) J. Biol. Chem. 272, 27497-27500

Barak, L. S., Ferguson, S. S., Zhang, J., Martenson, C., Meyer, T. & Caron, M. G. (1997) Mol. Pharmacol. 51, 177-184

Barak, L. S., Menard, L., Ferguson, S. S., Colapietro, A. M. & Caron, M. G. (1995) Biochemistry 34, 15407-15414

Bardram, L, Rehfeld, J F (1988) Anal Biochem 175:537-43

Brady, C E, 3rd (1991) Am J Gastroenterol 86:129-34

Bugat, R, Thompson, M R, Aures, D, Grossman, M I (1976) Gastroenterology 74:754-9

Czerwinski, G, Tarasova, N I, Michejda, C J (1998) Proc Natl Acad Sci USA 95:11520-5

Daulhac, L, Kowalski-Chauvel, A, Pradayrol, L, Vaysse, N, Seva, C (1999). J Biol Chem 274:20657-63

Edkins, J. S. (1905) Proc R Soc Lond [Biol] 76:376

Ferguson, S. S., Barak, L. S., Zhang, J. & Caron, M. G. (1996) Can. J. Physiol. Pharmacol. 74, 1095-1110

Ferguson, S. S., Menard, L., Barak, L. S., Koch, W. J., Colapietro, A. M. & Caron, M. G. (1995) J. Biol. Chem. 270, 24782-24789

Ganguli, P C, Cullen, D R, Irvine W J (1971) Lancet 1:155-8

Goodman, O B, Jr., Krupnick, J G, Santini, F, et al. (1996) Nature 383:447-50

Gregory, R. A. & Tracy, H. J. (1964) Gut 5:103-117

Hersey, S J, Sachs, G (1995) Physiol Rev 75:155-89

Hughes, J, Boden, P, Costall, B, et al. (1990) Proc Natl Acad Sci USA 87:6728-32

Joshi, S N, Gardner, J D (1996) Dig Dis 14:334-44

Kim, K.-M., Valenzano, K. J., Robinson, S. R., Yao, W. D., Barak, L. S., Caron, M. G. (2001) J. Biol. Chem. 276: 37409-37414

Kopin, A S, Lee, Y M, McBride, E W, et al. (1992) Proc Natl Acad Sci USA 89:3605-9

Laporte, S. A., Oakley, R. H., Holt, J. A., Barak, L. S. & Caron, M. G. (2000) J. Biol. Chem. 275, 23120-23126

Laporte, S. A., Oakley, R. H., Zhang, J., Holt, J. A., Ferguson, S. S., Caron, M. G. & Barak, L. S. (1999) Proc. Natl. Acad. Sci. USA 96, 3712-3717

Lee, Y M, Beinborn, M, McBride, E W, L,u M, Kolakowski, L F, Jr., Kopin A S (1993) J Biol Chem 268:8164-9

Lefkowitz, R J (1998) J Biol Chem 273:18677-80

Leopoldt, D., Hanck, T., Exner, T., Maier, U., Wetzker, R., & Nürnberg, B. (1998) J. Biol. Chem. 273, 7024-7029

Liddle, R A (1994) Cholecystokinin. Raven Press, New York

Luttrell, L M, Ferguson, S S, Daaka, Y, et al. (1999) Science 283:655-61

Mantyh, C R, Pappas, T N, Vigna, S R (1994) Gastroenterology 107:1019-30

Menard, L., Ferguson, S. S., Zhang, J., Lin, F. T., Lefkowitz, R. J., Caron, M. G. & Barak, L. S. (1997) Mol. Pharmacol. 51, 800-808

Mhaouty-Kodja, S., Barak, L. S., Scheer, A., Abuin, L., Diviani, D., Caron, M. G. & Cotecchia, S. (1999) Mol. Pharmacol. 55, 339-347

Naga Prasad, S. V., Esposito, G., Mao, L., Koch, W. J., & Rockman, H. A. (2000) J. Biol. Chem. 275, 4693-4698

Naga Prasad, S. V., Barak, L. S., Rapacciuolo, A., Caron, M. G., & Rockman, H. A. (2001) J. Biol. Chem. 276, 18953-18959

Neuwald, A. F. & Hirano T. (2000) Genome Research 10, 1445-1452

Oakley, R. H., Laporte, S. A., Holt, J. A., Barak, L. S., Caron, M. G. (2001). J. Biol. Chem. 276: 19452-19460

Oakley, R. H., Laporte, S. A., Holt, J. A., Caron, M. G. & Barak, L. S. (2000) J. Biol. Chem. 275, 17201-17210

Oakley, R. H., Laporte, S. A., Holt, J. A., Barak, L. S. & Caron, M. G. (1999) J. Biol. Chem. 274, 32248-32257

Pisegna, J R, de Weerth, A, Huppi, K, Wank, S A (1992) Biochem Biophys Res Commun 189:296-303

Rehfeld, J. F. (1998) Physiol Rev 78:1087-108

Shetzline, M A, Premont, R T, Walker, J K, Vigna, S R, Caron, M G (1998) J Biol Chem 273:6756-62

Sloas, D D, Hirschowitz, B I, Chey, W Y (1990) J Clin Gastroenterol 12:573-8.

Smith, A J, Freedman, S B (1996) Life Sci 58:883-95

Sterne-Marr, R, Benovic, J L (1995) Vitam Horm 51:193-234 van Solinge, W W, Rehfeld, J F (1990) Clin Chim Acta 192:35-46

Walker, J K, Premont, R T, Barak, L S, Caron, M G, Shetzline, M A (1999) J Biol Chem 274:31515-23

Walsh, J H (1994) Gastrin. Raven Press, New York

Wank, S A (1995) Am J Physiol 269:G628-46

Wank, S A, Pisegna, J R, de Weerth, A (1992) Proc Natl Acad Sci USA 89:8691-5

Wilbanks, A. M., Laporte, S. A., Barak, L. S. & Caron, M. G. (2002) Manuscript submitted Wolfe, M M, Jain, D K, Edgerton, J R (1985) Ann Intern Med 103:215-7

Wolfe, M M, Jensen, R T (1987) N Engl J Med 317:1200-9

Zhang, J., Barak, L. S., Anborgh, P. H., Laporte, S. A., Caron, M. G. & Ferguson, S. S. (1999) J. Biol. Chem. 274, 10999-11006

Zhang, J., Barak, L. S., Winkler, K. E., Caron, M. G. & Ferguson, S. S. (1997) J. Biol. Chem. 272, 27005-27014

Zimmer, T, Stolzel, U, Bader, M, et al. (1995) N Engl J Med 333:634-6

What is claimed is:

1. A method of detecting the presence or absence of a G protein-coupled receptor (GPCR) ligand in a test sample, comprising the steps of:
   (a) providing a cell comprising a GPCR and a detectably labeled arrestin, wherein the cellular distribution of the detectably labeled arrestin changes in response to activation of the GPCR;
   (b) determining the cellular distribution of the detectably labeled arrestin in the absence of a test sample;
   (c) exposing the cell to the test sample;
   (d) determining the cellular distribution of the detectably labeled arrestin in the presence of the test sample; and
   (e) comparing the cellular distribution of the detectably labeled arrestin in the presence of the test sample to the cellular distribution of the detectably labeled arrestin in the absence of the test sample,
   wherein a change in the cellular distribution of the detectably labeled arrestin in the presence of the test sample in response to a GPCR ligand as compared to the cellular distribution of the detectably labeled arrestin in the absence of the test sample indicates the presence of a GPCR ligand in the test sample.

2. The method of claim 1, wherein the cellular distribution of the detectably labeled arrestin is determined at different time points after exposure to the test sample.

3. The method of claim 1, wherein the cellular distribution of the detectably labeled arrestin is determined after exposure to different concentrations of the test sample.

4. The method of claim 1, wherein the cellular distribution of the detectably labeled arrestin is quantified.

5. The method claim 4, wherein a concentration of the GPCR ligand in the test sample is quantified by comparing localization of the detectably labeled arrestin in plasma membrane, clathrin-coated pits, endocytic vesicles, or endosomes as compared to cytosol for the detectably labeled arrestin in the presence of the test sample to localization of the detectably labeled arrestin in plasma membrane, clathrin-coated pits, endocytic vesicles, or endosomes as compared to cytosol for the detectably labeled arrestin in the presence of a known concentration of the ligand.

6. The method of claim 5, wherein when a change in the concentration of the GPCR ligand in the test sample is observed over a period of time as a result of a compound that alters the concentration of the ligand indicates the presence of a compound in the test sample that alters the concentration of the ligand.

7. The method of claim 1, wherein the test sample is or is derived from serum, tissue, blood, or urine.

8. The method of claim 1 wherein the GPCR is CCK-B (SEQ ID NO: 13) or CCK-A (SEQ ID NO: 11).

9. The method of claim 8, wherein the test sample was derived from a patient with hypergastrinemia.

10. The method of claim 1, wherein the ligand is gastrin, preprogastrin, cleaved preprogastrin, gastrin-34, gastrin-17, pentagastrin, progastrin, glycine-extended gastrin-17, glycine-extended gastrin-34, gastrin-71, gastrin-6, hG17, a compound with an amidated tetrapeptide of the sequence Trp-Met-Asp-Phe-NH$_2$ (SEQ ID NO: 15), or an isoform of gastrin capable of binding to a gastrin receptor.

11. The method of claim 10, wherein the gastrin concentration is less than 10 nM.

12. The method of claim 1, wherein the GPCR is a muscarinic receptor.

13. The method of claim 1, wherein the ligand is acetylcholine.

14. The method of claim 1, wherein the labeled arrestin is localized in the cytosol, plasma membrane, clathrin-coated pits, endocytic vesicles, or endosomes.

15. The method of claim 1, wherein an increase in a local concentration of the detectably labeled arrestin in plasma membrane, clathrin-coated pits, endocytic vesicles, or endosomes as compared to cytosol results in an increase in a local signal intensity.

16. The method of claim 15, wherein the local signals intensity is increased in the presence of increased concentration of ligand in the test sample.

17. The method of claim 1, wherein a signal intensity of the labeled arrestin in the plasma membrane, clathrin-coated pits, endocytic vesicles, or endosomes is increased as compared to a level of signal intensity in the cytosol.

18. The method of claim 1, wherein the detectable label is a radioisotope, an epitope tag, an affinity label, an enzyme, a fluorescent group, or a chemiluminescent group.

19. The method of claim 1, wherein the cellular distribution is visualized by flow cytometry.

20. The method of claim 1, wherein the cellular distribution is visualized by fluorescence confocal microscopy.

21. The method of claim 1, wherein a computer analyzes an image of the cellular distribution.

22. The method of claim 1, wherein the distribution of the detectably labeled arrestin is quantified.

23. The method of claim 1, wherein the test sample comprises a ligand of the GPCR.

24. The method of claim 1, wherein the test sample comprises an antagonist of the GPCR.

25. The method of claim 1, wherein the test sample further comprises acetylcholine and acetylcholinesterase.

26. The method of claim 1, wherein the test sample further comprises an agonist of the GPCR.

27. The method of claim 1, wherein the ligand has been identified.

28. The method of claim 1, wherein the test sample is heterogeneous.

29. The method of claim 1, wherein the cellular distribution is determined after 15-30 minutes of exposure to the test sample.

30. The method of claim 1, wherein the cellular distribution is determined after 1 hour of exposure to the test sample.

31. The method of claim 1, wherein the cell is exposed to the test sample at a temperature of 37° C.

32. A method of detecting the presence or absence of a G protein-coupled receptor (GPCR) ligand in a test sample, comprising the steps of:
(a) providing a single cell biosensor comprising a cell which overexpresses a detectably labeled arrestin and at least one GPCR, wherein the cellular distribution of the detectably labeled arrestin changes in response to activation of the GPCR;
(b) determining the cellular distribution of the detectably labeled arrestin in the absence of a test sample;
(c) exposing the biosensor to the test sample;
(d) determining the cellular distribution of the detectably labeled arrestin in the presence of the test sample; and
(e) comparing the cellular distribution of the detectably labeled arrestin in the presence of the test sample to the cellular distribution of the detectably labeled arrestin in the absence of the test sample,
wherein a change in the cellular distribution of the detectably labeled arrestin in the presence of the test sample in response to a GPCR ligand as compared to the cellular distribution of the detectably labeled arrestin in the absence of the test sample indicates the presence of a GPCR ligand in the test sample.

33. A method of continuous screening for the presence or absence of G protein-coupled receptor (GPCR) ligands in a test sample, comprising the steps of:
(a) providing a cell comprising a GPCR and a detectably labeled arrestin, wherein the cellular distribution of the detectably labeled arrestin changes in response to activation of the GPCR;
(b) determining the cellular distribution of the detectably labeled arrestin in the absence of a test sample;
(c) exposing the cell to the test sample;
(d) determining the cellular distribution of the detectably labeled arrestin in the presence of the test sample;
(e) comparing the cellular distribution of the detectably labeled arrestin in the presence of the test sample in response to a GPCR ligand to the cellular distribution of the detectably labeled arrestin in the absence of the test sample, wherein a change in the cellular distribution of the detectably labeled arrestin in the presence of the test sample as compared to the cellular distribution of the detectably labeled arrestin in the absence of the test sample indicates the presence of a GPCR ligand in the test sample; and
(f) replacing the cell with another cell comprising a GPCR and a detectably labeled arrestin and repeating steps (b)-(e) thereby continuously screening for the presence or absence of G protein-coupled receptor (GPCR) ligands in a test sample.

34. A method of detecting the presence or absence of a compound that modulates G protein-coupled receptor (GPCR) internalization in a test sample, comprising the steps of:
(a) providing a cell comprising a GPCR and a detectably labeled arrestin, wherein the cellular distribution of the detectably labeled arrestin changes in response to activation of the GPCR and wherein when the GPCR is activated and internalized the GPCR and the detectably labeled arrestin form a detectably labeled arrestin/GPCR complex;
(b) determining the cellular distribution of the detectably labeled arrestin in the absence of a test sample;
(c) exposing the cell to an agonist of the GPCR,
(d) exposing the cell to the test sample;
(e) determining the cellular distribution of the detectably labeled arrestin/GPCR complex in the presence of the test sample; and
(f) comparing the cellular distribution of the detectably labeled arrestin/GPCR complex in the presence of the test sample to the cellular distribution of the detectably labeled arrestin in the absence of the test sample,
wherein a change in the cellular distribution of the detectably labeled arrestin/GPCR complex in the presence of the test sample as compared to the cellular distribution of the detectably labeled arrestin/GPCR complex in the absence of the test sample indicates the presence of a compound that modulates GPCR internalization in the test sample.

35. A method of detecting the presence or absence of a compound that modulates G protein-coupled receptor (GPCR) internalization in a test sample, comprising the steps of:
(a) providing a cell comprising a GPCR and a detectably labeled arrestin, wherein the cellular distribution of the detectably labeled arrestin changes in response to activation of the GPCR and wherein when the GPCR is activated and internalized the GPCR and the detectably labeled arrestin form a detectably labeled arrestin/GPCR complex;
(b) determining the cellular distribution of the detectably labeled arrestin in the presence of an agonist of the GPCR and the absence of a test sample;
(c) exposing the cell to the test sample;
(d) determining the cellular distribution of the detectably labeled arrestin/GPCR complex in the presence of the test sample; and
(e) comparing the cellular distribution of the detectably labeled arrestin/GPCR complex in the presence of the test sample to the cellular distribution of the detectably labeled arrestin in the absence of the test sample, wherein a change in the cellular distribution of the detectably labeled arrestin/GPCR complex in the presence of the test sample as compared to the cellular distribution of the detectably labeled arrestin/GPCR complex in the absence of the test sample indicates the presence of a compound that modulates GPCR internalization in the test sample.

* * * * *

SEQUENCE LISTING

<160> NUMBER OF SEQ ID NOS: 18

<210> SEQ ID NO 1
<211> LENGTH: 460
<212> TYPE: PRT

<213> ORGANISM: Homo sapiens

<400> SEQUENCE: 1

```
Met Asn Thr Ser Ala Pro Pro Ala Val Ser Pro Asn Ile Thr Val Leu
  1               5                  10                  15

Ala Pro Gly Lys Gly Pro Trp Gln Val Ala Phe Ile Gly Ile Thr Thr
             20                  25                  30

Gly Leu Leu Ser Leu Ala Thr Val Thr Gly Asn Leu Leu Val Leu Ile
         35                  40                  45

Ser Phe Lys Val Asn Thr Glu Leu Lys Thr Val Asn Asn Tyr Phe Leu
     50                  55                  60

Leu Ser Leu Ala Cys Ala Asp Leu Ile Ile Gly Thr Phe Ser Met Asn
 65                  70                  75                  80

Leu Tyr Thr Thr Tyr Leu Leu Met Gly His Trp Ala Leu Gly Thr Leu
             85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
        115                 120                 125

Arg Pro Leu Ser Tyr Arg Ala Lys Arg Thr Pro Arg Arg Ala Ala Leu
    130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Met Leu Ala Gly
                165                 170                 175

Gln Cys Tyr Ile Gln Phe Leu Ser Gln Pro Ile Ile Thr Phe Gly Thr
            180                 185                 190

Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
    210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
            260                 265                 270

Ser Trp Lys Glu Glu Glu Glu Asp Glu Gly Ser Met Glu Ser Leu
        275                 280                 285

Thr Ser Ser Glu Gly Glu Glu Pro Gly Ser Glu Val Val Ile Lys Met
    290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
            340                 345                 350

Lys Thr Phe Ser Leu Val Lys Glu Lys Lys Ala Ala Arg Thr Leu Ser
        355                 360                 365

Ala Ile Leu Leu Ala Phe Ile Leu Thr Trp Thr Pro Tyr Asn Ile Met
    370                 375                 380

Val Leu Val Ser Thr Phe Cys Lys Asp Cys Val Pro Glu Thr Leu Trp
385                 390                 395                 400
```

```
Glu Leu Gly Tyr Trp Leu Cys Tyr Val Asn Ser Thr Ile Asn Pro Met
            405                 410                 415
Cys Tyr Ala Leu Cys Asn Lys Ala Phe Arg Asp Thr Phe Arg Leu Leu
        420                 425                 430
Leu Leu Cys Arg Trp Asp Lys Arg Arg Trp Arg Lys Ile Pro Lys Arg
    435                 440                 445
Pro Gly Ser Val His Arg Thr Pro Ser Arg Gln Cys
    450                 455                 460
```

<210> SEQ ID NO 2
<211> LENGTH: 1383
<212> TYPE: DNA
<213> ORGANISM: Homo sapiens

<400> SEQUENCE: 2

| | | |
|---|---|---|
| atgaacactt cagccccacc tgctgtcagc cccaacatca ccgtcctggc accaggaaag | 60 |
| ggtccctggc aagtggcctt cattgggatc accacgggcc tcctgtcgct agccacagtg | 120 |
| acaggcaacc tgctggtact catctctttc aaggtcaaca cggagctcaa gacagtcaat | 180 |
| aactacttcc tgctgagcct ggcctgtgct gacctcatca tcggtacctt ctccatgaac | 240 |
| ctctatacca cgtacctgct catgggccac tgggctctgg gcacgctggc ttgtgacctc | 300 |
| tggctggccc tggactatgt ggccagcaat gcctccgtca tgaatctgct gctcatcagc | 360 |
| tttgaccgct acttctccgt gactcggccc ctgagctacc gtgccaagcg cacccccgc | 420 |
| cgggcagctc tgatgatcgg cctggcctgg ctggtttcct tgtgctctg gccccagcc | 480 |
| atcctcttct ggcagtacct ggtaggggag cggacgatgc tagctgggca gtgctacatc | 540 |
| cagttcctct cccagcccat catcaccttt ggcacagcca tggctgcctt ctacctccct | 600 |
| gtcacagtca tgtgcacgct ctactggcgc atctaccggg agacagagaa ccgagcacgg | 660 |
| gagctggcag cccttcaggg ctccgagacg ccaggcaaag ggggtggcag cagcagcagc | 720 |
| tcagagaggt ctcagccagg ggctgagggc tcaccagaga ctcctccagg ccgctgctgt | 780 |
| cgctgctgcc gggcccccag gctgctgcag gcctacagct ggaaggaaga agaggaagag | 840 |
| gacgaaggct ccatggagtc cctcacatcc tcagggggag aggagcctgg ctccgaagtg | 900 |
| gtgatcaaga tgccaatggt ggaccccgag gcacaggccc ccaccaagca gcccccacgg | 960 |
| agctccccaa atacagtcaa gaggccgact aagaaagggc gtgatcgagc tggcaagggc | 1020 |
| cagaagcccc gtggaaagga gcagctggcc aagcggaaga cctcctcgct ggtcaaggag | 1080 |
| aagaaggcgg ctcggaccct gagtgccatc ctcctggcct catcctcac ctggacaccg | 1140 |
| tacaacatca tggtgctggt gtccaccttc tgcaaggact gtgttcccga ccctgtgg | 1200 |
| gagctgggct actggctgtg ctacgtcaac agcaccatca cccccatgtg ctacgcactc | 1260 |
| tgcaacaaag ccttccggga cacctttcgc ctgctgctgc tttgccgctg ggacaagaga | 1320 |
| cgctggcgca gatccccaa gcgccctggc tccgtgcacc gcactccctc ccgccaatgc | 1380 |
| tga | 1383 |

<210> SEQ ID NO 3
<211> LENGTH: 466
<212> TYPE: PRT
<213> ORGANISM: Homo sapiens

<400> SEQUENCE: 3

```
Met Asn Asn Ser Thr Asn Ser Ser Asn Asn Ser Leu Ala Leu Thr Ser
 1               5                  10                  15
```

-continued

```
Pro Tyr Lys Thr Phe Glu Val Phe Ile Val Leu Val Ala Gly Ser
         20                  25                  30
Leu Ser Leu Val Thr Ile Ile Gly Asn Ile Leu Val Met Val Ser Ile
         35                  40                  45
Lys Val Asn Arg His Leu Gln Thr Val Asn Asn Tyr Phe Leu Phe Ser
 50                  55                  60
Leu Ala Cys Ala Asp Leu Ile Ile Gly Val Phe Ser Met Asn Leu Tyr
 65                  70                  75                  80
Thr Leu Tyr Thr Val Ile Gly Tyr Trp Pro Leu Gly Pro Val Val Cys
             85                  90                  95
Asp Leu Trp Leu Ala Leu Asp Tyr Val Val Ser Asn Ala Ser Val Met
             100                 105                 110
Asn Leu Leu Ile Ile Ser Phe Asp Arg Tyr Phe Cys Val Thr Lys Pro
             115                 120                 125
Leu Thr Tyr Pro Val Lys Arg Thr Thr Lys Met Ala Gly Met Met Ile
 130                 135                 140
Ala Ala Ala Trp Val Leu Ser Phe Ile Leu Trp Ala Pro Ala Ile Leu
 145                 150                 155                 160
Phe Trp Gln Phe Ile Val Gly Val Arg Thr Val Glu Asp Gly Glu Cys
             165                 170                 175
Tyr Ile Gln Phe Phe Ser Asn Ala Ala Val Thr Phe Gly Thr Ala Ile
             180                 185                 190
Ala Ala Phe Tyr Leu Pro Val Ile Ile Met Thr Val Leu Tyr Trp His
             195                 200                 205
Ile Ser Arg Ala Ser Lys Ser Arg Ile Lys Lys Asp Lys Lys Glu Pro
 210                 215                 220
Val Ala Asn Gln Asp Pro Val Ser Pro Ser Leu Val Gln Gly Arg Ile
 225                 230                 235                 240
Val Lys Pro Asn Asn Asn Asn Met Pro Ser Ser Asp Asp Gly Leu Glu
             245                 250                 255
His Asn Lys Ile Gln Asn Gly Lys Ala Pro Arg Asp Pro Val Thr Glu
             260                 265                 270
Asn Cys Val Gln Gly Glu Glu Lys Glu Ser Ser Asn Asp Ser Thr Ser
             275                 280                 285
Val Ser Ala Val Ala Ser Asn Met Arg Asp Asp Glu Ile Thr Gln Asp
             290                 295                 300
Glu Asn Thr Val Ser Thr Ser Leu Gly His Ser Lys Asp Glu Asn Ser
 305                 310                 315                 320
Lys Gln Thr Cys Ile Arg Ile Gly Thr Lys Thr Pro Lys Ser Asp Ser
             325                 330                 335
Cys Thr Pro Thr Asn Thr Thr Val Glu Val Val Gly Ser Ser Gly Gln
             340                 345                 350
Asn Gly Asp Glu Lys Gln Asn Ile Val Ala Arg Lys Ile Val Lys Met
             355                 360                 365
Thr Lys Gln Pro Ala Lys Lys Lys Pro Pro Pro Ser Arg Glu Lys Lys
 370                 375                 380
Val Thr Arg Thr Ile Leu Ala Ile Leu Leu Ala Phe Ile Ile Thr Trp
 385                 390                 395                 400
Ala Pro Tyr Asn Val Met Val Leu Ile Asn Thr Phe Cys Ala Pro Cys
             405                 410                 415
Ile Pro Asn Thr Val Trp Thr Ile Gly Tyr Trp Leu Cys Tyr Ile Asn
             420                 425                 430
Ser Thr Ile Asn Pro Ala Cys Tyr Ala Leu Cys Asn Ala Thr Phe Lys
```

```
                435                 440                 445
Lys Thr Phe Lys His Leu Leu Met Cys His Tyr Lys Asn Ile Gly Ala
        450                 455                 460

Thr Arg
465

<210> SEQ ID NO 4
<211> LENGTH: 1401
<212> TYPE: DNA
<213> ORGANISM: Homo sapiens

<400> SEQUENCE: 4
atgaataact caacaaactc ctctaacaat agcctggctc ttacaagtcc ttataagaca      60
tttgaagtgg tgtttattgt cctggtggct ggatccctca gtttggtgac cattatcggg     120
aacatcctag tcatggtttc cattaaagtc aaccgccacc tccagaccgt caacaattac     180
tttttattca gcttggcctg tgctgacctt atcataggtg ttttctccat gaacttgtac     240
accctctaca ctgtgattgg ttactggcct ttgggacctg tggtgtgtga cctttggcta     300
gccctggact atgtggtcag caatgcctca gttatgaatc tgctcatcat cagctttgac     360
aggtacttct gtgtcacaaa acctctgacc tacccagtca agcggaccac aaaaatggca     420
ggtatgatga ttgcagctgc ctgggtcctc tctttcatcc tctgggctcc agccattctc     480
ttctggcagt tcattgtagg ggtgagaact gtggaggatg gggagtgcta cattcagttt     540
ttttccaatg ctgctgtcac ctttggtacg gctattgcag ccttctattt gccagtgatc     600
atcatgactg tgctatattg gcacatatcc cgagccagca gagcaggat aaagaaggac     660 aagaaggagc ctgttgccaa ccaagacccc gtttctccaa gtctggtaca aggaaggata     720
gtgaagccaa acaataacaa catgcccagc agtgacgatg gcctggagca caacaaaatc     780
cagaatggca aagcccccag ggatcctgtg actgaaaaact gtgttcaggg agaggagaag     840
gagagctcca atgactccac ctcagtcagt gctgttgcct ctaatatgag agatgatgaa     900
ataacccagg atgaaaacac agtttccact tccctgggcc attccaaaga tgagaactct     960
aagcaaacat gcatcagaat tggcaccaag accccaaaaa gtgactcatg tacccccaact    1020 aataccaccg tggaggtagt ggggtcttca ggtcagaatg gagatgaaaa gcagaatatt    1080
gtagcccgca agattgtgaa gatgactaag cagcctgcaa aaaagaagcc tcctccttcc    1140
cgggaaaaga agtcaccag acaatcttg gctattctgt ggcttttcat catcacttgg    1200
gcccccatac aatgtcatggt gctcattaac acctttgtg caccttgcat ccccaacact    1260
gtgtggacaa ttggttactg gcttttgttac atcaacagca ctatcaaccc tgcctgctat    1320
gcactttgca atgccacctt caagaagacc tttaaacacc ttctcatgtg tcattataag    1380
aacataggcg ctacaaggta a                                              1401

<210> SEQ ID NO 5
<211> LENGTH: 590
<212> TYPE: PRT
<213> ORGANISM: Homo sapiens

<400> SEQUENCE: 5

Met Thr Leu His Asn Asn Ser Thr Thr Ser Pro Leu Phe Pro Asn Ile
  1               5                  10                  15

Ser Ser Ser Trp Ile His Ser Pro Ser Asp Ala Gly Leu Pro Pro Gly
                 20                  25                  30

Thr Val Thr His Phe Gly Ser Tyr Asn Val Ser Arg Ala Ala Gly Asn
```

-continued

```
                35                  40                  45

Phe Ser Ser Pro Asp Gly Thr Thr Asp Pro Leu Gly Gly His Thr
                         50                  55                  60

Val Trp Gln Val Val Phe Ile Ala Phe Leu Thr Gly Ile Leu Ala Leu
         65                  70                  75                  80

Val Thr Ile Ile Gly Asn Ile Leu Val Ile Val Ser Phe Lys Val Asn
                             85                  90                  95

Lys Gln Leu Lys Thr Val Asn Asn Tyr Phe Leu Leu Ser Leu Ala Cys
                        100                 105                 110

Ala Asp Leu Ile Ile Gly Val Ile Ser Met Asn Leu Phe Thr Thr Tyr
                    115                 120                 125

Ile Ile Met Asn Arg Trp Ala Leu Gly Asn Leu Ala Cys Asp Leu Trp
        130                 135                 140

Leu Ala Ile Asp Tyr Val Ala Ser Asn Ala Ser Val Met Asn Leu Leu
        145                 150                 155                 160

Val Ile Ser Phe Asp Arg Tyr Phe Ser Ile Thr Arg Pro Leu Thr Tyr
                        165                 170                 175

Arg Ala Lys Arg Thr Thr Lys Arg Ala Gly Val Met Ile Gly Leu Ala
                    180                 185                 190

Trp Val Ile Ser Phe Val Leu Trp Ala Pro Ala Ile Leu Phe Trp Gln
                195                 200                 205

Tyr Phe Val Gly Lys Arg Thr Val Pro Pro Gly Glu Cys Phe Ile Gln
        210                 215                 220

Phe Leu Ser Glu Pro Thr Ile Thr Phe Gly Thr Ala Ile Ala Ala Phe
        225                 230                 235                 240

Tyr Met Pro Val Thr Ile Met Thr Ile Leu Tyr Trp Arg Ile Tyr Lys
                        245                 250                 255

Glu Thr Glu Lys Arg Thr Lys Glu Leu Ala Gly Leu Gln Ala Ser Gly
                    260                 265                 270

Thr Glu Ala Glu Thr Glu Asn Phe Val His Pro Thr Gly Ser Ser Arg
                275                 280                 285

Ser Cys Ser Ser Tyr Glu Leu Gln Gln Gln Ser Met Lys Arg Ser Asn
        290                 295                 300

Arg Arg Lys Tyr Gly Arg Cys His Phe Trp Phe Thr Thr Lys Ser Trp
        305                 310                 315                 320

Lys Pro Ser Ser Glu Gln Met Asp Gln Asp His Ser Ser Ser Asp Ser
                        325                 330                 335

Trp Asn Asn Asn Asp Ala Ala Ala Ser Leu Glu Asn Ser Ala Ser Ser
                    340                 345                 350

Asp Glu Glu Asp Ile Gly Ser Glu Thr Arg Ala Ile Tyr Ser Ile Val
                355                 360                 365

Leu Lys Leu Pro Gly His Ser Thr Ile Leu Asn Ser Thr Lys Leu Pro
        370                 375                 380

Ser Ser Asp Asn Leu Gln Val Pro Glu Glu Glu Leu Gly Met Val Asp
        385                 390                 395                 400

Leu Glu Arg Lys Ala Asp Lys Leu Gln Ala Gln Lys Ser Val Asp Asp
                        405                 410                 415

Gly Gly Ser Phe Pro Lys Ser Phe Ser Lys Leu Pro Ile Gln Leu Glu
                    420                 425                 430

Ser Ala Val Asp Thr Ala Lys Thr Ser Asp Val Asn Ser Ser Val Gly
                435                 440                 445

Lys Ser Thr Ala Thr Leu Pro Leu Ser Phe Lys Glu Ala Thr Leu Ala
        450                 455                 460
```

```
Lys Arg Phe Ala Leu Lys Thr Arg Ser Gln Ile Thr Lys Arg Lys Arg
465                 470                 475                 480

Met Ser Leu Val Lys Glu Lys Lys Ala Ala Gln Thr Leu Ser Ala Ile
                485                 490                 495

Leu Leu Ala Phe Ile Ile Thr Trp Thr Pro Tyr Asn Ile Met Val Leu
                500                 505                 510

Val Asn Thr Phe Cys Asp Ser Cys Ile Pro Lys Thr Phe Trp Asn Leu
                515                 520                 525

Gly Tyr Trp Leu Cys Tyr Ile Asn Ser Thr Val Asn Pro Val Cys Tyr
                530                 535                 540

Ala Leu Cys Asn Lys Thr Phe Arg Thr Thr Phe Lys Met Leu Leu Leu
545                 550                 555                 560

Cys Gln Cys Asp Lys Lys Arg Arg Lys Gln Gln Tyr Gln Gln Arg
                565                 570                 575

Gln Ser Val Ile Phe His Lys Arg Ala Pro Glu Gln Ala Leu
                580                 585                 590

<210> SEQ ID NO 6
<211> LENGTH: 1773
<212> TYPE: DNA
<213> ORGANISM: Homo sapiens

<400> SEQUENCE: 6
atgaccttgc acaataacag tacaacctcg cctttgtttc caaacatcag ctcctcctgg      60
atacacagcc cctccgatgc agggctgccc ccgggaaccg tcactcattt cggcagctac     120
aatgtttctc gagcagctgg caatttctc tctccagacg gtaccaccga tgaccctctg      180
ggaggtcata ccgtctggca gtggtcttc atcgctttct taacgggcat cctggccttg     240
gtgaccatca tcggcaacat cctggtaatt gtgtcattta aggtcaacaa gcagctgaag     300
acggtcaaca actacttcct cttaagcctg gcctgtgccg atctgattat cggggtcatt     360
tcaatgaatc tgtttacgac ctacatcatc atgaatcgat gggccttagg aacttggcc      420
tgtgacctct ggcttgccat tgactacgta gccagcaatg cctctgttat gaatcttctg     480
gtcatcagct ttgacagata cttttccatc acgaggccgc tcacgtaccg agccaaacga     540
acaacaaaga gagccggtgt gatgatcggt ctggcttggg tcatctcctt gtcctttggg     600
gctcctgcca tcttgttctg gcaatacttt gttggaaaga gaactgtgcc tccgggagag     660
tgcttcattc agttcctcag tgagcccacc attactttg gcacagccat cgctgctttt     720
tatatgcctg tcaccattat gactatttta tactggagga tctataagga aactgaaaag     780
cgtaccaaag agcttgctgg cctgcaagcc tctgggacag aggcagagac agaaaacttt     840
gtccacccca cgggcagttc tcgaagctgc agcagttacg aacttcaaca gcaaagcatg     900
aaacgctcca caggaggaa gtatggccgc tgccacttct ggttcacaac caagagctgg     960
aaacccagct ccgagcagat ggaccaagac cacagcagca gtgacagttg aacaacaat    1020
gatgctgctg cctccctgga gaactccgcc tcctccgacg aggaggacat ggctccgag    1080
acgagagcca tctactccat cgtgctcaag cttccgggtc acagcaccat cctcaactcc    1140
accaagttac cctcatcgga caacctgcag gtgcctgagg aggagctggg gatggtggac    1200
ttggagagga agccgacaa gctgcaggcc agaagagcg tggacgatgg aggcagtttt    1260
ccaaaaagct tctccaagct tcccatccag ctagagtcag ccgtggacac agctaagact    1320
tctgacgtca actcctcagt gggtaagagc acggccactc tacctctgtc cttcaaggaa    1380
```

-continued

```
gccactctgg ccaagaggtt tgctctgaag accagaagtc agatcactaa gcggaaaagg    1440
atgtccctgg tcaaggagaa gaaagcggcc cagaccctca gtgcgatctt gcttgccttc    1500
atcatcactt ggaccccata acacatcatg gttctggtga acaccttttg tgacagctgc    1560 ataccccaaaa cctttggaa tctgggctac tggctgtgct acatcaacag caccgtgaac    1620
cccgtgtgct atgctctgtg caacaaaaca ttcagaacca ctttcaagat gctgctgctg    1680
tgccagtgtg acaaaaaaaa gaggcgcaag cagcagtacc agcagagaca gtcggtcatt    1740
tttcacaagc gcgcacccga gcaggccttg tag                                 1773
```

<210> SEQ ID NO 7
<211> LENGTH: 478
<212> TYPE: PRT
<213> ORGANISM: Homo sapiens

<400> SEQUENCE: 7

```
Met Ala Asn Phe Thr Pro Val Asn Gly Ser Ser Gly Asn Gln Ser Val
  1               5                  10                  15

Arg Leu Val Thr Ser Ser His Asn Arg Tyr Glu Thr Val Glu Met
             20                  25                  30

Val Phe Ile Ala Thr Val Thr Gly Ser Leu Ser Leu Val Thr Val Val
         35                  40                  45

Gly Asn Ile Leu Val Met Leu Ser Ile Lys Val Asn Arg Gln Leu Gln
     50                  55                  60

Thr Val Asn Asn Tyr Phe Leu Phe Ser Leu Ala Cys Ala Asp Leu Ile
 65                  70                  75                  80

Ile Gly Ala Phe Ser Met Asn Leu Tyr Thr Val Tyr Ile Ile Lys Gly
                 85                  90                  95

Tyr Trp Pro Leu Gly Ala Val Val Cys Asp Leu Trp Leu Ala Leu Asp
            100                 105                 110

Tyr Val Val Ser Asn Ala Ser Val Met Asn Leu Leu Ile Ile Ser Phe
        115                 120                 125

Asp Arg Tyr Phe Cys Val Thr Lys Pro Leu Thr Tyr Pro Ala Arg Arg
    130                 135                 140

Thr Thr Lys Met Ala Gly Leu Met Ile Ala Ala Trp Val Leu Ser
145                 150                 155                 160

Phe Val Leu Trp Ala Pro Ala Ile Leu Phe Trp Gln Phe Val Val Gly
                165                 170                 175

Lys Arg Thr Val Pro Asp Asn His Cys Phe Ile Gln Phe Leu Ser Asn
            180                 185                 190

Pro Ala Val Thr Phe Gly Thr Ala Ile Ala Ala Phe Tyr Leu Pro Val
        195                 200                 205

Val Ile Met Thr Val Leu Tyr Ile His Ile Ser Leu Ala Ser Arg Ser
    210                 215                 220

Arg Val His Lys His Arg Pro Glu Gly Pro Lys Glu Lys Lys Ala Lys
225                 230                 235                 240

Thr Leu Ala Phe Leu Lys Ser Pro Leu Met Lys Gln Ser Val Lys Lys
                245                 250                 255

Pro Arg Pro Gly Gly Arg Pro Gly Gly Leu Arg Asn Gly Lys Leu Glu
            260                 265                 270

Glu Ala Pro Pro Ala Leu Pro Pro Pro Arg Pro Val Ala Asp
        275                 280                 285

Lys Asp Thr Ser Asn Glu Ser Ser Ser Gly Ser Ala Thr Gln Asn Thr
    290                 295                 300
```

```
Lys Glu Arg Pro Ala Thr Glu Leu Ser Thr Thr Glu Ala Thr Thr Pro
305                 310                 315                 320

Ala Met Pro Ala Pro Pro Leu Gln Pro Arg Ala Leu Asn Pro Ala Ser
                325                 330                 335

Arg Trp Ser Lys Ile Gln Ile Val Thr Lys Gln Thr Gly Asn Glu Cys
            340                 345                 350

Val Thr Ala Ile Glu Ile Val Pro Ala Thr Pro Ala Gly Met Arg Pro
        355                 360                 365

Ala Ala Asn Val Ala Arg Lys Phe Ala Ser Ile Ala Arg Asn Gln Val
    370                 375                 380

Arg Lys Lys Arg Gln Met Ala Ala Arg Glu Arg Lys Val Thr Arg Thr
385                 390                 395                 400

Ile Phe Ala Ile Leu Leu Ala Phe Ile Leu Thr Trp Thr Pro Tyr Asn
                405                 410                 415

Val Met Val Leu Val Asn Thr Phe Cys Gln Ser Cys Ile Pro Asp Thr
                420                 425                 430

Val Trp Ser Ile Gly Tyr Trp Leu Cys Tyr Val Asn Ser Thr Ile Asn
            435                 440                 445

Pro Ala Cys Tyr Ala Leu Cys Asn Ala Thr Phe Lys Lys Thr Phe Arg
        450                 455                 460

His Leu Leu Leu Cys Gln Tyr Arg Asn Ile Gly Thr Ala Arg
465                 470                 475

<210> SEQ ID NO 8
<211> LENGTH: 1437
<212> TYPE: DNA
<213> ORGANISM: Homo sapiens

<400> SEQUENCE: 8
atggccaact tcacacctgt caatggcagc tcgggcaatc agtccgtgcg cctggtcacg      60
tcatcatccc acaatcgcta tgagacggtg gaaatggtct tcattgccac agtgacaggc     120
tccctgagcc tggtgactgt cgtgggcaac atcctggtga tgctgtccat caaggtcaac     180
aggcagctgc agacagtcaa caactacttc ctcttcagcc tggcgtgtgc tgatctcatc     240
ataggcgcct tctccatgaa cctctacacc gtgtacatca tcaagggcta ctggcccctg     300
ggcgccgtgg tctgcgacct gtggctggcc ctggactacg tggtgagcaa cgcctccgtc     360
atgaacttct catcatcag cttttgaccgc tacttctgcg tcaccaagcc tctcacctac     420 cctgccggc gcaccaccaa gatggcaggc ctcatgattg ctgctgcctg ggtactgtcc     480
ttcgtgctct gggcgcctgc catcttgttc tggcagtttg tggtgggtaa gcggacggtg     540
cccgacaacc actgcttcat ccagttcctg tccaacccag cagtgacctt ggcacagcc     600 attgctgcct tctacctgcc tgtggtcatc atgacggtgc tgtacatcca catctccctg     660
gccagtcgca gccagtcca caagcaccgg cccgagggcc cgaaggagaa gaaagccaag     720
acgctggcct tcctcaagag cccactaatg aagcagagcg tcaagaagcc ccgcccggga     780
ggccgcccgg gaggactgcg caatggcaag ctggaggagg ccccccgcc agcgctgcca     840 ccgccaccgc gccccgtggc tgataaggac acttccaatg agtccagctc aggcagtgcc     900
acccagaaca ccaaggaacg cccagccaca gagctgtcca ccacagaggc caccactccc     960
gccatgcccg cccctcccct gcagccgcgg gccctcaacc cagcctccag atggtccaag    1020
atccagattg tgacgaagca gacaggcaat gagtgtgtga cagccattga gattgtgcct    1080
gccacgccgg ctggcatgcg ccctgcggcc aacgtggccc gcaagttcgc cagcatcgct    1140
```

-continued

```
cgcaaccagg tgcgcaagaa gcggcagatg gcggcccggg agcgcaaagt gacacgaacg    1200
atctttgcca ttctgctagc cttcatcctc acctggacgc cctacaacgt catggtcctg    1260
gtgaacacct tctgccagag ctgcatccct gacacggtgt ggtccattgg ctactggctc    1320
tgctacgtca acagcaccat caaccctgcc tgctatgctc tgtgcaacgc cacctttaaa    1380
aagaccttcc ggcacctgct gctgtgccag tatcggaaca tcggcactgc caggtag      1437
```

<210> SEQ ID NO 9
<211> LENGTH: 614
<212> TYPE: PRT
<213> ORGANISM: Homo sapiens

<400> SEQUENCE: 9

```
Met Arg Pro Pro Gln Cys Leu Leu His Thr Pro Ser Leu Ala Ser Pro
 1               5                  10                  15

Leu Leu Leu Leu Leu Leu Trp Leu Leu Gly Gly Val Gly Ala Glu
            20                  25                  30

Gly Arg Glu Asp Ala Glu Leu Leu Val Thr Val Arg Gly Gly Arg Leu
        35                  40                  45

Arg Gly Ile Arg Leu Lys Thr Pro Gly Gly Pro Val Ser Ala Phe Leu
    50                  55                  60

Gly Ile Pro Phe Ala Glu Pro Pro Met Gly Pro Arg Arg Phe Leu Pro
65                  70                  75                  80

Pro Glu Pro Lys Gln Pro Trp Ser Gly Val Val Asp Ala Thr Thr Phe
                85                  90                  95

Gln Ser Val Cys Tyr Gln Tyr Val Asp Thr Leu Tyr Pro Gly Phe Glu
            100                 105                 110

Gly Thr Glu Met Trp Asn Pro Asn Arg Glu Leu Ser Glu Asp Cys Leu
        115                 120                 125

Tyr Leu Asn Val Trp Thr Pro Tyr Pro Arg Pro Thr Ser Pro Thr Pro
    130                 135                 140

Val Leu Val Trp Ile Tyr Gly Gly Gly Phe Tyr Ser Gly Ala Ser Ser
145                 150                 155                 160

Leu Asp Val Tyr Asp Gly Arg Phe Leu Val Gln Ala Glu Arg Thr Val
                165                 170                 175

Leu Val Ser Met Asn Tyr Arg Val Gly Ala Phe Gly Phe Leu Ala Leu
            180                 185                 190

Pro Gly Ser Arg Glu Ala Pro Gly Asn Val Gly Leu Leu Asp Gln Arg
        195                 200                 205

Leu Ala Leu Gln Trp Val Gln Glu Asn Val Ala Ala Phe Gly Gly Asp
    210                 215                 220

Pro Thr Ser Val Thr Leu Phe Gly Glu Ser Ala Gly Ala Ala Ser Val
225                 230                 235                 240

Gly Met His Leu Leu Ser Pro Pro Ser Arg Gly Leu Phe His Arg Ala
                245                 250                 255

Val Leu Gln Ser Gly Ala Pro Asn Gly Pro Trp Ala Thr Val Gly Met
            260                 265                 270

Gly Glu Ala Arg Arg Arg Ala Thr Gln Leu Ala His Leu Val Gly Cys
        275                 280                 285

Pro Pro Gly Gly Thr Gly Gly Asn Asp Thr Glu Leu Val Ala Cys Leu
    290                 295                 300

Arg Thr Arg Pro Ala Gln Val Leu Val Asn His Glu Trp His Val Leu
305                 310                 315                 320

Pro Gln Glu Ser Val Phe Arg Phe Ser Phe Val Pro Val Val Asp Gly
```

```
                    325                 330                 335
Asp Phe Leu Ser Asp Thr Pro Glu Ala Leu Ile Asn Ala Gly Asp Phe
            340                 345                 350
His Gly Leu Gln Val Leu Val Gly Val Val Lys Asp Glu Gly Ser Tyr
            355                 360                 365
Phe Leu Val Tyr Gly Ala Pro Gly Phe Ser Lys Asp Asn Glu Ser Leu
            370                 375                 380
Ile Ser Arg Ala Glu Phe Leu Ala Gly Val Arg Val Gly Val Pro Gln
385                 390                 395                 400
Val Ser Asp Leu Ala Ala Glu Ala Val Val Leu His Tyr Thr Asp Trp
            405                 410                 415
Leu His Pro Glu Asp Pro Ala Arg Leu Arg Glu Ala Leu Ser Asp Val
            420                 425                 430
Val Gly Asp His Asn Val Val Cys Pro Val Ala Gln Leu Ala Gly Arg
            435                 440                 445
Leu Ala Ala Gln Gly Ala Arg Val Tyr Ala Tyr Val Phe Glu His Arg
            450                 455                 460
Ala Ser Thr Leu Ser Trp Pro Leu Trp Met Gly Val Pro His Gly Tyr
465                 470                 475                 480
Glu Ile Glu Phe Ile Phe Gly Ile Pro Leu Asp Pro Ser Arg Asn Tyr
                485                 490                 495
Thr Ala Glu Glu Lys Ile Phe Ala Gln Arg Leu Met Arg Tyr Trp Ala
            500                 505                 510
Asn Phe Ala Arg Thr Gly Asp Pro Asn Glu Pro Arg Asp Pro Lys Ala
            515                 520                 525
Pro Gln Trp Pro Pro Tyr Thr Ala Gly Ala Gln Gln Tyr Val Ser Leu
            530                 535                 540
Asp Leu Arg Pro Leu Glu Val Arg Arg Gly Leu Arg Ala Gln Ala Cys
545                 550                 555                 560
Ala Phe Trp Asn Arg Phe Leu Pro Lys Leu Leu Ser Ala Thr Asp Thr
                565                 570                 575
Leu Asp Glu Ala Glu Arg Gln Trp Lys Ala Glu Phe His Arg Trp Ser
            580                 585                 590
Ser Tyr Met Val His Trp Lys Asn Gln Phe Asp His Tyr Ser Lys Gln
            595                 600                 605
Asp Arg Cys Ser Asp Leu
        610

<210> SEQ ID NO 10
<211> LENGTH: 2156
<212> TYPE: DNA
<213> ORGANISM: Homo sapiens

<400> SEQUENCE: 10
cagcctgcgc cggggaacat cggccgcctc cagctcccgg cgcggcccgg cccggcccgg     60
ctcggccgcc tcagacgccg cctgccctgc agccatgagg ccccccgcagt gtctgctgca   120 cacgccttcc ctggcttccc cactccttct cctcctcctc tggctcctgg gtggaggagt   180
gggggctgag gccgggagg atgcagagct gctggtgacg gtgcgtgggg gccggctgcg   240
gggcattcgc ctgaagaccc ccggggggccc tgtctctgct ttcctgggca tccccttttgc   300 ggagccaccc atgggacccc gtcgctttct gccaccggag cccaagcagc cttggtcagg   360
ggtggtagac gctacaacct tccagagtgt ctgctaccaa tatgtggaca ccctataccc   420
aggttttgag ggcaccgaga tgtggaaccc caaccgtgag ctgagcgagg actgcctgta   480
```

| | | |
|---|---|---|
| cctcaacgtg tggacaccat accccggcc tacatccccc accctgtcc tcgtctggat | 540 |
| ctatggggt ggcttctaca gtggggcctc ctccttggac gtgtacgatg ccgcttctt | 600 |
| ggtacaggcc gagaggactg tgctggtgtc catgaactac cgggtgggag cctttggctt | 660 |
| cctggccctg ccggggagcc gagaggcccc gggcaatgtg ggtctcctgg atcagaggct | 720 |
| ggccctgcag tgggtgcagg agaacgtggc agccttcggg ggtgacccga catcagtgac | 780 |
| gctgtttggg gagagcgcgg gagccgcctc ggtgggcatg cacctgctgt ccccgcccag | 840 |
| ccggggcctg ttccacaggg ccgtgctgca gagcggtgcc cccaatggac cctgggccac | 900 |
| ggtgggcatg ggagaggccc gtcgcagggc cacgcagctg gcccaccttg tgggctgtcc | 960 |
| tccaggcggc actggtggga atgacacaga gctggtagcc tgccttcgga cacgaccagc | 1020 |
| gcaggtcctg gtgaaccacg aatggcacgt gctgcctcaa gaaagcgtct tccggttctc | 1080 |
| cttcgtgcct gtggtagatg gagacttcct cagtgacacc ccagaggccc tcatcaacgc | 1140 |
| gggagacttc cacggcctgc aggtgctggt gggtgtggtg aaggatgagg gctcgtattt | 1200 |
| tctggtttac ggggcccag gcttcagcaa agacaacgag tctctcatca gccgggccga | 1260 |
| gttcctggcc ggggtgcggg tcggggttcc ccaggtaagt gacctggcag ccgaggctgt | 1320 |
| ggtcctgcat tacacagact ggctgcatcc cgaggacccg gcacgcctga gggaggccct | 1380 |
| gagcgatgtg gtgggcgacc acaatgtcgt gtgccccgtg gcccagctgg ctgggcgact | 1440 |
| ggctgcccag ggtgcccggg tctacgccta cgtctttgaa caccgtgctt ccacgctctc | 1500 |
| ctggcccctg tggatggggg tgccccacgg ctacgagatc gagttcatct ttgggatccc | 1560 |
| cctggacccc tctcgaaact acacggcaga ggagaaaatc ttcgcccagc gactgatgcg | 1620 |
| atactgggcc aactttgccc gcacagggga tcccaatgag ccccgagacc caaggcccc | 1680 |
| acaatggccc ccgtacacgg cgggggctca gcagtacgtt agtctggacc tgcggccgct | 1740 |
| ggaggtgcgg cgggggctgc gcgcccaggc ctgcgccttc tggaaccgct tcctccccaa | 1800 |
| attgctcagc gccaccgaca cgctcgacga ggcggagcgc cagtggaagg ccgagttcca | 1860 |
| ccgctggagc tcctacatgg tgcactggaa gaaccagttc gaccactaca gcaagcagga | 1920 |
| tcgctgctca gacctgtgac cccggcggga cccccatgtc ctccgctccg cccggccccc | 1980 |
| tagctgtata tactatttat ttcagggctg ggctataaca cagacgagcc ccagactctg | 2040 |
| cccatcccca ccccaccccg acgtcccccg gggctcccgg tcctctgcat gtctcaggct | 2100 |
| gagctccctc ccccgcggtg ccttcgcccc tctgggctgc caataaactg ttacag | 2156 |

<210> SEQ ID NO 11
<211> LENGTH: 428
<212> TYPE: PRT
<213> ORGANISM: Homo sapiens

<400> SEQUENCE: 11

Met Asp Val Val Asp Ser Leu Leu Val Asn Gly Ser Asn Ile Thr Pro
1               5                   10                  15

Pro Cys Glu Leu Gly Leu Glu Asn Glu Thr Leu Phe Cys Leu Asp Gln
            20                  25                  30

Pro Arg Pro Ser Lys Glu Trp Gln Pro Ala Val Gln Ile Leu Leu Tyr
        35                  40                  45

Ser Leu Ile Phe Leu Leu Ser Val Leu Gly Asn Thr Leu Val Ile Thr
    50                  55                  60

Val Leu Ile Arg Asn Lys Arg Met Arg Thr Val Thr Asn Ile Phe Leu
65                  70                  75                  80

```
Leu Ser Leu Ala Val Ser Asp Leu Met Leu Cys Leu Phe Cys Met Pro
             85                  90                  95
Phe Asn Leu Ile Pro Asn Leu Leu Lys Asp Phe Ile Phe Gly Ser Ala
            100                 105                 110
Val Cys Lys Thr Thr Thr Tyr Phe Met Gly Thr Ser Val Ser Val Ser
        115                 120                 125
Thr Phe Asn Leu Val Ala Ile Ser Leu Glu Arg Tyr Gly Ala Ile Cys
    130                 135                 140
Lys Pro Leu Gln Ser Arg Val Trp Gln Thr Lys Ser His Ala Leu Lys
145                 150                 155                 160
Val Ile Ala Ala Thr Trp Cys Leu Ser Phe Thr Ile Met Thr Pro Tyr
                165                 170                 175
Pro Ile Tyr Ser Asn Leu Val Pro Phe Thr Lys Asn Asn Asn Gln Thr
            180                 185                 190
Ala Asn Met Cys Arg Phe Leu Leu Pro Asn Asp Val Met Gln Gln Ser
        195                 200                 205
Trp His Thr Phe Leu Leu Leu Ile Leu Phe Leu Ile Pro Gly Ile Val
    210                 215                 220
Met Met Val Ala Tyr Gly Leu Ile Ser Leu Glu Leu Tyr Gln Gly Ile
225                 230                 235                 240
Lys Phe Glu Ala Ser Gln Lys Lys Ser Ala Lys Glu Arg Lys Pro Ser
                245                 250                 255
Thr Thr Ser Ser Gly Lys Tyr Glu Asp Ser Asp Gly Cys Tyr Leu Gln
            260                 265                 270
Lys Thr Arg Pro Pro Arg Lys Leu Glu Leu Arg Gln Leu Ser Thr Gly
        275                 280                 285
Ser Ser Ser Arg Ala Asn Arg Ile Arg Ser Asn Ser Ser Ala Ala Asn
    290                 295                 300
Leu Met Ala Lys Lys Arg Val Ile Arg Met Leu Ile Val Ile Val Val
305                 310                 315                 320
Leu Phe Phe Leu Cys Trp Met Pro Ile Phe Ser Ala Asn Ala Trp Arg
                325                 330                 335
Ala Tyr Asp Thr Ala Ser Ala Glu Arg Arg Leu Ser Gly Thr Pro Ile
            340                 345                 350
Ser Phe Ile Leu Leu Leu Ser Tyr Thr Ser Ser Cys Val Asn Pro Ile
        355                 360                 365
Ile Tyr Cys Phe Met Asn Lys Arg Phe Arg Leu Gly Phe Met Ala Thr
    370                 375                 380
Phe Pro Cys Cys Pro Asn Pro Gly Pro Pro Gly Ala Arg Gly Glu Val
385                 390                 395                 400
Gly Glu Glu Glu Glu Gly Gly Thr Thr Gly Ala Ser Leu Ser Arg Phe
                405                 410                 415
Ser Tyr His Met Ser Ala Ser Val Pro Pro Gln
            420                 425

<210> SEQ ID NO 12
<211> LENGTH: 1393
<212> TYPE: DNA
<213> ORGANISM: Homo sapiens

<400> SEQUENCE: 12
cattagagga atgagccggg agtgagcaat tcaccagctc tccagcactt ggtggaaagc      60
agcaggcaag gatggatgtg gttgacagcc ttcttgtgaa tggaagcaac atcactcctc     120
```

-continued

```
cctgtgaact cgggctcgaa aatgagacgc tttctgctt ggatcagccc cgtccttcca    180
aagagtggca gccagcggtg cagattctct tgtactcctc gatattcctg ctcagcgtgc    240
tgggaaacac gctggtcatc accgtgctga ttcggaacaa gcggatgcgg acggtcacca    300
acatcttcct cctctccctg gctgtcagcg acctcatgct ctgtctcttc tgcatgccgt    360
tcaacctcat ccccaatctg ctcaaggatt tcatcttcgg gagcgccgtt tgcaagacca    420
ccacctactt catgggcacc tctgtgagtg tatctacctt taatctggta gccatatctc    480
tagagagata tggtgcgatt tgcaaaccct acagtcccg ggtctggcag acaaaatccc    540
atgctttgaa ggtgattgct gctacctggt gcctttcctt taccatcatg actccgtacc    600
ccatttatag caacttggtg ccttttacca aaataacaa ccagaccgcg aatatgtgcc    660
gctttctact gccaaatgat gttatgcagc agtcctggca cacattcctg ttactcatcc    720
tctttcttat tcctggaatt gtgatgatgg tggcatatgg attaatctct ttggaactct    780
accagggaat aaaatttgag gctagccaga agaagtctgc taaagaaagg aaacctagca    840
ccaccagcag cggcaaatat gaggacagcg atgggtgtta cctgcaaaag accaggcccc    900
cgaggaagct ggagctccgg cagctgtcca ccggcagcag cagcagggcc aaccgcatcc    960
ggagtaacag ctccgcagcc aacctgatgg ccaagaaaag ggtgatccgc atgctcatcg    1020
tcatcgtggt cctcttcttc ttgtgctgga tgcccatctt cagcgccaac gcctggcggg    1080
cctacgacac cgcctccgca gagcgccgcc tctcaggaac ccccatttcc ttcatcctcc    1140
tcctgtccta cacctcctcc tgcgtcaacc ccatcatcta ctgcttcatg aacaaacgct    1200
tccgcctcgg cttcatggcc accttcccct gctgccccaa tcctggtccc cagggggcga    1260
ggggagaggt gggggaggag gaggaaggcg ggaccacagg agcctctctg tccaggttct    1320
cgtacagcca tatgagtgcc tcggtgccac cccagtgaga tgtcccctga ccctccaccg    1380
cagaaggaag gca                                                        1393
```

<210> SEQ ID NO 13
<211> LENGTH: 447
<212> TYPE: PRT
<213> ORGANISM: Homo sapiens

<400> SEQUENCE: 13

```
Met Glu Leu Leu Lys Leu Asn Arg Ser Val Gln Gly Thr Gly Pro Gly
 1               5                  10                  15

Pro Gly Ala Ser Leu Cys Arg Pro Gly Ala Pro Leu Leu Asn Ser Ser
             20                  25                  30

Ser Val Gly Asn Leu Ser Cys Glu Pro Pro Arg Ile Arg Gly Ala Gly
         35                  40                  45

Thr Arg Glu Leu Glu Leu Ala Ile Arg Ile Thr Leu Tyr Ala Val Ile
     50                  55                  60

Phe Leu Met Ser Val Gly Gly Asn Met Leu Ile Ile Val Val Leu Gly
 65                  70                  75                  80

Leu Ser Arg Arg Leu Arg Thr Val Thr Asn Ala Phe Leu Leu Ser Leu
                 85                  90                  95

Ala Val Ser Asp Leu Leu Leu Ala Val Ala Cys Met Pro Phe Thr Leu
            100                 105                 110

Leu Pro Asn Leu Met Gly Thr Phe Ile Phe Gly Thr Val Ile Cys Lys
        115                 120                 125

Ala Val Ser Tyr Leu Met Gly Val Ser Val Ser Val Ser Thr Leu Ser
    130                 135                 140
```

-continued

```
Leu Val Ala Ile Ala Leu Glu Arg Tyr Ser Ala Ile Cys Arg Pro Leu
145                 150                 155                 160

Gln Ala Arg Val Trp Gln Thr Arg Ser His Ala Ala Arg Val Ile Val
                165                 170                 175

Ala Thr Trp Leu Leu Ser Gly Leu Leu Met Val Pro Tyr Pro Val Tyr
            180                 185                 190

Thr Val Val Gln Pro Val Gly Pro Arg Val Leu Gln Cys Val His Arg
        195                 200                 205

Trp Pro Ser Ala Arg Val Arg Gln Thr Trp Ser Val Leu Leu Leu Leu
    210                 215                 220

Leu Leu Phe Phe Ile Pro Gly Val Val Met Ala Val Ala Tyr Gly Leu
225                 230                 235                 240

Ile Ser Arg Glu Leu Tyr Leu Gly Leu Arg Phe Asp Gly Asp Ser Asp
                245                 250                 255

Ser Asp Ser Gln Ser Arg Val Arg Asn Gln Gly Gly Leu Pro Gly Ala
                260                 265                 270

Val His Gln Asn Gly Arg Cys Arg Pro Glu Thr Gly Ala Val Gly Glu
            275                 280                 285

Asp Ser Asp Gly Cys Tyr Val Gln Leu Pro Arg Ser Arg Pro Ala Leu
        290                 295                 300

Glu Leu Thr Ala Leu Thr Ala Pro Gly Pro Gly Ser Gly Ser Arg Pro
305                 310                 315                 320

Thr Gln Ala Lys Leu Leu Ala Lys Lys Arg Val Val Arg Met Leu Leu
                325                 330                 335

Val Ile Val Val Leu Phe Phe Leu Cys Trp Leu Pro Val Tyr Ser Ala
            340                 345                 350

Asn Thr Trp Arg Ala Phe Asp Gly Pro Gly Ala His Arg Ala Leu Ser
        355                 360                 365

Gly Ala Pro Ile Ser Phe Ile His Leu Leu Ser Tyr Ala Ser Ala Cys
    370                 375                 380

Val Asn Pro Leu Val Tyr Cys Phe Met His Arg Arg Phe Arg Gln Ala
385                 390                 395                 400

Cys Leu Glu Thr Cys Ala Arg Cys Cys Pro Arg Pro Pro Arg Ala Arg
                405                 410                 415

Pro Arg Ala Leu Pro Asp Glu Asp Pro Pro Thr Pro Ser Ile Ala Ser
            420                 425                 430

Leu Ser Arg Leu Ser Tyr Thr Thr Ile Ser Thr Leu Gly Pro Gly
        435                 440                 445

<210> SEQ ID NO 14
<211> LENGTH: 1969
<212> TYPE: DNA
<213> ORGANISM: Homo sapiens

<400> SEQUENCE: 14
atggagctgc tcaagctgaa ccggagcgtg cagggaaccg acccgggcc gggggcttcc        60 ctgtgccgcc gggggcgcc tctcctcaac agcagcagtg tgggcaacct cagctgcgag       120
ccccctcgca ttcgcggagc cgggacacga gaattggagc tggccattag aatcactctt      180
tacgcagtga tcttcctgat gagcgttgga ggaaatatgc tcatcatcgt ggtcctggga      240
ctgagccgcc gcctgaggac tgtcaccaat gccttcctcc tctcactggc agtcagcgac      300
ctcctgctgg ctgtggcttg catgcccttc accctcctgc ccaatctcat gggcacattc      360
atctttggca ccgtcatctg caaggcggtt tcctacctca tggggtgtc tgtgagtgtg      420
```

-continued

```
tccacgctaa gcctcgtggc catcgcactg gagcggtaca gcgccatctg ccgaccactg      480
caggcacgag tgtggcagac gcgctcccac gcggctcgcg tgattgtagc cacgtggctg      540
ctgtccggac tactcatggt gccctacccc gtgtacactg tcgtgcaacc agtggggcct      600
cgtgtgctgc agtgcgtgca tcgctggccc agtgcgcggg tccgcagac ctggtccgta      660 ctgctgcttc tgctcttgtt cttcatcccg ggtgtggtta tggccgtggc ctacgggctt      720
atctctcgcg agctctactt agggcttcgc tttgacggcg acagtgacag cgacagccaa      780
agcagggtcc gaaaccaagg cgggctgcca ggggctgttc accagaacgg gcgttgccgg      840
cctgagactg gcgcggttgg cgaagacagc gatggctgct acgtgcaact ccacgttcc       900 cggcctgccc tggagctgac ggcgctgacg gctccagggc cgggatccgg ctcccggccc      960
acccaggcca agctgctggc taagaagcgc gtggtgcgaa tgttgctggt gatcgttgtg     1020
cttttttttc tgtgttggtt gccagtttat agtgccaaca cgtggcgcgc ctttgatggc     1080
ccgggtgcac accgagcact ctcgggtgct cctatctcct tcattcactt gctgagctac     1140
gcctcggcct gtgtcaaccc cctggtctac tgcttcatgc accgtcgctt cgccaggcc      1200 tgcctggaaa cttgcgctcg ctgctgcccc cggcctccac gagctcgccc cagggctctt     1260
cccgatgagg accctcccac tccctccatt gcttcgctgt ccaggcttag ctacaccacc     1320
atcagcacac tgggccctgg ctgaggagta gaggggccgt gggggttgag gcagggcaaa     1380
tgacatgcac tgacccttcc agacatagaa acacaaacc acaactgaca caggaaaacca     1440 acacccaaag catggactaa ccccaacgac aggaaaaggt agcttacctg acacaagagg     1500
aataagaatg gagcagtaca tgggaaagga ggcatgcctc tgatatggga ctgagcctgg     1560
cccatagaaa catgacactg accttggaga gacagagcgt ccctagcagt gaactatttc     1620
tacacagtgg gaactctgac aagggctgac ctgcctctca cacacataga ttaatggcac     1680
tgattgtttt agagactatg gagcctggca caggactgac tctgggatgc tcctagtttg     1740
acctcacagt gaccottccc aatcagcact gaaaatacca tcaggcctaa tctcatacct     1800
ctgaccaaca ggctgttctg cactgaaaag gttcttcatc cctttccagt taaggaccgt     1860
ggccctgccc tctccttcct tcccaaactg ttcaagaaat aataaattgt ttggcttcct     1920
cctgaaaaaa aaaaaaaaaa aaaaaaaaaa aaaaaaaaaa aggaattcc                 1969
```

```
<210> SEQ ID NO 15
<211> LENGTH: 4
<212> TYPE: PRT
<213> ORGANISM: Artificial Sequence
<220> FEATURE:
<223> OTHER INFORMATION: amidated tetrapeptide

<400> SEQUENCE: 15

Trp Met Asp Phe
 1

<210> SEQ ID NO 16
<211> LENGTH: 5
<212> TYPE: PRT
<213> ORGANISM: Artificial Sequence
<220> FEATURE:
<223> OTHER INFORMATION: conserved amino acid motif
<220> FEATURE:
<221> NAME/KEY: VARIANT
<222> LOCATION: 3, 4
<223> OTHER INFORMATION: Xaa = Any Amino Acid

<400> SEQUENCE: 16
```

```
Asn Pro Xaa Xaa Tyr
 1               5
```

```
<210> SEQ ID NO 17
<211> LENGTH: 42
<212> TYPE: DNA
<213> ORGANISM: Artificial Sequence
<220> FEATURE:
<223> OTHER INFORMATION: primer

<400> SEQUENCE: 17
gcgcccgcta gcaccgccat ggagctgcta aagctgaacc gg          42

<210> SEQ ID NO 18
<211> LENGTH: 36
<212> TYPE: DNA
<213> ORGANISM: Artificial Sequence
<220> FEATURE:
<223> OTHER INFORMATION: primer

<400> SEQUENCE: 18
gcgcccggta cctcagccag ggcccagtgt gctgat                 36
```